US010842561B2

(12) United States Patent
Viswanathan et al.

(10) Patent No.: US 10,842,561 B2
(45) Date of Patent: *Nov. 24, 2020

(54) SYSTEMS, DEVICES, AND METHODS FOR DELIVERY OF PULSED ELECTRIC FIELD ABLATIVE ENERGY TO ENDOCARDIAL TISSUE

(71) Applicant: Farapulse, Inc., Menlo Park, CA (US)

(72) Inventors: Raju Viswanathan, Mountain View, CA (US); Gary Long, Cincinnati, OH (US); Jean-Luc Pageard, Montreal (CA); Brittney Hachey, Dorval (CA)

(73) Assignee: Farapulse, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/595,250

(22) Filed: Oct. 7, 2019

(65) Prior Publication Data
US 2020/0046423 A1 Feb. 13, 2020

Related U.S. Application Data

(63) Continuation of application No. 16/240,066, filed on Jan. 4, 2019, now Pat. No. 10,433,908, which is a (Continued)

(51) Int. Cl.
*A61B 18/14* (2006.01)
*A61N 1/37* (2006.01)
(Continued)

(52) U.S. Cl.
CPC .......... *A61B 18/1492* (2013.01); *A61N 1/056* (2013.01); *A61N 1/327* (2013.01);
(Continued)

(58) Field of Classification Search
CPC ............ A61B 18/1206; A61B 18/1492; A61B 2017/00154; A61B 2018/00083;
(Continued)

(56) References Cited

U.S. PATENT DOCUMENTS 4,200,104 A 4/1980 Harris
4,470,407 A 9/1984 Hussein
(Continued)

FOREIGN PATENT DOCUMENTS

EP 1042990 A1 10/2000
EP 1125549 8/2001
(Continued)

OTHER PUBLICATIONS

Partial Supplementary European Search Report for European Application No. 13827672.0, dated Mar. 23, 2016, 6 pages.
(Continued)

*Primary Examiner* — Michael F Peffley
*Assistant Examiner* — Amanda L Zink
(74) *Attorney, Agent, or Firm* — Cooley LLP

(57) ABSTRACT

Systems, devices, and methods for electroporation ablation therapy are disclosed, with the system including a pulse waveform signal generator for medical ablation therapy, and an endocardial ablation device includes at least one electrode for ablation pulse delivery to tissue. The signal generator may deliver voltage pulses to the ablation device in the form of a pulse waveform. The system may include a cardiac stimulator for generation of pacing signals and for sequenced delivery of pulse waveforms in synchrony with the pacing signal.

28 Claims, 46 Drawing Sheets

Related U.S. Application Data continuation of application No. 15/711,266, filed on Sep. 21, 2017, now Pat. No. 10,172,673, which is a continuation-in-part of application No. PCT/US2017/012099, filed on Jan. 4, 2017.

(60) Provisional application No. 62/529,268, filed on Jul. 6, 2017, provisional application No. 62/491,910, filed on Apr. 28, 2017, provisional application No. 62/274,943, filed on Jan. 5, 2016.

(51) Int. Cl.
| | |
|---|---|
| *A61N 1/05* | (2006.01) |
| *A61N 1/32* | (2006.01) |
| A61M 25/01 | (2006.01) |
| A61B 18/00 | (2006.01) |
| A61B 18/12 | (2006.01) |
| A61B 17/00 | (2006.01) |
| A61B 90/00 | (2016.01) |
| A61N 1/362 | (2006.01) |

(52) U.S. Cl.
CPC .......... *A61N 1/371* (2013.01); *A61B 18/1206* (2013.01); *A61B 2017/00154* (2013.01); *A61B 2018/0016* (2013.01); *A61B 2018/0022* (2013.01); *A61B 2018/0025* (2013.01); *A61B 2018/00083* (2013.01); *A61B 2018/00267* (2013.01); *A61B 2018/00351* (2013.01); *A61B 2018/00357* (2013.01); *A61B 2018/00375* (2013.01); *A61B 2018/00577* (2013.01); *A61B 2018/00613* (2013.01); *A61B 2018/00839* (2013.01); *A61B 2018/00988* (2013.01); *A61B 2018/1266* (2013.01); *A61B 2018/1407* (2013.01); *A61B 2018/1435* (2013.01); *A61B 2018/1467* (2013.01); *A61B 2090/3966* (2016.02); *A61B 2218/002* (2013.01); *A61M 25/0108* (2013.01); *A61N 1/362* (2013.01)

(58) Field of Classification Search
CPC .... A61B 2018/0016; A61B 2018/0022; A61B 2018/0025; A61B 2018/00267; A61B 2018/00351; A61B 2018/00357; A61B 2018/00375; A61B 2018/00577; A61B 2018/00613; A61B 2018/00839; A61B 2018/00988; A61B 2018/1266; A61B 2018/1407; A61B 2018/1435; A61B 2018/1467; A61B 2090/3966; A61B 2218/002; A61M 25/0108; A61N 1/056; A61N 1/327; A61N 1/362; A61N 1/371
See application file for complete search history.

(56) References Cited

U.S. PATENT DOCUMENTS

| | | | |
|---|---|---|---|
| 4,739,759 A | 4/1988 | Rexroth et al. | |
| 5,234,004 A | 8/1993 | Hascoet et al. | |
| 5,242,441 A | 9/1993 | Avitall | |
| 5,257,635 A | 11/1993 | Langberg | |
| 5,281,213 A | 1/1994 | Milder et al. | |
| 5,304,214 A | 4/1994 | DeFord et al. | |
| 5,306,296 A | 4/1994 | Wright et al. | |
| 5,334,193 A | 8/1994 | Nardella | |
| 5,341,807 A | 8/1994 | Nardella | |
| 5,342,301 A | 8/1994 | Saab | |
| 5,398,683 A | 3/1995 | Edwards et al. | |
| 5,443,463 A | 8/1995 | Stern et al. | |
| 5,454,370 A | 10/1995 | Avitall | |
| 5,515,848 A | 5/1996 | Corbett, III et al. | |
| 5,531,685 A | 7/1996 | Hemmer et al. | |
| 5,545,161 A | 8/1996 | Imran | |
| 5,578,040 A | 11/1996 | Smith | |
| 5,617,854 A | 4/1997 | Munsif | |
| 5,624,430 A | 4/1997 | Eton et al. | |
| 5,667,491 A | 9/1997 | Pliquett et al. | |
| 5,672,170 A | 9/1997 | Cho | |
| 5,700,243 A | 12/1997 | Narciso, Jr. | |
| 5,702,438 A * | 12/1997 | Avitall | A61B 18/1492 600/374 |
| 5,706,823 A | 1/1998 | Wodlinger | |
| 5,722,400 A | 3/1998 | Ockuly et al. | |
| 5,722,402 A * | 3/1998 | Swanson | A61B 5/0422 600/374 |
| 5,749,914 A | 5/1998 | Janssen | |
| 5,779,699 A | 7/1998 | Lipson | |
| 5,788,692 A | 8/1998 | Campbell et al. | |
| 5,810,762 A | 9/1998 | Hofmann | |
| 5,833,710 A | 11/1998 | Jacobson | |
| 5,836,874 A | 11/1998 | Swanson et al. | |
| 5,836,942 A | 11/1998 | Netherly et al. | |
| 5,836,947 A | 11/1998 | Fleischman et al. | |
| 5,843,154 A | 12/1998 | Osypka | |
| 5,849,028 A | 12/1998 | Chen | |
| 5,860,974 A | 1/1999 | Abele | |
| 5,863,291 A | 1/1999 | Schaer | |
| 5,868,736 A | 2/1999 | Swanson et al. | |
| 5,871,523 A | 2/1999 | Fleischman et al. | |
| 5,876,336 A | 3/1999 | Swanson et al. | |
| 5,885,278 A | 3/1999 | Fleischman et al. | |
| 5,895,404 A | 4/1999 | Ruiz | |
| 5,899,917 A | 5/1999 | Edwards et al. | |
| 5,904,709 A | 5/1999 | Arndt et al. | |
| 5,916,158 A | 6/1999 | Webster, Jr. | |
| 5,916,213 A * | 6/1999 | Haissaguerre | A61B 18/08 600/374 |
| 5,921,924 A | 7/1999 | Avitall | |
| 5,928,269 A | 7/1999 | Alt | |
| 5,928,270 A | 7/1999 | Ramsey, III | |
| 5,938,660 A | 8/1999 | Swartz et al. | |
| 6,002,955 A | 12/1999 | Willems et al. | |
| 6,006,131 A | 12/1999 | Cooper et al. | |
| 6,009,351 A | 12/1999 | Flachman | |
| 6,014,579 A | 1/2000 | Pomeranz et al. | |
| 6,029,671 A | 2/2000 | Stevens et al. | |
| 6,033,403 A | 3/2000 | Tu et al. | |
| 6,035,238 A | 3/2000 | Ingle et al. | |
| 6,045,550 A | 4/2000 | Simpson et al. | |
| 6,068,653 A | 5/2000 | LaFontaine | |
| 6,071,274 A * | 6/2000 | Thompson | A61B 18/1492 604/528 |
| 6,071,281 A | 6/2000 | Burnside et al. | |
| 6,074,389 A | 6/2000 | Levine et al. | |
| 6,076,012 A | 6/2000 | Swanson et al. | |
| 6,090,104 A | 7/2000 | Webster, Jr. | |
| 6,096,036 A | 8/2000 | Bowe et al. | |
| 6,113,595 A | 9/2000 | Muntermann | |
| 6,119,041 A | 9/2000 | Pomeranz et al. | |
| 6,120,500 A | 9/2000 | Bednarek et al. | |
| 6,142,993 A | 11/2000 | Whayne et al. | |
| 6,146,381 A | 11/2000 | Bowe et al. | |
| 6,164,283 A | 12/2000 | Lesh | |
| 6,167,291 A | 12/2000 | Barajas et al. | |
| 6,171,305 B1 | 1/2001 | Sherman | |
| 6,216,034 B1 | 4/2001 | Hofmann et al. | |
| 6,219,582 B1 | 4/2001 | Hofstad et al. | |
| 6,223,085 B1 | 4/2001 | Dann et al. | |
| 6,231,518 B1 | 5/2001 | Grabek et al. | |
| 6,245,064 B1 | 6/2001 | Lesh et al. | |
| 6,251,107 B1 | 6/2001 | Schaer | |
| 6,251,109 B1 | 6/2001 | Hasset et al. | |
| 6,251,128 B1 | 6/2001 | Knopp et al. | |
| 6,270,476 B1 | 8/2001 | Santoianni et al. | |
| 6,272,384 B1 | 8/2001 | Simon et al. | |
| 6,287,306 B1 | 9/2001 | Kroll et al. | |
| 6,314,963 B1 | 11/2001 | Vaska et al. | |
| 6,322,559 B1 | 11/2001 | Daulton et al. | |
| 6,350,263 B1 | 2/2002 | Wetzig et al. | |
| 6,370,412 B1 | 4/2002 | Armoundas et al. | |
| 6,391,024 B1 | 5/2002 | Sun et al. | |

(56) References Cited

U.S. PATENT DOCUMENTS

| | | |
|---|---|---|
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,613,046 B1 | 9/2003 | Jenkins et al. |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 * | 8/2005 | Sra ................. A61B 18/1492 606/41 |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 | 11/2010 | Abboud et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harley et al. |
| 8,449,535 B2 | 5/2013 | Deno et al. |
| 8,454,594 B2 | 6/2013 | Demarais et al. |
| 8,463,368 B2 | 6/2013 | Harley et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 8,996,091 B2 | 3/2015 | de la Rama et al. |
| 9,002,442 B2 | 4/2015 | Harley et al. |
| 9,005,189 B2 | 4/2015 | Davalos et al. |
| 9,005,194 B2 | 4/2015 | Oral et al. |

(56) References Cited

U.S. PATENT DOCUMENTS

| | | |
|---|---|---|
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,351,789 B2 | 5/2016 | Novichenok et al. |
| 9,375,268 B2 | 6/2016 | Long |
| 9,387,031 B2 | 7/2016 | Stewart et al. |
| 9,414,881 B2 | 8/2016 | Callas et al. |
| 9,468,495 B2 | 10/2016 | Kunis et al. |
| 9,474,486 B2 * | 10/2016 | Eliason ............... A61B 5/6858 |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,510,888 B2 | 12/2016 | Lalonde |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,801,681 B2 | 10/2017 | Laske et al. |
| 9,808,304 B2 | 11/2017 | Lalonde |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,010,368 B2 | 7/2018 | Laske et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,194,818 B2 | 2/2019 | Williams et al. |
| 10,285,755 B2 | 5/2019 | Stewart et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |

(56) References Cited

U.S. PATENT DOCUMENTS

| | | |
|---|---|---|
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |

(56) References Cited

U.S. PATENT DOCUMENTS

| | | |
|---|---|---|
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1* | 12/2015 | Prutchi ............ A61B 18/1492 606/41 |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0249972 A1 | 9/2016 | Klink |
| 2016/0256682 A1 | 9/2016 | Paul et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151014 A1 | 6/2017 | Perfler |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0046791 A1 | 2/2019 | Ebbers et al. |
| 2019/0069950 A1 | 3/2019 | Viswanathan et al. |
| 2019/0076179 A1 | 3/2019 | Babkin et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelsen |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |

(56) References Cited

FOREIGN PATENT DOCUMENTS

| | | |
|---|---|---|
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/201504 | 11/2017 |
| WO | WO 2017/218734 | 12/2017 |
| WO | WO 2018/005511 | 1/2018 |
| WO | WO 2018/106569 | 6/2018 |
| WO | WO 2018/200800 | 11/2018 |
| WO | WO 2019/023259 | 1/2019 |
| WO | WO 2019/023280 | 1/2019 |
| WO | WO 2019/035071 | 2/2019 |
| WO | WO 2019/133606 | 7/2019 |
| WO | WO 2019/133608 | 7/2019 |
| WO | WO 2019/136218 | 7/2019 |
| WO | WO 2019/181612 | 9/2019 |
| WO | WO 2019/234133 | 12/2019 |

OTHER PUBLICATIONS

Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
First Office Action for Chinese Application No. 201580006848.8, dated Jan. 29, 2018, 15 pages.
Office Action for U.S. Appl. No. 15/201,997, dated Dec. 17, 2018, 17 pages.
International Search Report and Written Opinion for International Application No. PCT/US2018/050660, dated Nov. 26, 2018, 13 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
International Search Report and Written Opinion for International Application No. PCT/US2015/010138, dated Mar. 26, 2015, 14 pages.
International Preliminary Report on Patentability for International Application No. PCT/US2015/010138, dated Jul. 12, 2016, 9 pages.
Supplementary European Search Report for European Application No. 15733297.4, dated Aug. 10, 2017, 7 pages.
Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Jul. 12, 2018, 12 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
International Search Report and Written Opinion for International Application No. PCT/US2015/029734, dated Nov. 24, 2015, 15 pages.
Office Action for U.S. Appl. No. 15/795,062, dated Dec. 19, 2017, 14 pages.
Office Action for U.S. Appl. No. 15/795,062, dated Apr. 9, 2018, 20 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.

(56) References Cited

OTHER PUBLICATIONS

Extended European Search Report for European Application No. 15849844.4, dated May 3, 2018, 8 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
International Search Report and Written Opinion for International Application No. PCT/US2015/035582, dated Oct. 2, 2015, 17 pages.
Extended European Search Report for European Application No. 15806278.6, dated Feb. 9, 2018, 5 pages.
International Search Report and Written Opinion for International Application No. PCT/US2015/035592, dated Oct. 2, 2015, 13 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
International Search Report and Written Opinion for International Application No. PCT/US2017/012099, dated May 18, 2017, 17 pages.
Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Office Action for U.S. Appl. No. 15/970,404, dated Oct. 9, 2018, 21 pages.
du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," the Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).

Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for Canadian Application No. 2,881,462, dated Mar. 19, 2019, 5 pages.
Office Action for Japanese Application No. 2018-036714, dated Jan. 16, 2019, 8 pages.
Office Action for U.S. Appl. No. 15/201,983, dated Apr. 3, 2019, 16 pages.
Office Action for U.S. Appl. No. 15/341,523, dated Jan. 29, 2019, 10 pages.
Office Action for U.S. Appl. No. 15/795,075, dated Apr. 10, 2019, 11 pages.
Office Action for U.S. Appl. No. 15/672,916, dated Apr. 9, 2019, 31 pages.
Partial European Search Report for European Application No. 18170210.1, dated Feb. 14, 2019, 13 pages.
Office Action for U.S. Appl. No. 15/970,404, dated Apr. 12, 2019, 20 pages.
Office Action for U.S. Appl. No. 15/917,194, dated Apr. 29, 2019, 10 pages.
Office Action for U.S. Appl. No. 15/795,062, dated May 3, 2019, 21 pages.
International Search Report and Written Opinion for International Application No. PCT/US2019/014226, dated Apr. 29, 2019, 15 pages.
Extended European Search Report for European Application No. 18189811.5, dated May 14, 2019, 7 pages.
International Search Report and Written Opinion for International Application No. PCT/US2019/017322, dated May 10, 2019, 15 pages.
Office Action for U.S. Appl. No. 15/341,512, dated Aug. 1, 2019, 19 pages.
Office Action for U.S. Appl. No. 15/341,523, dated Jul. 30, 2019, 8 pages.
Office Action for U.S. Appl. No. 15/795,075, dated Jul. 31, 2019, 12 pages.
Office Action for U.S. Appl. No. 15/484,969, dated Sep. 4, 2019, 12 pages.
Office Action for U.S. Appl. No. 15/354,475, dated May 23, 2019, 7 pages.
Extended European Search Report for European Application No. 16884132.8, dated Jul. 8, 2019, 7 pages.
Office Action for U.S. Appl. No. 16/416,677, dated Aug. 15, 2019, 8 pages.
Extended European Search Report for European Application No. 17736218.3 dated Aug. 23, 2019, 9 pages.
Office Action for U.S. Appl. No. 16/181,027, dated Sep. 4, 2019, 12 pages.
Office Action for U.S. Appl. No. 16/240,066, dated May 29, 2019, 7 pages.
Extended European Search Report for European Application No. 18170210.1, dated May 17, 2019, 11 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.

(56) References Cited

OTHER PUBLICATIONS

Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
International Search Report and Written Opinion for International Application No. PCT/US2019/028943, dated Sep. 17, 2019, 17 pages.
Office Action for U.S. Appl. No. 15/201,983, dated Nov. 15, 2019, 15 pages.
Office Action for U.S. Appl. No. 15/341,512, dated Nov. 12, 2019, 18 pages.
Office Action for U.S. Appl. No. 15/795,062, dated Nov. 4, 2019, 23 pages.
Office Action for U.S. Appl. No. 16/375,561, dated Oct. 17, 2019, 15 pages.
Office Action for U.S. Appl. No. 15/970,404, dated Nov. 12, 2019, 19 pages.
International Search Report and Written Opinion for International Application No. PCT/US2019/051998, dated Feb. 26, 2020, 11 pages.
International Search Report and Written Opinion for International Application No. PCT/US2020/026682, dated Jun. 16, 2020, 10 pages.

\* cited by examiner

SCALE: 1:2

SYSTEMS, DEVICES, AND METHODS FOR DELIVERY OF PULSED ELECTRIC FIELD ABLATIVE ENERGY TO ENDOCARDIAL TISSUE

CROSS-REFERENCE TO RELATED APPLICATIONS

This application is a continuation of U.S. patent application Ser. No. 16/240,066, titled "SYSTEMS, DEVICES AND METHODS FOR DELIVERY OF PULSED ELECTRIC FIELD ABLATIVE ENERGY TO ENDOCARDIAL TISSUE," filed Jan. 4, 2019, now issued as U.S. Pat. No. 10,433,908, which is a continuation of U.S. patent application Ser. No. 15/711,266, titled "SYSTEMS, DEVICES AND METHODS FOR DELIVERY OF PULSED ELECTRIC FIELD ABLATIVE ENERGY TO ENDOCARDIAL TISSUE," filed Sep. 21, 2017, now issued as U.S. Pat. No. 10,172,673, which is a continuation-in-part of PCT Application No. PCT/US2017/012099, titled "SYSTEMS, DEVICES AND METHODS FOR DELIVERY OF PULSED ELECTRIC FIELD ABLATIVE ENERGY TO ENDOCARDIAL TISSUE," filed Jan. 4, 2017, which claims priority to U.S. Provisional Application No. 62/274,943, titled "SYSTEMS, APPARATUSES AND DEVICES FOR DELIVERY OF PULSED ELECTRIC FIELD ABLATIVE ENERGY TO ENDOCARDIAL TISSUE," filed Jan. 5, 2016. U.S. patent application Ser. No. 15/711,266 also claims priority to U.S. Provisional Application No. 62/491,910, titled "SYSTEMS, DEVICES, AND METHODS FOR DELIVERY OF PULSED ELECTRIC FIELD ABLATIVE ENERGY TO ENDOCARDIAL TISSUE," filed Apr. 28, 2017, and to U.S. Provisional Application No. 62/529,268, titled "SYSTEMS, DEVICES, AND METHODS FOR FOCAL ABLATION," filed Jul. 6, 2017. The entire disclosure of each of the foregoing applications is incorporated herein by reference in its entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high DC voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death). Subsequently, the surrounding tissue may heal naturally.

While pulsed DC voltages may drive electroporation under the right circumstances, there remains an unmet need for thin, flexible, atraumatic devices that effectively deliver high DC voltage electroporation ablation therapy selectively to endocardial tissue in regions of interest while minimizing damage to healthy tissue.

SUMMARY

Described here are systems, devices, and methods for ablating tissue through irreversible electroporation. Generally, a system for delivering a pulse waveform to tissue may include a signal generator configured for generating a pulse waveform and an ablation device coupled to the signal generator and configured to receive the pulse waveform. The ablation device may include a set of splines. The ablation device may be configured for delivering the pulse waveform to tissue during use via one or more spline of the set of splines. Each spline may include a set of jointly wired, or in some cases independently addressable electrodes formed on a surface of the spline. Each electrode of the set of electrodes may have an insulated electrical lead associated therewith. The insulated electrical leads may be disposed in a body of the spline. As used herein, the terms "spline" and "spine" may be used interchangeably.

Described here are systems, devices, and methods for ablating tissue through irreversible electroporation. Generally, a system for delivering a pulse waveform to tissue may include a signal generator configured for generating a pulse waveform and an ablation device coupled to the signal generator and configured to receive the pulse waveform. The ablation device may include a set of splines. The ablation device may be configured for delivering the pulse waveform to tissue during use via one or more spline of the set of splines. Each spline may include a set of jointly wired, or in some cases independently addressable electrodes formed on a surface of the spline. Each electrode of the set of electrodes may have an insulated electrical lead associated therewith. The insulated electrical leads may be disposed in a body of the spline. As used herein, the terms "spline" and "spine" may be used interchangeably In some embodiments, an apparatus may include a catheter shaft defining a longitudinal axis and a shaft lumen therethrough. A set of splines may extend from a distal end of the shaft lumen. Each spline of the set of splines may include a set of electrodes formed on a surface of that spline. A distal cap may be coupled to a distal portion of each spline of the set of splines. The set of splines may be configured for translation along the longitudinal axis to transition between a first configuration and a second configuration. The first configuration may include the distal cap coupled to a distal end of the catheter shaft at a first distance and the second configuration may include the distal cap coupled to the distal end of the catheter shaft at a second distance. A ratio of the first distance to the second distance is between about 5:1 and about 25:1.

In some embodiments, an apparatus may include a catheter shaft defining a longitudinal axis and a shaft lumen therethrough. A set of splines may extend from a distal end of the shaft lumen. Each spline of the set of splines may include a set of electrodes formed on a surface of that spline. A distal cap may be coupled to a distal portion of each spline of the set of splines. The set of splines may be configured for translation along the longitudinal axis to transition between a first configuration and a second configuration. In the first configuration, each spline may lie in a cylindrical plane that is generally parallel to the longitudinal axis of the catheter shaft. In the second configuration, at least a portion of each spline of the set of splines may have a radius of curvature between about 7 mm and about 25 mm.

In some embodiments, an apparatus may include a catheter shaft defining a longitudinal axis and a shaft lumen therethrough. A set of splines may extend from a distal end of the shaft lumen. Each spline of the set of splines may include a set of electrodes formed on a surface of that spline. A distal cap may be coupled to a distal portion of each spline of the set of splines. The set of splines may be configured for translation along the longitudinal axis to transition between a first configuration and a second configuration. In the first configuration, each spline may lie in a cylindrical plane that is generally parallel to the longitudinal axis of the catheter shaft. In the second configuration, each spline may form a loop having a first concave curve facing the distal cap, a second concave curve facing the longitudinal axis, and a third concave curve facing the distal end of the shaft lumen.

In some embodiments, the first configuration may include the set of splines arranged to helically rotate about the longitudinal axis. Each spline of the set of splines may have a non-zero helix angle of less than about 5 degrees. Each spline of the set of splines may have a non-zero helix angle of less than about 2 degrees. Each spline of the set of splines may have a non-zero helix angle of less than about 1 degree.

In some embodiments, the set of splines in the second configuration may be arranged as a set of non-overlapping loops. The set of splines in the second configuration may be arranged as a set of electrically isolated loops. The set of splines in the second configuration may include a radius of curvature that varies along a spline length. The set of splines in the second configuration may be configured to abut a tissue wall. The set of electrodes on at least two of the splines may be configured to generate an electric field comprising a magnitude and a tangential component of the electric field lines relative to the tissue wall. The tangential component may be greater than half of the magnitude in a substantial portion of the tissue wall between the at least two splines. Each spline of the set of splines in the second configuration may bias away from the longitudinal axis by up to about 30 mm. The set of splines in the second configuration may have a diameter between about 10 mm and about 50 mm. The set of splines in the second configuration may have a diameter between about 25 mm and about 35 mm. The set of splines in the second configuration may have a diameter of about 30 mm. The set of splines and the distal cap may be configured for translation together along the longitudinal axis by up to about 60 mm. Each of the distal portions of the set of splines may be fixed to the distal cap.

In some embodiments, each spline of the set of splines in the second configuration may include an approximately elliptical or oval cross-section. The elliptical cross-section may include a major axis length between about 1 mm and about 2.5 mm and a minor axis length between about 0.4 mm and about 1.2 mm. In some embodiments, the set of splines may include between 3 splines and 20 splines. The set of splines may include a 5 splines. The set of splines may include 8 splines. Each spline of the set of splines may have a cross-sectional area between about 0.2 $mm^2$ and about 15 $mm^2$.

In some embodiments, each spline of the set of splines defines a spline lumen therethrough. The set of electrodes of the set of splines may include an insulated electrical lead associated therewith. The insulated electrical leads may be disposed in the spline lumen of each spline of the set of splines. The insulated electrical leads may be configured for sustaining a voltage potential of at least about 700 V without dielectric breakdown of its corresponding insulation. The set of electrodes for each spline in the set of splines may include at least one electrode configured for ablation and at least one electrode configured for receiving an ECG signal. At least one electrode may be configured for ablation and at least one electrode configured for receiving the ECG signal may be coupled to separate insulated electrical leads. The set of electrodes may include four electrodes configured for ablation and one electrode configured for receiving the ECG signal The set of electrodes for each spline in the set of splines may be coupled to a corresponding insulated electrical lead. Each spline of the set of splines in the second configuration may include an apex relative to the longitudinal axis. The set of electrodes may be unequally distributed with respect to the apex of each spline of the set of splines. The set of electrodes may be distributed proximal and distal to the apex by a ratio of 1 to 3. The set of electrodes may be distributed proximal and distal to the apex by a ratio of 1 to 2. The set of electrodes may be distributed proximal and distal to the apex by a ratio of 2 to 3. The set of electrodes for each spline may be jointly wired. The set of electrodes for each spline may be wired in series. The set of electrodes may include an atraumatic shape.

In some embodiments, the set of electrodes may include an elliptical cross-section. The elliptical cross-section may include a major axis length between about 1 mm and about 4 mm and a minor axis length between about 0.4 mm and about 3 mm. The set of electrodes may include from 2 electrodes to 64 electrodes. Each electrode of the set of electrodes may have a surface area between about 0.5 $mm^2$ and about 20 $mm^2$.

In some embodiments, a first set of electrodes of a first spline of the set of splines may be configured as an anode, and a second set of electrodes of a second spline of the set of splines may be configured as a cathode. The first spline may be non-adjacent to the second spline. The first set of electrodes may include one electrode and the second set of electrodes may include at least two electrodes. One electrode of each spline of the set of splines may be alternatively configured for ablation and for receiving ECG signals. A distance between the distal cap and the catheter shaft may be less than about 8 mm.

In some embodiments, the distal cap may include an atraumatic shape. The distal cap may define a cap lumen therethrough. A diameter of the catheter shaft may be between about 6 French and about 15 French. One or more of a distal portion of the catheter shaft and distal cap may include a radiopaque portion. The set of splines may include a radiopaque portion formed on a surface of the set of splines. The catheter shaft may include a length between about 60 cm and about 85 cm.

In some embodiments, an apparatus may include a handle and a catheter shaft coupled to a proximal end of the handle. The catheter shaft may define a longitudinal axis and a shaft lumen therethrough. A set of splines may extending from a distal end of the shaft lumen. Each spline of the set of splines may include a set of electrodes formed on a surface of that spline. A distal cap may be coupled to a distal portion of each spline of the set of splines. The set of splines may be configured for translation along the longitudinal axis to transition between a first configuration and a second configuration. The first configuration may include the distal cap coupled to a distal end of the catheter shaft at a first distance and the second configuration may include the distal cap coupled to the distal end of the catheter shaft at a second distance. A ratio of the first distance to the second distance may be between about 5:1 and about 25:1.

In some embodiments, the handle may be coupled to the set of splines and the distal cap. The handle may define a second longitudinal axis and a handle lumen therethrough. The handle may include a translation member disposed in the handle lumen. The translation member may be configured for translation along the second longitudinal axis to transition the set of splines between the first configuration and the second configuration. The translation member may be configured for rotation about the second longitudinal axis to transition between a lock configuration and an unlock configuration. The lock configuration may fix a translational position of the set of splines and the distal cap relative to the catheter shaft and the unlock configuration may permit translation of the set of splines and the distal cap relative to the catheter shaft. The translation member may include a locking member. The locking member may include a protrusion.

The handle lumen may define a translation groove and a plurality of locking grooves each intersecting the translation groove. The locking member may be configured for translation along the translation groove to transition the set of splines between the first configuration and the second configuration. An electrical cable may be coupled to the handle. A proximal end of the electrical cable may include one or more connectors. The translation member may define a guidewire lumen therethrough. The handle may include a flush port.

In some embodiments, a system may include a signal generator configured for generating a pulse waveform and a cardiac stimulator coupled to the signal generator and configured for generating a pacing signal for cardiac stimulation during use, and for transmitting an indication of the pacing signal to the signal generator. The signal generator may be further configured for generating the pulse waveform in synchronization with the indication of the pacing signal. An ablation device may be coupled to the signal generator and configured for receiving the pulse waveform. The ablation device may include a handle and a catheter shaft coupled to a proximal end of the handle. The catheter shaft may define a first longitudinal axis and a shaft lumen therethrough. A set of splines may be coupled to the catheter shaft. A distal portion of each spline of the set of splines may extend distally from a distal end of the catheter shaft. Each spline of the set of splines may include a set of electrodes formed on a surface of each spline of the set of splines. A distal cap may be coupled to the distal portions of each spline of the set of splines. The distal portions may each include a helical shape about the first longitudinal axis. The handle may be configured for translating the set of splines along the first longitudinal axis to transition the set of splines between a first configuration and a second configuration. The first configuration may include the set of splines arranged substantially parallel to the first longitudinal axis and the second configuration may include the set of splines arranged substantially perpendicular to the first longitudinal axis.

In some embodiments, the system may include a guidewire. The ablation device may be configured for being disposed over the guidewire during use. A deflectable sheath may be configured for deflecting at least about 180 degrees. A dilator may be configured for dilating a transseptal opening. The dilator may be configured for creating the transseptal opening. An extension cable may be configured for electrically coupling the electrodes of the set of splines to the signal generator. A diagnostic device may be configured for receiving electrophysiology data of a left atrium. The electrophysiology data may include at least one pulmonary vein of the left atrium. The signal generator may be configured for generating the pulse waveform with a time offset with respect to the indication of the pacing signal.

In some embodiments, the pulse waveform may include a first level of a hierarchy of the pulse waveform includes a first set of pulses, each pulse having a pulse time duration, a first time interval separating successive pulses. A second level of the hierarchy of the pulse waveform may include a plurality of first sets of pulses as a second set of pulses, a second time interval separating successive first sets of pulses, the second time interval being at least three times the duration of the first time interval. A third level of the hierarchy of the pulse waveform may include a plurality of second sets of pulses as a third set of pulses, a third time interval separating successive second sets of pulses, the third time interval being at least thirty times the duration of the second level time interval.

In some embodiments, a method of treating atrial fibrillation via irreversible electroporation may include creating a transseptal opening into a left atrium, advancing a guidewire and a sheath into the left atrium through the transseptal opening, and advancing an ablation device into the left atrium over the guidewire. The ablation device may include a catheter shaft defining a longitudinal axis and a shaft lumen therethrough. A set of splines may be coupled to the catheter shaft. A distal portion of each spline of the set of splines may extend distally from a distal end of the catheter shaft. Each spline of the set of splines may include a set of electrodes formed on a surface of each spline of the set of splines. The set of splines may be configured for translation along the longitudinal axis to transition between a first configuration and a second configuration. The first configuration may include the set of splines arranged substantially parallel to the longitudinal axis and the second configuration may include the set of splines arranged substantially perpendicular to the longitudinal axis. The method may further include the steps of transitioning the ablation device from the first configuration into the second configuration, recording first electrophysiology data of the left atrium, advancing the ablation device to toward a pulmonary vein of a set of pulmonary veins, delivering a pulse waveform to the pulmonary vein using the ablation device, recording second electrophysiology data of the left atrium after delivering the pulse waveform.

In some embodiments, the ablation device may be configured to generate a set of circumferential electric field lines generally parallel with a second longitudinal axis of a set of myocardial cells disposed circumferentially in an atrial wall when delivering the pulse waveform. A first access site may be created in a patient. The guidewire may be advanced through the first access site and into a right atrium. The dilator and a sheath may be advanced over the guidewire and into the right atrium. The dilator may be advanced from the right atrium into the left atrium through an interatrial septum to create the transseptal opening. The transseptal opening may be dilated using the dilator.

In some embodiments, the method may include creating a second access site in the patient for advancing a cardiac stimulator. The cardiac stimulator may be advanced into a right ventricle. A pacing signal for cardiac stimulation of the heart may be generated using the cardiac stimulator. The pacing signal may be applied to the heart using the cardiac stimulator. The pulse waveform may be generated in synchronization with the pacing signal.

In some embodiments, the first and second electrophysiology data may include intracardiac ECG signal data of at least one pulmonary vein. The first and second electrophysiology data may be recorded using the ablation device in the second configuration. A diagnostic catheter may be advanced into the left atrium and may record the first and second electrophysiology data using the diagnostic catheter. The diagnostic catheter may be advanced through a jugular vein. The ablation device disposed in the left atrium may transition from the first configuration into the second configuration without contacting an atrial wall and the pulmonary vein. The ablation device may be disposed in an endocardial space of the left atrium. The ablation device may be in contact with a pulmonary vein antrum. The set of splines may be in contact with the pulmonary vein ostium and form a "C" shape.

In some embodiments, a first set of electrodes of a first spline of the set of splines may be configured as an anode, and a second set of electrodes of a second spline of the set of splines may be configured as a cathode. The first spline may be non-adjacent to the second spline. The first set of electrodes may include one electrode and the second set of electrodes may include at least two electrodes. A radiopaque portion of the ablation device may be fluoroscopically imaged during one or more steps.

In some embodiments, the first access site may be a femoral vein. The interatrial septum may include a fossa ovalis. The pulse waveform may be generated using a signal generator coupled to the ablation device. The set of splines may be transitioned from the second configuration after ablation of the pulmonary vein, and the ablation device may be advanced to another pulmonary vein of the set of pulmonary veins.

In some embodiments, the pulse waveform may include a first level of a hierarchy of the pulse waveform including a first set of pulses, each pulse having a pulse time duration, a first time interval separating successive pulses. A second level of the hierarchy of the pulse waveform may include a plurality of first sets of pulses as a second set of pulses, a second time interval separating successive first sets of pulses, the second time interval being at least three times the duration of the first time interval. A third level of the hierarchy of the pulse waveform may include a plurality of second sets of pulses as a third set of pulses, a third time interval separating successive second sets of pulses, the third time interval being at least thirty times the duration of the second level time interval. The pulse waveform may include a time offset with respect to the pacing signal.

In some embodiments, the ablation device may include a handle, the catheter shaft coupled to a proximal end of the handle. The method may include translating the set of splines along the first longitudinal axis to transition the set of splines between the first configuration and the second configuration using the handle. The handle may be rotated to transition the ablation device between a lock configuration and an unlock configuration.

In some embodiments, the lock configuration may fix a translational position of the set of splines relative to the catheter shaft and the unlock configuration may permit translation of the set of splines relative to the catheter shaft. A signal generator may be electrically coupled to the proximal end of the handle. The signal generator may be electrically coupled to the proximal end of the handle using an extension cable. The pulse waveform may be between about 500 V and about 3,000 V. The set of splines in the second configuration may be visually confirmed as not in contact with the pulmonary vein. An antral apposition of the set of splines in contact with the pulmonary vein may be visually confirmed. In some embodiments, a first set of electrodes of a first spline of the set of splines may be configured as anodes. A second set of electrodes of a second spline of the set of splines may be configured as cathodes. The pulse waveform may be delivered to the first set of electrodes and the second set of electrodes.

In some embodiments, an ablation device deployed in the second configuration may appose tissue (e.g., an atrial surface) such that one or more electrodes formed on each surface of at least two splines may be suitably polarized to generate an electric field in atrial tissue. The electric field may have a field direction that is generally aligned in a circumferential direction of the atrial tissue. This circumferential alignment of the electric field with tissue may enhance the safety, efficiency and effectiveness of irreversible electroporation to tissue and yield more effective ablative lesions with a reduction in total energy delivered.

BRIEF DESCRIPTION OF THE DRAWINGS

FIG. 8A is a side view and FIG. 8B is a front cross-sectional view.

FIG. 12A illustrates an unenergized electrode and FIG. 12B illustrates an energized electrode.

FIG. 19A is a schematic perspective view and FIG. 19B is a cross-sectional view.

FIG. 20A is a schematic perspective view and FIG. 20B is a cross-sectional view.

DETAILED DESCRIPTION

Figure 1:
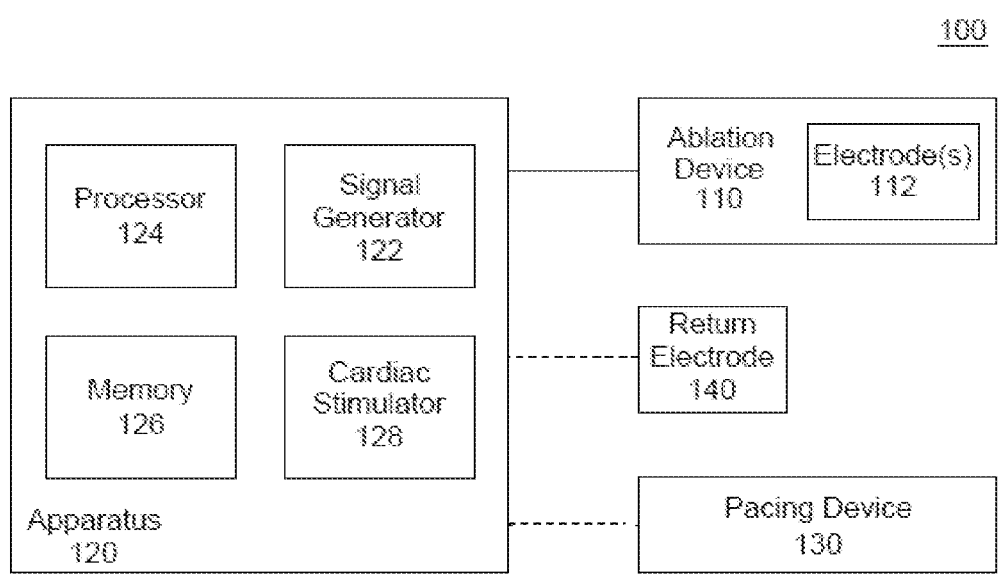
FIG. 1 is a block diagram of an electroporation system, according to embodiments.

Described herein are systems, devices, and methods for selective and rapid application of pulsed electric fields to ablate tissue by irreversible electroporation. Generally, the systems, devices, and methods described herein may be used to generate large electric field magnitudes at desired regions of interest and reduce peak electric field values elsewhere in order to reduce unnecessary tissue damage and electrical arcing. An irreversible electroporation system as described herein may include a signal generator and a processor configured to apply one or more voltage pulse waveforms to a selected set of electrodes of an ablation device to deliver energy to a region of interest (e.g., ablation energy for a set of tissue in a pulmonary vein ostium or antrum). The pulse waveforms disclosed herein may aid in therapeutic treatment of a variety of cardiac arrhythmias (e.g., atrial fibrillation). In order to deliver the pulse waveforms generated by the signal generator, one or more electrodes of the ablation device may have an insulated electrical lead configured for sustaining a voltage potential of at least about 700 V without dielectric breakdown of its corresponding insulation. The electrodes may be independently addressable such that each electrode may be controlled (e.g., deliver energy) independently of any other electrode of the device. In this manner, the electrodes may deliver different energy waveforms with different timing synergistically for electroporation of tissue.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," the contents of which are hereby incorporated by reference in its entirety.

In some embodiments, the systems may further include a cardiac stimulator used to synchronize the generation of the pulse waveform to a paced heartbeat. The cardiac stimulator may electrically pace the heart with a cardiac stimulator and ensure pacing capture to establish periodicity and predictability of the cardiac cycle. A time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. In some embodiments, an ablation device may include one or more catheters, guidewires, balloons, and electrodes. The ablation device may transform into different configurations (e.g., compact and expanded) to position the device within an endocardial space. In some embodiments, the system may optionally include one or more return electrodes.

Generally, to ablate tissue, one or more catheters may be advanced in a minimally invasive fashion through vasculature to a target location. For example, an ablation device may be advanced through vasculature over a guidewire and through a deflectable sheath. The sheath may be configured for deflecting at least about 180 degrees and aid in guiding an ablation catheter through vasculature and one or more predetermined targets (e.g., pulmonary vein ostia). A dilator may be advanced over a guidewire and configured for creating and dilating a transseptal opening during and/or prior to use. In a cardiac application, the electrodes through which the voltage pulse waveform is delivered may be disposed on an epicardial device or on an endocardial device. The methods described here may include introducing a device into an endocardial space of the left atrium of the heart and disposing the device in contact with a pulmonary vein ostium. A pulse waveform may be generated and delivered to one or more electrodes of the device to ablate tissue. In some embodiments, the pulse waveform may be generated in synchronization with a pacing signal of the heart to avoid disruption of the sinus rhythm of the heart. In some embodiments, the electrodes may be configured in anode-cathode subsets. The pulse waveform may include hierarchical waveforms to aid in tissue ablation and reduce damage to healthy tissue.

I. Systems

Overview

Disclosed herein are systems and devices configured for tissue ablation via the selective and rapid application of voltage pulse waveforms to aid tissue ablation, resulting in irreversible electroporation. Generally, a system for ablating tissue described here may include a signal generator and an ablation device having one or more electrodes for the selective and rapid application of DC voltage to drive electroporation. As described herein, the systems and devices may be deployed epicardially and/or endocardially to treat atrial fibrillation. Voltages may be applied to a selected subset of the electrodes, with independent subset selections for anode and cathode electrode selections. A pacing signal for cardiac stimulation may be generated and used to generate the pulse waveform by the signal generator in synchronization with the pacing signal.

Generally, the systems and devices described herein include one or more catheters configured to ablate tissue in a left atrial chamber of a heart. FIG. 1 illustrates an ablation system (100) configured to deliver voltage pulse waveforms. The system (100) may include an apparatus (120) including a signal generator (122), processor (124), memory (126), and cardiac stimulator (128). The apparatus (120) may be coupled to an ablation device (110), and optionally to a pacing device (130) and/or an optional return electrode (140) (e.g., a return pad, illustrated here with dotted lines).

The signal generator (122) may be configured to generate pulse waveforms for irreversible electroporation of tissue, such as, for example, pulmonary vein ostia. For example, the signal generator (122) may be a voltage pulse waveform generator and deliver a pulse waveform to the ablation device (110). The return electrode (140) may be coupled to a patient (e.g., disposed on a patient's back) to allow current to pass from the ablation device (110) through the patient and then to the return electrode (140) to provide a safe current return path from the patient (not shown). The processor (124) may incorporate data received from memory (126), cardiac stimulator (128), and pacing device (130) to determine the parameters (e.g., amplitude, width, duty cycle, etc.) of the pulse waveform to be generated by the signal generator (122). The memory (126) may further store instructions to cause the signal generator (122) to execute modules, processes and/or functions associated with the system (100), such as pulse waveform generation and/or cardiac pacing synchronization. For example, the memory (126) may be configured to store pulse waveform and/or heart pacing data for pulse waveform generation and/or cardiac pacing, respectively.

In some embodiments, the ablation device (110) may include a catheter configured to receive and/or deliver the pulse waveforms described in more detail below. For example, the ablation device (110) may be introduced into an endocardial space of the left atrium and positioned to align one or more electrodes (112) to one or more pulmonary vein ostial or antral locations, and then deliver the pulse waveforms to ablate tissue. The ablation device (110) may include one or more electrodes (112), which may, in some embodiments, be a set of independently addressable electrodes. Each electrode may include an insulated electrical lead configured to sustain a voltage potential of at least about 700 V without dielectric breakdown of its corresponding insulation. In some embodiments, the insulation on each of the electrical leads may sustain an electrical potential difference of between about 200 V to about 1,500 V across its thickness without dielectric breakdown. For example, the electrodes (112) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like.

The pacing device (130) may be suitably coupled to the patient (not shown) and configured to receive a heart pacing signal generated by the cardiac stimulator (128) of the apparatus (120) for cardiac stimulation. An indication of the pacing signal may be transmitted by the cardiac stimulator (128) to the signal generator (122). Based on the pacing signal, an indication of a voltage pulse waveform may be selected, computed, and/or otherwise identified by the processor (124) and generated by the signal generator (122). In some embodiments, the signal generator (122) is configured to generate the pulse waveform in synchronization with the indication of the pacing signal (e.g., within a common refractory window). For example, in some embodiments, the common refractory window may start substantially immediately following a ventricular pacing signal (or after a very small delay) and last for a duration of approximately 250 ms or less thereafter. In such embodiments, an entire pulse waveform may be delivered within this duration.

In some embodiments, a diagnostic device (e.g., mapping catheter) may be configured for receiving electrophysiology data (e.g., ECG signals) of a heart chamber (e.g., left atrium, left ventricle). Electrophysiology data may be recorded and used to generate an anatomical map that may be used to compare electrophysiology data recorded before and after energy delivery to determine the effectiveness of tissue ablation.

The processor (124) may be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The memory (126) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (126) may store instructions to cause the processor (124) to execute modules, processes and/or functions associated with the system (100), such as pulse waveform generation and/or cardiac pacing.

The system (100) may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution.

Ablation Device

Figure 2:
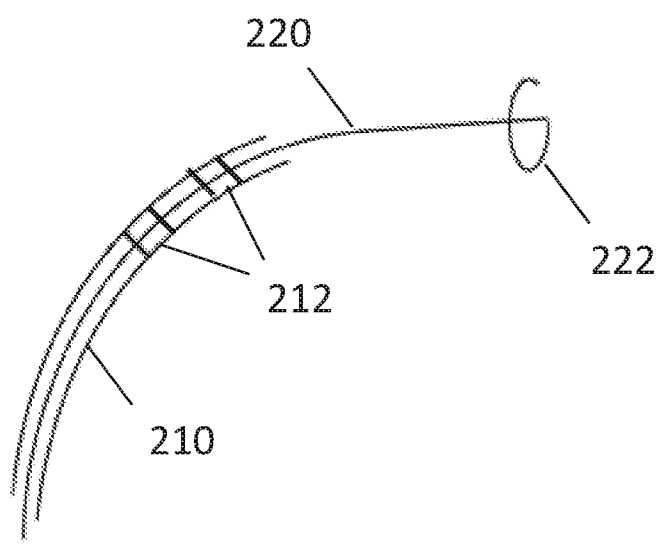
FIG. 2 is a perspective view of an ablation catheter, according to embodiments.

The systems described here may include one or more multi-electrode ablation devices configured to ablate tissue in a left atrial chamber of a heart for treating atrial fibrillation. FIG. 2 is a perspective view of an ablation device (200) (e.g., structurally and/or functionally similar to the ablation device (110)) including a catheter (210) and a guidewire (220) slidable within a lumen of the catheter (210). The guidewire (220) may include a nonlinear distal portion (222) and the catheter (210) may be configured to be disposed over the guidewire (220) during use. The distal portion (222) of the guidewire (220) may be shaped to aid placement of the catheter (210) in a lumen of the patient. For example, a shape of the distal portion (222) of the guidewire (220) may be configured for placement in a pulmonary vein ostium and/or the vicinity thereof, as described in more detail with respect to FIG. 15. The distal portion (222) of the guidewire (220) may include and/or be formed in an atraumatic shape that reduces trauma to tissue (e.g., prevents and/or reduces the possibility of tissue puncture). For example, the distal portion (222) of the guidewire (220) may include a nonlinear shape such as a circle, loop (as illustrated in FIG. 2), ellipsoid, or any other geometric shape. In some embodiments, the guidewire (220) may be configured to be resilient such that the guidewire having a nonlinear shape may conform to a lumen of the catheter (210) when disposed in the catheter (210), and re-form/otherwise regain the nonlinear shape when advanced out of the catheter (210). In other embodiments, the catheter (210) may similarly be configured to be resilient, such as for aiding advancement of the catheter (210) through a sheath (not shown). The shaped distal portion (222) of the guidewire (220) may be angled relative to the other portions of the guidewire (220) and catheter (210). The catheter (210) and guidewire (220) may be sized for advancement into an endocardial space (e.g., left atrium). A diameter of the shaped distal portion (222) of the guidewire (220) may be about the same as a diameter of a lumen in which the catheter (230) is to be disposed.

The catheter (210) may be slidably advanced over the guidewire (220) so as to be disposed over the guidewire (220) during use. The distal portion (222) of the guidewire (220) disposed in a lumen (e.g., near a pulmonary vein ostium) may serve as a backstop to advancement of a distal portion of the catheter (210). The distal portion of the catheter (210) may include a set of electrodes (212) (e.g., structurally and/or functionally similar to the electrode(s) (112)) configured to contact an inner radial surface of a lumen (e.g., pulmonary vein ostium). For example, the electrodes (212) may include an approximately circular arrangement of electrodes configured to contact a pulmonary vein ostium. As shown in FIG. 2, one or more electrodes (212) may include a series of metallic bands or rings disposed along a catheter shaft and be electrically connected together. For example, the ablation device (200) may comprise a single electrode having a plurality of bands, one or more electrodes each having its own band, and combinations thereof. In some embodiments, the electrodes (212) may be shaped to conform to the shape of the distal portion (222) of the guidewire (220). The catheter shaft may include flexible portions between the electrodes to enhance flexibility. In other embodiments, one or more electrodes (212) may include a helical winding to enhance flexibility.

Each of the electrodes of the ablation devices discussed herein may be connected to an insulated electrical lead (not shown) leading to a handle (not shown) coupled to a proximal portion of the catheter. The insulation on each of the electrical leads may sustain an electrical potential difference of at least 700V across its thickness without dielectric breakdown. In other embodiments, the insulation on each of the electrical leads may sustain an electrical potential difference of between about 200 V to about 2,000 V across its thickness without dielectric breakdown, including all values and sub-ranges in between. This allows the electrodes to effectively deliver electrical energy and to ablate tissue through irreversible electroporation. The electrodes may, for example, receive pulse waveforms generated by a signal generator (122) as discussed above with respect to FIG. 1. In other embodiments, a guidewire (220) may be separate from the ablation device (200) (e.g., the ablation device (200) includes the catheter (210) but not the guidewire (220). For example, a guidewire (220) may be advanced by itself into an endocardial space, and thereafter the catheter (210) may be advanced into the endocardial space over the guidewire (220).

Figure 3:
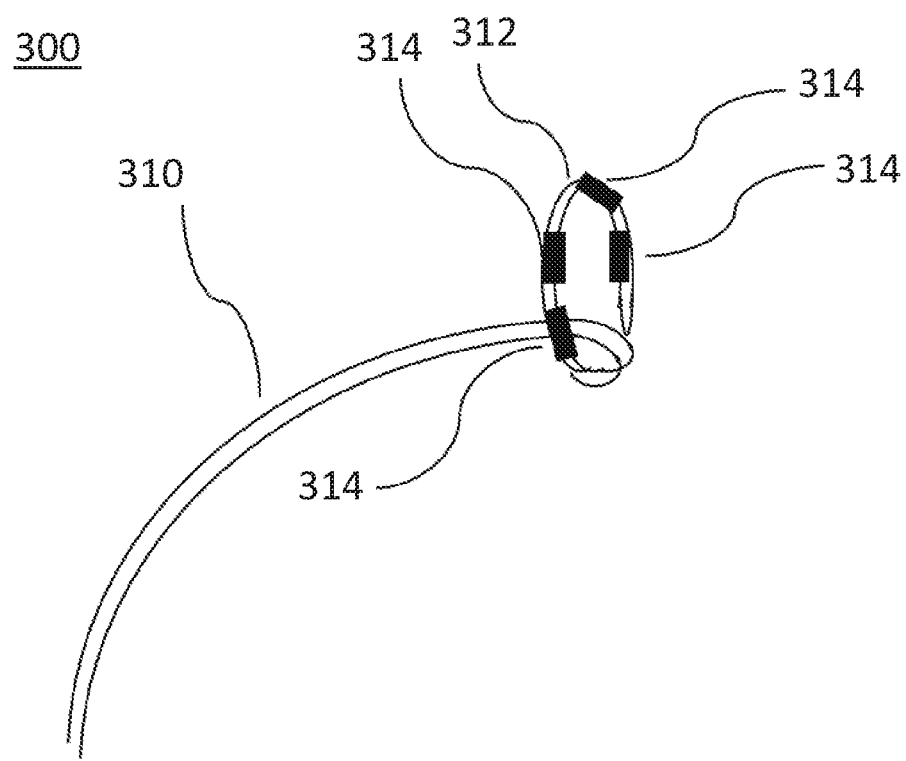
FIG. 3 is a perspective view of an ablation catheter, according to other embodiments.

FIG. 3 is a perspective view of another embodiment of an ablation device (300) (e.g., structurally and/or functionally similar to the ablation device (110)) including a catheter (310) having a set of electrodes (314) provided along a distal portion (312) of the catheter (310). The distal portion (312) of the catheter (310) may be nonlinear and form an approximately circle shape. A set of electrodes (314) may be disposed along a nonlinear distal portion (312) of the catheter (310) may form a generally circular arrangement of electrodes (314). During use, the electrodes (314) may be disposed at a pulmonary vein ostium in order to deliver a pulse waveform to ablate tissue, as described in more detail with respect to FIG. 16. The shaped distal portion (312) of the catheter (310) may be angled relative to the other portions of the catheter (310). For example, the distal portion (312) of the catheter (310) may be generally perpendicular to an adjacent portion of the catheter (310). In some embodiments, a handle (not shown) may be coupled to a proximal portion of the catheter (310) and may include a bending mechanism (e.g., one or more pull wires (not shown)) configured to modify the shape of the distal portion (312) of the catheter (310). For example, operation of a pull wire of the handle may increase or decrease a circumference of the circular shape of the distal portion (312) of the catheter (310). The diameter of the distal portion (312) of the catheter (310) may be modified to allow the electrodes (314) to be disposed near and/or in contact with a pulmonary vein ostium (e.g., in contact with an inner radial surface of the pulmonary vein). The electrodes (314) may include a series of metallic bands or rings and be independently addressable.

In some embodiments, the pulse waveform may be applied between the electrodes (314) configured in anode and cathode sets. For example, adjacent or approximately diametrically opposed electrode pairs may be activated together as an anode-cathode set. It should be appreciated that any of the pulse waveforms disclosed herein may be progressively or sequentially applied over a sequence of anode-cathode electrodes.

Figure 4:
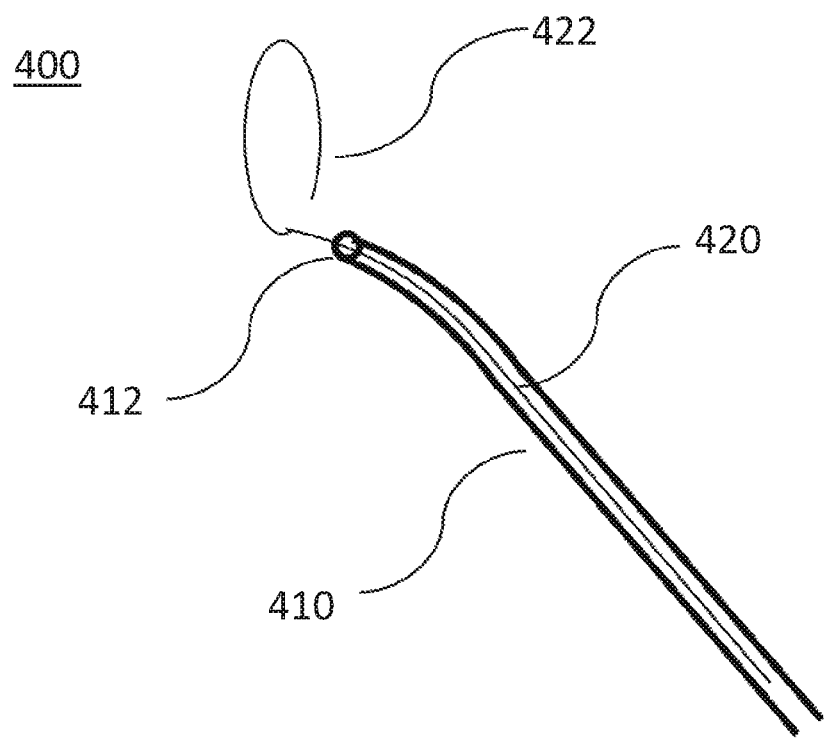
FIG. 4 is a perspective view of an ablation catheter, according to other embodiments.

FIG. 4 is a perspective view of yet another embodiment of an ablation device (400) (e.g., structurally and/or functionally similar to the ablation device (110)) including a catheter (410) and a guidewire (420) having a shaped, nonlinear distal portion (422). The guidewire (420) may be slidable within a lumen of the catheter (410). The guidewire (420) may be advanced through the lumen of the catheter (410) and a distal portion (422) of the guidewire (420) may be approximately circular shaped. The shape and/or diameter of the distal portion (422) of the guidewire (420) may be modified using a bending mechanism as described above with respect to FIG. 3. The catheter (410) may be flexible so as to be deflectable. In some embodiments, the catheter (410) and/or guidewire (420) may be configured to be resilient such that they conform to a lumen in which they are disposed and assume a secondary shape when advanced out of the lumen. By modifying a size of the guidewire (420) and manipulating the deflection of the catheter (410), the distal portion (422) of the guidewire (420) may be positioned at a target tissue site, such as, a pulmonary vein ostium. A distal end (412) of the catheter (410) may be sealed off except where the guidewire (420) extends from such that the catheter (410) may electrically insulate the portion of the guidewire (420) within the lumen of the catheter (410). For example, in some embodiments, the distal end (412) of the catheter (410) may include a seal having an opening that permits passage of the guidewire (420) upon application of force to form a compression hold (that may be fluid-tight) between the seal and the guidewire (420).

In some embodiments, the exposed distal portion (422) of the guidewire (420) may be coupled to an electrode and configured to receive a pulse waveform from a signal generator and deliver the pulse waveform to tissue during use. For example, a proximal end of the guidewire (420) may be coupled to a suitable lead and connected to the signal generator (122) of FIG. 1. The distal portion (422) of the guidewire (420) may be sized such that it may be positioned at a pulmonary vein ostium in some cases, or in other cases at a pulmonary vein antrum. For example, a diameter of the shaped distal portion (422) of the guidewire (420) may be about the same as a diameter of a pulmonary vein ostium. The shaped distal portion (422) of the guidewire (420) may be angled relative to the other portions of the guidewire (420) and catheter (410).

The guidewire (420) may include stainless steel, nitinol, platinum, or other suitable, biocompatible materials. In some embodiments, the distal portion (422) of the guidewire (420) may include a platinum coil physically and electrically attached to the guidewire (420). The platinum coil may be an electrode configured for delivery of a voltage pulse waveform. Platinum is radiopaque and its use may increase flexibility to aid advancement and positioning of the ablation device (400) within an endocardial space.

Figure 5:
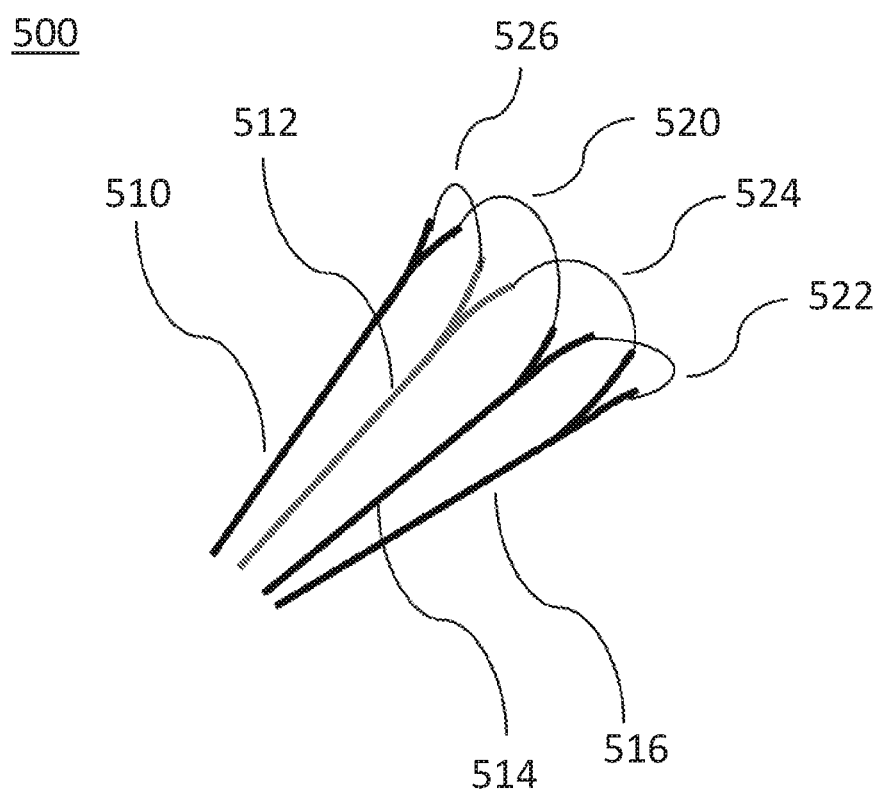
FIG. 5 is a detailed perspective view of a distal portion of an ablation catheter, according to other embodiments.

FIG. 5 is a detailed perspective view of a flower-shaped distal portion of an ablation device (500) (e.g., structurally and/or functionally similar to the ablation device (110)) including a set of electrodes (520, 522, 524, 526) each extending from a pair of insulated lead segments (510, 512, 514, 516). Each pair of adjacent insulated lead segments coupled to an uninsulated electrode (e.g., lead segments (510, 512) and electrode (526)) form a loop (FIG. 5 illustrates a set of four loops). The set of loops at the distal portion of the ablation device (500) may be configured for delivering a pulse waveform to tissue. The ablation device (500) may include a set of insulated lead segments (510, 512, 514, 516) that branch out at a distal end of the device (500) to connect to respective exposed electrodes (520, 522, 524, 526), as shown in FIG. 5. The electrodes (520, 522, 524, 526) may include an exposed portion of an electrical conductor. In some embodiments, one or more of the electrodes (520, 522, 524, 526) may include a platinum coil. The one or more segments (510, 512, 514, 516) may be coupled to a bending mechanism (e.g., strut, pull wire, etc.) controlled from a handle (not shown) to control a size and/or shape of the distal portion of the device (500).

The electrodes (520, 522, 524, 526) may be flexible and form a compact first configuration for advancement into an endocardial space, such as adjacent to a pulmonary vein ostium. Once disposed at a desired location, the electrodes (520, 522, 524, 526) may be transformed to an expanded second configuration when advanced out of a lumen, such as a sheath, to form a flower-shaped distal portion, as shown in FIG. 5. In other embodiments, the insulated lead segments (510, 512, 514, 516) and electrodes (520, 522, 524, 526) may be biased to expand outward (e.g., spring open) into the second configuration when advanced out of a lumen (e.g., sheath) carrying the device (500). The electrodes (520, 522, 524, 526) may be independently addressable and each have an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2,000 V across its thickness without dielectric breakdown.

In some embodiments, the ablation device (5000 may be configured for delivering the pulse waveform to tissue during use via the set of electrodes (520, 522, 524, 526). In some embodiments, the pulse waveform may be applied between the electrodes (520, 522, 524, 526) configured in anode and cathode sets. For example, approximately diametrically opposite electrode pairs (e.g., electrodes (520, 524) and (522, 526)) may be activated together as an anode-cathode pair. In other embodiments, adjacent electrodes may be configured as an anode-cathode pair. As an example, a first electrode (520) of the set of electrodes may be configured as an anode and a second electrode (522) may be configured as a cathode.

FIGS. 6-9E and 26A-27C illustrate additional embodiments of an ablation device (e.g., structurally and/or functionally similar to the ablation device (110)) that may be configured to deliver voltage pulse waveforms using a set of electrodes to ablate tissue and electrically isolate a pulmonary vein. In some of these embodiments, the ablation device may be transformed from a first configuration to a second configuration such that the electrodes of the ablation device expand outward to contact a lumen of tissue (e.g., pulmonary vein antrum).

Figure 6:
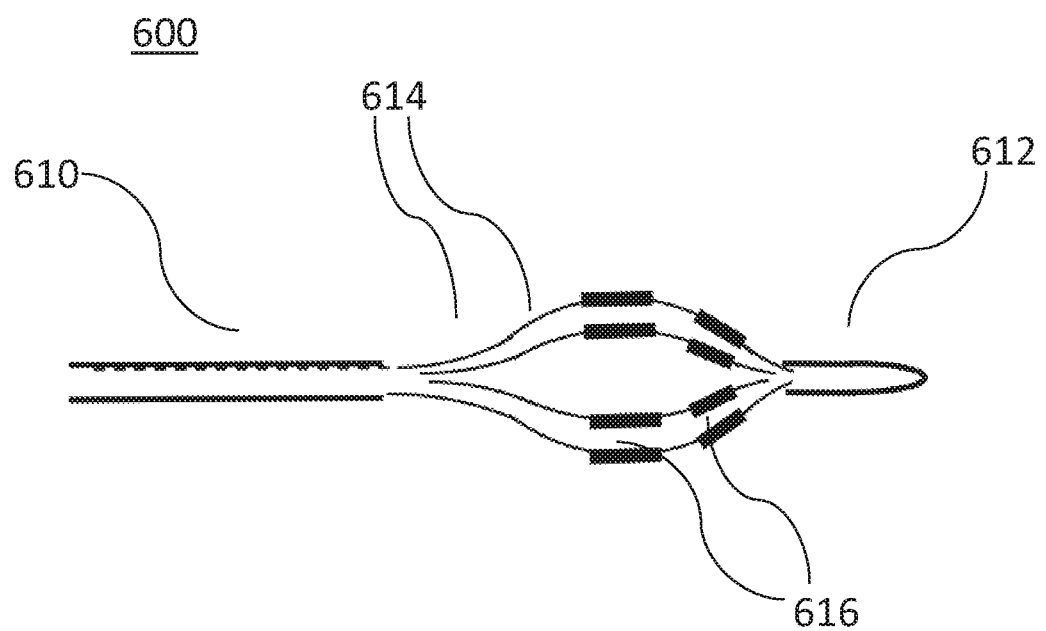
FIG. 6 is a side view of an ablation catheter, according to other embodiments.

FIG. 6 is a side view of an embodiment of an ablation device (600) including a catheter shaft (610) at a proximal end of the device (600), a distal cap (612) of the device (600), and a set of splines (614) coupled thereto. The distal cap (612) may include an atraumatic shape to reduce trauma to tissue. A proximal end of the set of splines (614) may be coupled to a distal end of the catheter shaft (610), and a distal end of the set of splines (614) may be tethered to the distal cap (612) of the device (600). The ablation device (600) may be configured for delivering a pulse waveform to tissue during use via one or more splines of the set of splines (614).

Each spline (614) of the ablation device (600) may include one or more jointly wired, or in some cases independently addressable electrodes (616) formed on a surface of the spline (614). Each electrode (616) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2,000 V across its thickness without dielectric breakdown. Each spline (614) may include the insulated electrical leads of each electrode (616) formed in a body of the spline (614) (e.g., within a lumen of the spline (614)). In cases where the electrodes on a single spline are wired together, a single insulated lead may carry strands connecting to different electrodes on the spline. FIG. 6 illustrates a set of splines (614) where each spline (614) includes a pair of electrodes (616) having about the same size, shape, and spacing as the electrodes (616) of an adjacent spline (614). In other embodiments, the size, shape, and spacing of the electrodes (616) may differ.

For each of the ablation devices described herein, and the ablation devices described in FIGS. 6-9 in particular, each spline of the set of splines may include a flexible curvature. The minimum radius of curvature of a spline can be in the range of about 1 cm or larger. For example, the set of splines may form a delivery assembly at a distal portion of the ablation device and be configured to transform between a first configuration where the set of splines bow radially outward from a longitudinal axis of the ablation device, and a second configuration where the set of splines are arranged generally parallel to the longitudinal axis of the ablation device. In this manner, the splines may more easily conform to the geometry of an endocardial space. In general, the "basket" of splines can have an asymmetric shape along the shaft length, so that one end (for example, the distal end) of the basket is more bulbous than the other end (for example, the proximal end) of the basket. The delivery assembly may be disposed in the first configuration in contact with a pulmonary vein antrum and transformed to the second configuration prior to delivering a pulse waveform. In some of these embodiments, a handle may be coupled to the set of splines and the handle configured for affecting transformation of the set of splines between the first configuration and the second configuration. In some embodiments, the electrical leads of at least two electrodes of the set of electrodes may be electrically coupled at or near a proximal portion of the ablation device, such as, for example, within the handle.

In one embodiment, each of the electrodes (616) on a spline (614) may be configured as an anode while each of the electrodes (616) on an adjacent spline (614) may be configured as a cathode. In another embodiment, the electrodes (616) on one spline may alternate between an anode and cathode with the electrodes of an adjacent spline having a reverse configuration (e.g., cathode and anode). The ablation device (600) may include any number of splines, for example, 3, 4, 5, 6, 7, 8, 9, 10, 12, 14, 16, 18, 20, or more splines, including all values and sub-ranges in between. In some embodiments, the ablation device (600) may include 3 to 20 splines. For example, the ablation device (600) may include 6 to 12 splines.

Figure 7:
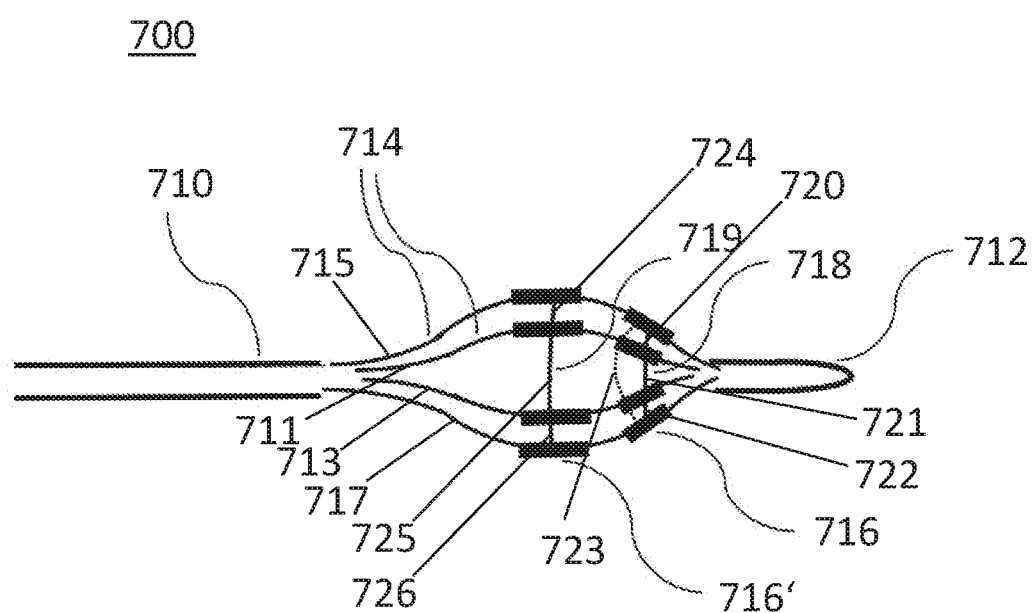
FIG. 7 is a side view of an ablation catheter, according to other embodiments.

FIG. 7 is a side view of another embodiment of an ablation device (700) including a catheter shaft (710) at a proximal end of the device (700), a distal cap (712) of the device (700), and a set of splines (714) coupled thereto. The distal cap (712) may include an atraumatic shape. A proximal end of the set of splines (714) may be coupled to a distal end of the catheter shaft (710), and a distal end of the set of splines (714) may be tethered to the distal cap (712) of the device (700). Each spline (714) of the ablation device (700) may include one or more independently addressable electrodes (716) formed on a surface of the spline (714). Each electrode (716) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 1500 V across its thickness without dielectric breakdown. Each spline (714) may include the insulated electrical leads of each electrode (716) formed in a body of the spline (714) (e.g., within a lumen of the spline (714)). A set of spline wires (718, 719) may be electrically conductive and electrically couple adjacent electrodes (716) disposed on different splines (714) such as electrodes (716) between a pair of splines (718, 719) of the set of splines. For example, the spline wires (718, 719) may extend in a transverse direction relative to a longitudinal axis of the ablation device (700).

FIG. 7 illustrates a set of splines (714) where each spline (714) includes a pair of electrodes (716) having about the same size, shape, and spacing as the electrodes (716) of an adjacent spline (714). In other embodiments, the size, shape, and spacing of the electrodes (716) may differ. For example, the electrodes (716) electrically coupled to a first spline wire (718) may differ in size and/or shape from electrodes (716') electrically coupled to a second spline wire (719).

In some embodiments, the first spline wire (718) may include a first set of spline wires (720, 721, 722, 723), where each spline wire of the set of spline wires (720, 721, 722, 723) may couple electrodes (716) between a different pair of splines of the set of splines (714). In some of these embodiments, the set of spline wires (720, 721, 722, 723) may form a continuous loop between the electrodes (716) coupled thereto. Likewise, the second spline wire (719) may include a second set of spline wires (724, 725, 726), where each spline wire of the set of spline wires (724, 725, 726) may couple electrodes (716') across the set of splines (714). The second set of spline wires (724, 725, 726) may couple different electrodes (716') across the set of splines (714) than the first set of spline wires (720, 721, 722, 723). In some of these embodiments, the first set of spline wires (720, 721, 722, 723) may form a first continuous loop between the electrodes (716) coupled thereto and the second set of spline wires (724, 725, 726) may form a second continuous loop between the electrodes (716') coupled thereto. The first continuous loop may be electrically isolated from the second continuous loop. In some of these embodiments, the electrodes (716) coupled to the first continuous loop may be configured as anodes and the electrodes (716) coupled to the second continuous loop may be configured as cathodes. A pulse waveform may be delivered to the electrodes (716) of the first and second continuous loop. In some embodiments, the spline wires such as 721, 722, 723 etc. can be replaced by similar electrical connections in the proximal part of the device (for example, in the device handle). For example, the electrodes 716 can all be electrically wired together in the handle of the device.

In another embodiment, the first spline wire (721) of the set of spline wires (720, 721, 722, 723) may couple electrodes (716) between a first spline (711) and a second spline (713) of the set of splines (714), and a second spline wire (720) of the set of spline wires (720, 721, 722, 723) may couple electrodes (716) between the first spline (711) and a third spline (715) of the set of splines (714). The electrodes (716) coupled by the first spline wire (721) and the second spline wire (720) may be configured as an anode and cathode (or vice-versa). In yet another embodiment, the first spline wire (721) of the set of spline wires (720, 721, 722, 723) may couple the electrodes (716) between a first spline (711) and a second spline (713) of the set of splines (714), and a second spline wire (723) of the set of spline wires (720, 721, 722, 723) may couple the electrodes (716) between a third spline (715) and a fourth spline (717) of the set of splines (714). A pulse waveform may be delivered to the electrodes (716) coupled by the first spline wire (721) and the second spline wire (723). In some embodiments, instead of spline wires the electrical leads of at least two electrodes of the set of electrodes are electrically coupled at or near a proximal portion of the ablation device, such as, for example, within a handle.

In other embodiments, one or more of the spline wires (718, 719) may form a continuous loop between the electrically coupled electrodes (716). For example, a first set of spline wires (718) may form a first continuous loop between the electrodes (716) coupled thereto and a second set of spline wires (719) may form a second continuous loop between the electrodes (716) coupled thereto. In this case, the first continuous loop may be electrically isolated from the second continuous loop. In one embodiment, each of the electrodes (716) coupled to a first set of spline wires (718) may be configured as an anode while each of the electrodes (716) coupled to a second set of spline wires (719) may be configured as a cathode. Each group of electrically coupled electrodes (716) may be independently addressable. In some embodiments, instead of spline wires the electrical leads of at least two electrodes of the set of electrodes are electrically coupled at or near a proximal portion of the ablation device, such as, for example, within a handle.

In some embodiments, as discussed in further detail below with respect to FIGS. 8A-8B, a spline wire may electrically couple to a set of electrodes (e.g., 2, 3, 4, 5, etc.) without forming a continuous loop. For example, a discontinuous loop may be formed using two spline wires. In other embodiments, the size, shape, and spacing of the electrodes (716) may differ. The ablation device (700) may include any number of splines, for example, 3, 4, 5, 6, 7, 8, 9, 10, 12, 14, 16, 18, 20, or more splines. In some embodiments, the ablation device (700) may include 3 to 20 splines. For example, in one embodiment, the ablation device (700) may include 6 to 9 splines.

Figure 8A:
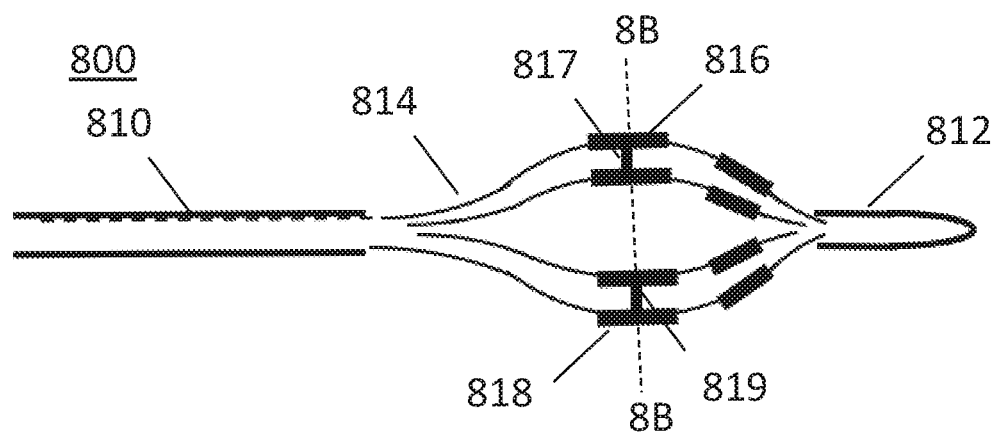
FIGS. 8A-8B are views of an ablation catheter, according to other embodiments.
Figure 8B:
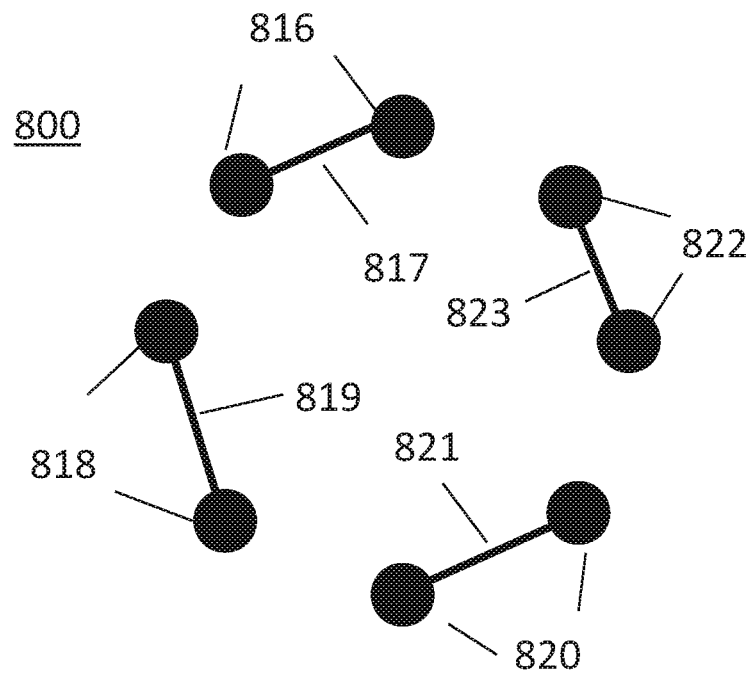

FIGS. 8A-8B are side and front cross-sectional views, respectively, of an ablation catheter (800). FIG. 8A is a side view of an embodiment of an ablation device (800) including a catheter shaft (810) at a proximal end of the device (800), a distal cap (812) of the device (800), and a set of splines (814) coupled thereto. The distal cap (812) may include an atraumatic shape. A proximal end of the set of splines (814) may be coupled to a distal end of the catheter shaft (810), and a distal end of the set of splines (14) may be tethered to the distal cap (812) of the device (800). Each spline (814) of the ablation device (800) may include one or more independently addressable electrodes (816, 818) formed on a surface of the spline (814). Each electrode (816, 818) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2,000 V across its thickness without dielectric breakdown, including all values and subranges in between. Each spline (814) may include the insulated electrical leads of each electrode (816, 818) formed in a body of the spline (814) (e.g., within a lumen of the spline (814)). One or more spline wires (817, 819) may be electrically conductive and electrically couple adjacent electrodes (816, 818) disposed on different splines (814). For example, the spline wires (817, 819) may extend in a transverse direction relative to a longitudinal axis of the ablation device (800).

FIG. 8B is a front cross-sectional view of FIG. 8A taken along the 8B-8B line. Each spline wire (817, 819, 821, 823) electrically couples a pair of adjacent electrodes (816, 818, 820, 822) on different splines. In some embodiments, each coupled electrode pair may be electrically isolated from each other. In some embodiments, the coupled electrode pair may be configured with a common polarity. Adjacent pairs of electrodes may be configured with opposite polarities (e.g., a first electrode pair configured as an anode and an adjacent second electrode pair configured as a cathode). For example, the electrodes (816) coupled to a first set of spline wires (817) may be configured as an anode while each of the electrodes (818) coupled to a second set of spline wires (819) may be configured as a cathode. In some embodiments, each electrode formed on a spline (814) may share a common polarity (e.g., configured as an anode or cathode). Each coupled electrode pair may be independently addressable. In some embodiments, the ablation device (800) may include an even number of splines. The ablation device (800) may include any number of splines, for example, 4, 6, 8, 10, or more splines. In some embodiments, the ablation device may include 4 to 10 splines. For example, in one embodiment, the ablation device may include 6 to 8 splines. As indicated in the foregoing, in some embodiments, the spline wires such as 817, 819, etc. can be replaced by similar electrical connections in the proximal part of the device (for example, in the device handle). For example, the electrodes (816) can be electrically wired together in the handle of the device, so that these electrodes are at the same electric potential during ablation.

Figure 9A:
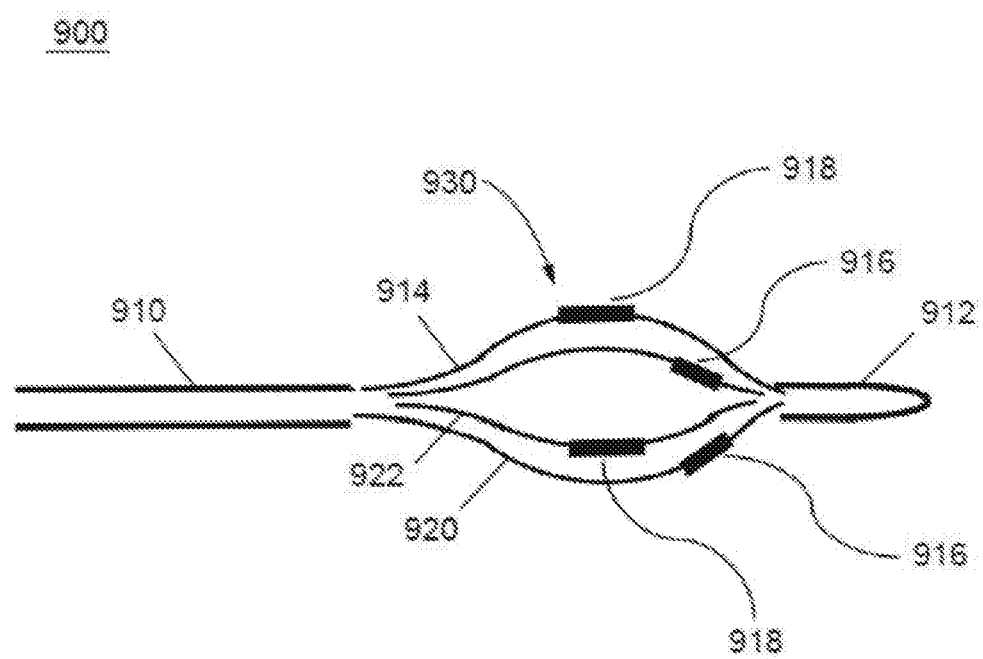
FIGS. 9A-9E are each side views of an ablation catheter, according to other embodiments.

FIG. 9A is a side view of yet another embodiment of an ablation device (900) including a catheter shaft (910) at a proximal end of the device (900), a distal cap (912) of the device (900), and a set of splines (914) coupled thereto. The distal cap (912) may include an atraumatic shape. A proximal end of the set of splines (914) may be coupled to a distal end of the catheter shaft (910), and a distal end of the set of splines (914) may be tethered to the distal cap (912) of the device (900). Each spline (914) of the ablation device (900), may include one or more independently addressable electrodes (916, 918) formed on a surface of the spline (914). Each electrode (916, 918) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2,000 V across its thickness without dielectric breakdown. Each spline (914) may include the insulated electrical leads of each electrode (916, 918) formed in a body of the spline (914) (e.g., within a lumen of the spline (914)). FIG. 9A illustrates a set of splines (914) where each spline (914) includes an electrode spaced apart or offset from an electrode of an adjacent spline (914). For example, the set of splines (914) including a first spline (920) and a second spline (922) adjacent to the first spline (920), wherein an electrode (916) of the first spline (920) is disposed closer to a distal end (912) of the ablation device (900) relative to an electrode (918) of the second spline (922). In other embodiments, the size and shape of the electrodes (916, 918) may differ as well.

In some embodiments, adjacent distal electrodes (916) and proximal electrodes (918) may form an anode-cathode pair. For example, the distal electrodes (916) may be configured as an anode and the proximal electrodes (918) may be configured as a cathode. In some embodiments, the ablation device (900) may include 3 to 12 splines. In FIG. 9A, one electrode (916, 918) is formed on a surface of each spline (914) such that each spline (914) includes one insulated electrical lead. A lumen of the spline (914) may therefore be reduced in diameter and allow the spline (914) to be thicker and more mechanically robust. Thus, dielectric breakdown of the insulation may be further reduced, thereby improving reliability and longevity of each spline (914) and the ablation device (900). The ablation device (900) may include any number of splines, for example, 3, 4, 5, 6, 7, 8, 9, 10, 12, 14, 16, 18, 20, or more splines. In some embodiments, the ablation device (900) may include 3 to 20 splines. For example, in one embodiment, the ablation device (900) may include 6 to 10 splines. Furthermore, in some embodiments, the shape of a bulb-like expanded structure (930) of the expanded set of splines (914) may be asymmetric, for example with its distal portion being more bulbous or rounded than its proximal portion (e.g., see FIGS. 9B-9E). Such a bulbous distal portion can aid in positioning the device at the ostium of a pulmonary vein.

Figure 9B:
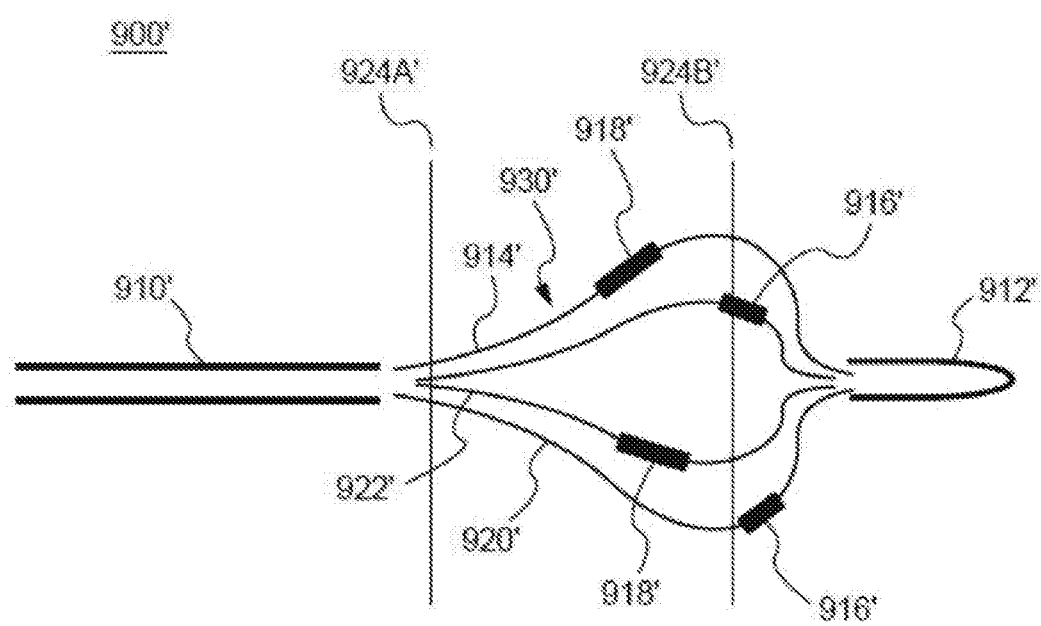

Referring to FIGS. 9B-9E, it is understood that unless indicated otherwise, components with similar references numbers to those in FIG. 9A (e.g., the electrode (916) in FIG. 9A and the electrode (916') in FIG. 9B) may be structurally and/or functionally similar. FIG. 9B illustrates the spline wires (914', 920', 922') forming an expanded structure (930') during use such as when deployed. A first plane (924A'), also sometimes referred to as a proximal plane, of the expanded structure (930') has a cross-sectional area that is different than a cross-sectional area at a second plane (924B') of the expanded structure (930'). As illustrated in FIG. 9B, in some embodiments, the cross-sectional area of the expanded structure (930') at the second plane (924B') is greater than that at the first plane (924A'). The terms "first plane" and "second plane" as used with respect to FIG. 9B may refer to planes orthogonal to the longitudinal axis of the catheter shaft (910') that are each formed up to about 1 cm, about 2 cm, and about 3 cm or more (including all values and sub-ranges in between) from the distal end of the catheter shaft (910') and the proximal end of the distal cap (912'), respectively. Similar to FIG. 9A, the electrode (916') of the first spline (920') is disposed closer to the distal cap (912') of the ablation device (900') relative to an electrode (918') of the second spline (922').

Figure 9C:
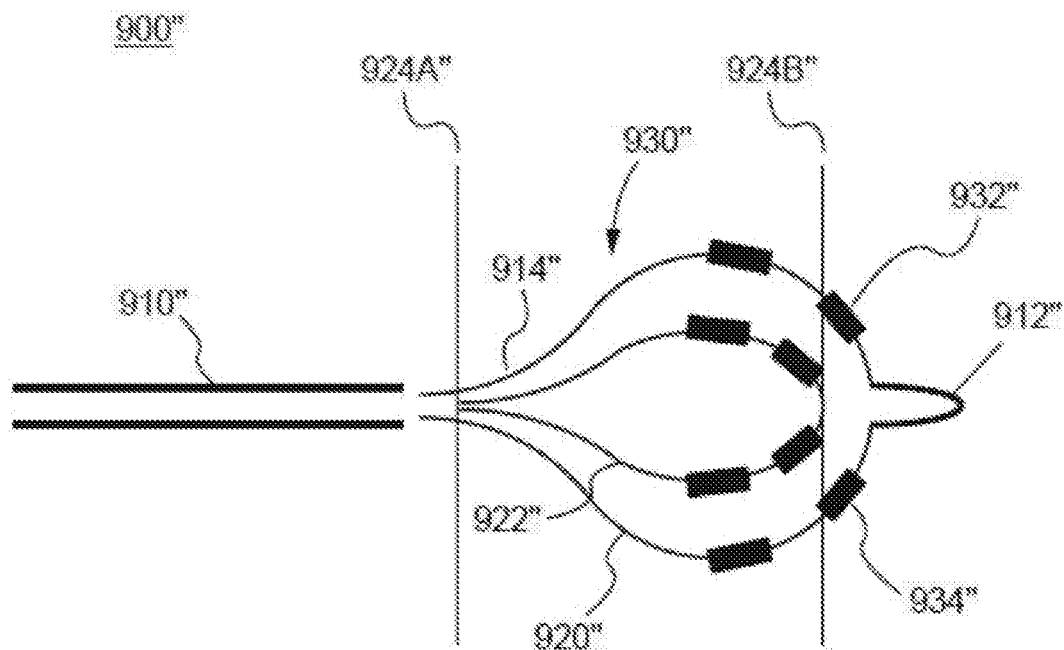

FIG. 9C illustrates the spline wires (914", 920", 922") forming an expanded structure (930") during use such as when deployed. A first plane (924A"), also sometimes referred to as a proximal plane, of the expanded structure (930") has a cross-sectional area that is different than a cross-sectional area at a second plane (924B") of the expanded structure (930"). As illustrated in FIG. 9C, in some embodiments, the cross-sectional area of the expanded structure (930") at the second plane (924B") is greater than that at the first plane (924A"). The terms "first plane" and "second plane" as used with respect to FIG. 9C may refer to planes orthogonal to the longitudinal axis of the catheter shaft (910") that are each formed up to about 1 cm, about 2 cm, and about 3 cm or more (including all values and sub-ranges in between) from the distal end of the catheter shaft (910") and the proximal end of the distal cap (912"), respectively. Unlike FIGS. 9A-9B, multiple electrodes may be present on each spline wire, and some electrodes may be equidistant from the distal cap (912"). In this manner, relatively distal electrodes such as 932" and 934" may be apposed at or proximal/antral to a pulmonary vein ostium during use for ablation delivery to generate an ostial circumferential lesion around a pulmonary vein.

Figure 9D:
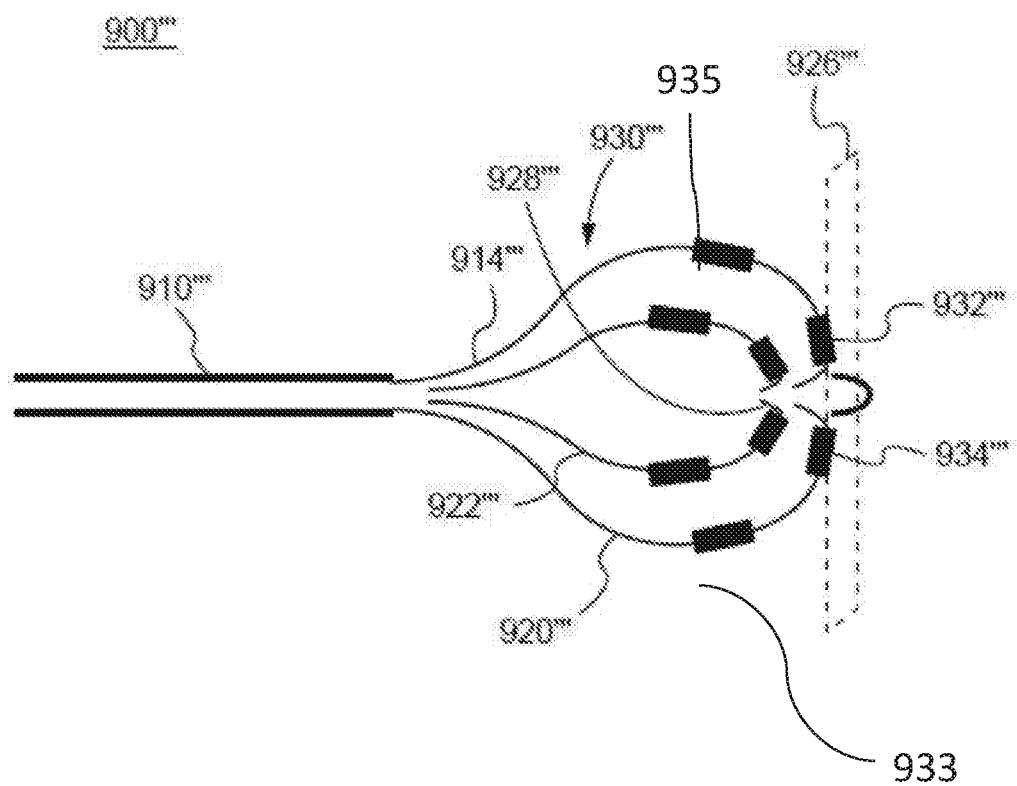

FIG. 9D illustrates the spline wires (914''', 920''', 922''') forming an expanded structure (930''') during use such as when deployed. The spline wires (914''', 920''', 922''') converge at their distal ends to a point (928''') that lies inside/within the expanded structure (930'''). As illustrated in FIG. 9D, in such a configuration, at least some electrodes (932''', 934''') on the spline wires (914''', 920''', 922''') may lie in a distal end plane (926''') of the expanded structure (930'''). The term "distal end plane" as used with respect to FIG. 9D may refer to a plane orthogonal to the longitudinal axis of the catheter shaft (910''') that passes through a distal boundary of the expanded structure (930'''). In this manner, the expanded structure (930''') may be pressed against, for example, an endocardial surface such as the posterior wall of the left atrium in order to directly generate lesions thereupon by activation of appropriate electrodes in the distal end plane using any suitable combination of polarities. For example, distal electrodes (932''', 934''') may be pressed against an endocardial surface. Distal electrodes (932''', 934''') may be configured with opposite polarities. In some embodiments, adjacent electrodes on the same spline may have the same polarity such that distal electrode (934''') may have the same polarity as proximal electrode (933) and likewise distal electrode (932''') may have the same polarity as proximal electrode (935). Electrodes (934''', 933) may have the opposite polarity as electrodes (932''', 935).

In some embodiments, adjacent distal electrodes (934''') and proximal electrodes (933) may form an anode-cathode pair. For example, the distal electrodes (934''') may be configured as an anode and the proximal electrodes (933) may be configured as a cathode. In another embodiment, the electrodes (2630) on one spline may alternate between an anode and cathode with the electrodes of an adjacent spline having a reverse configuration (e.g., cathode and anode).

Figure 9E:
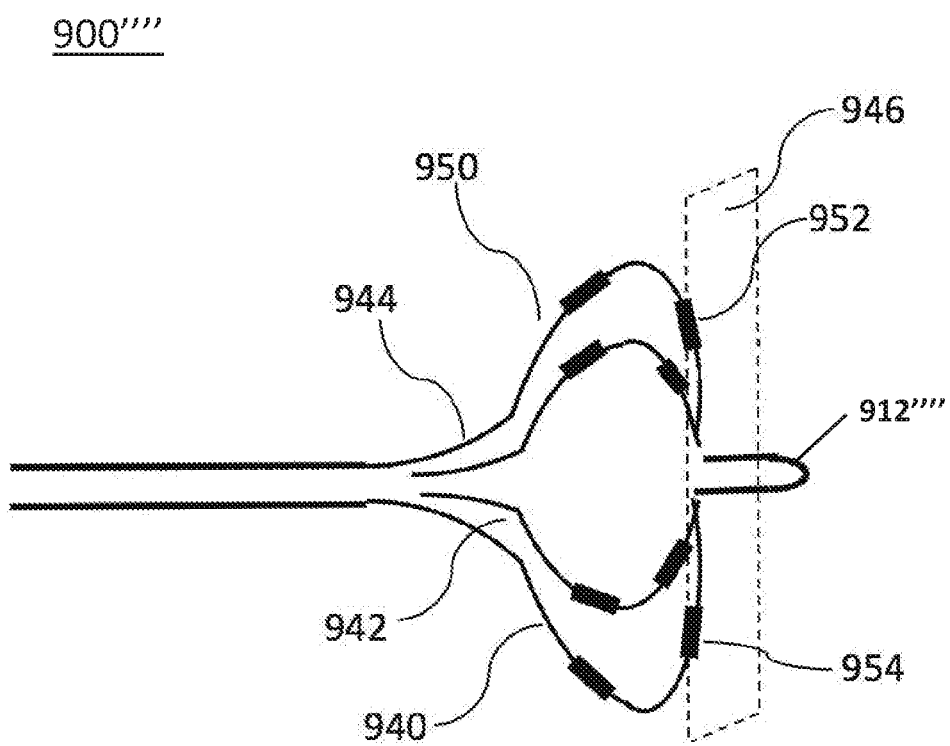

FIG. 9E illustrates the spline wires (944, 940, 942) forming an expanded structure (950) during use such as when deployed. The spline wires (944, 940, 942) converge at their distal ends at a proximal end of a distal cap (912'''') inside/within the expanded structure (950). As illustrated in FIG. 9E, in such a configuration, at least some electrodes (952, 954) on the spline wires (944, 940) may lie in a distal end plane (946) of the expanded structure (950). The term "distal end plane" as used with respect to FIG. 9E may refer to a plane orthogonal to the longitudinal axis of the catheter shaft (910'''') that passes through a distal boundary of the expanded structure (950). In this manner, the expanded structure (950) may be pressed against, for example, the posterior wall of the left atrium in order to directly generate lesions thereupon by activation of appropriate electrodes in the distal end plane (946) using any suitable combination of polarities. For example, the electrodes 952 and 954 may be configured with opposite polarities. Relative to the expanded structure (930'''') in FIG. 9D, the expanded structure (950) in FIG. 9E has a more orthogonal (e.g., flattened) shape that may be pressed against, for example, the posterior wall of the left atrium for tissue ablation. In other words, the cross-sectional area of the expanded structure (930'''') at the distal end plane (926'''') is less than that the cross-sectional area of the expanded structure (950) at the distal end plane (946).

For each of the ablation devices described herein, each of the splines may include a polymer and define a lumen so as to form a hollow tube. The one or more electrodes of the ablation device described herein may include a diameter from about 0.2 mm to about 2.0 mm and a length from about 0.2 mm to about 5.0 mm. In some embodiments, the electrode may include a diameter of about 1 mm and a length of about 1 mm. As the electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail below. It should be appreciated that the size, shape, and spacing of the electrodes on and between the splines may be configured to deliver contiguous/transmural energy to electrically isolate one or more pulmonary veins. In some embodiments, alternate electrodes (for example, all the distal electrodes) can be at the same electric potential, and likewise for all the other electrodes (for example, all the proximal electrodes). Thus ablation can be delivered rapidly with all electrodes activated at the same time. A variety of such electrode pairing options exist and may be implemented based on the convenience thereof.

Figure 25:
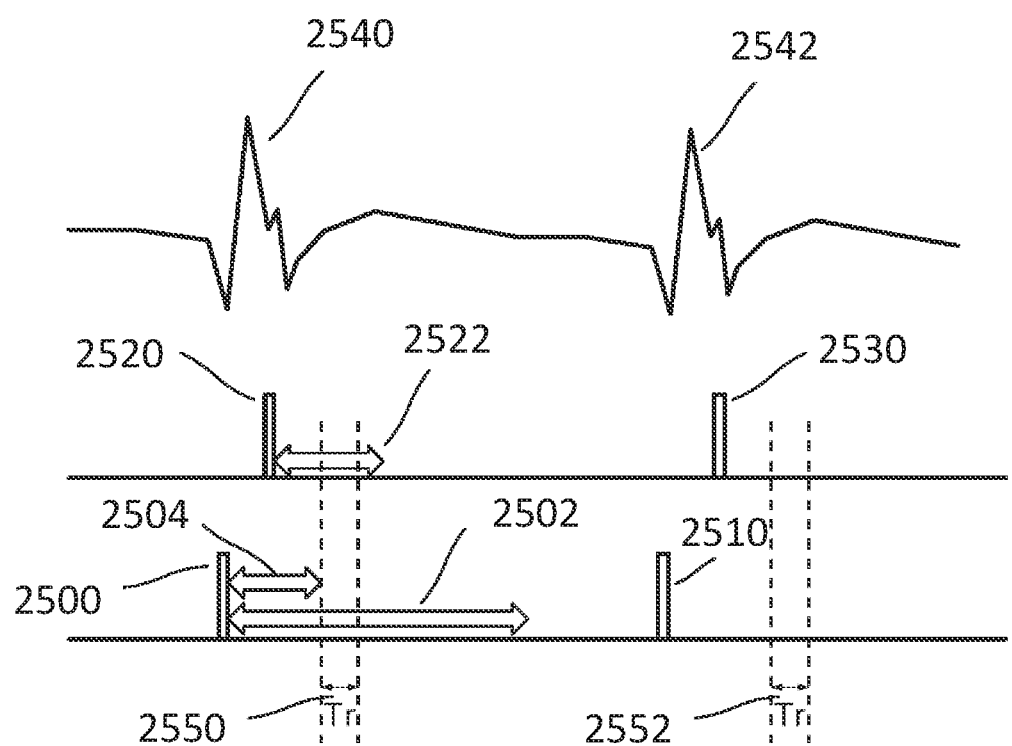
FIG. 25 illustrates schematically a time sequence of electrocardiograms and cardiac pacing signals together with atrial and ventricular refractory time periods and indicating a time window for irreversible electroporation ablation, according to embodiments.
Figure 26A:
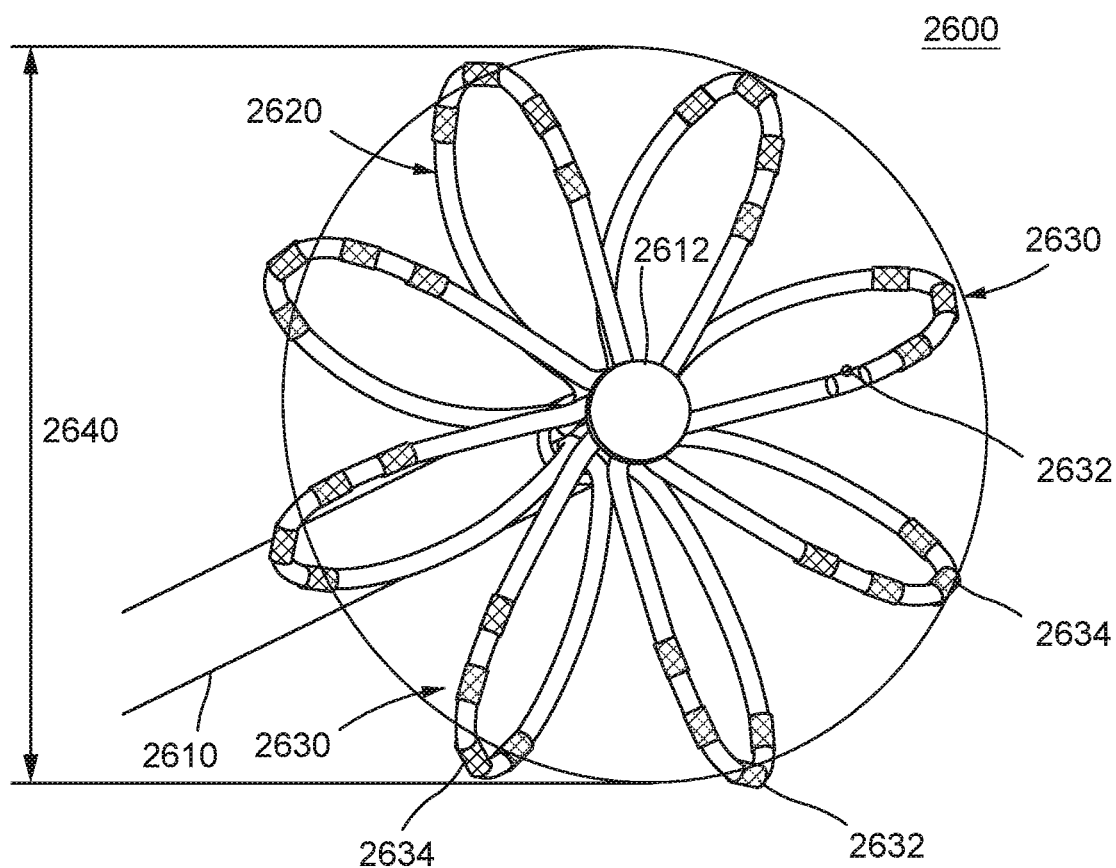
FIG. 26A is a perspective view of an ablation catheter, according to other embodiments.
Figure 26B:
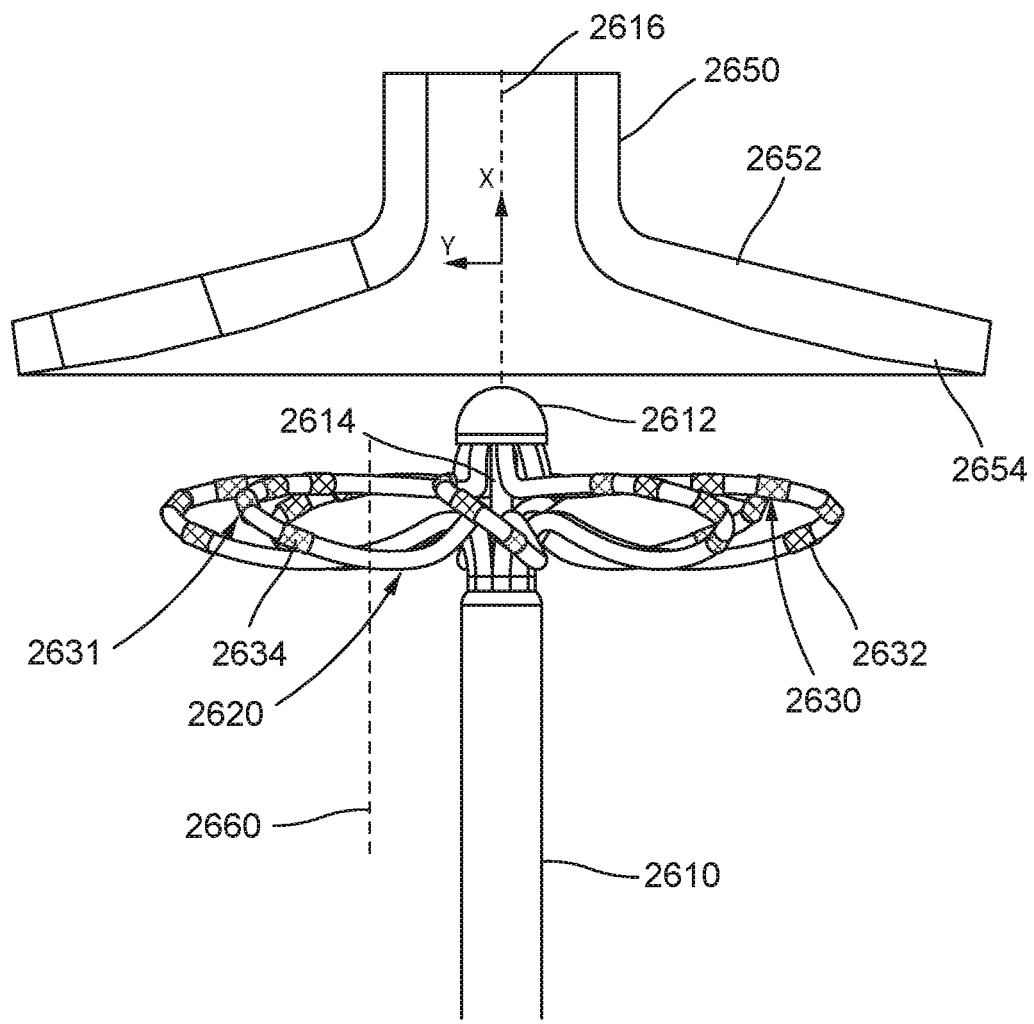
FIG. 26B is a side view of the ablation catheter depicted in FIG. 26A disposed in a left atrial chamber of a heart, adjacent to a pulmonary vein antrum.

FIG. 26A is a perspective view of an embodiment of an ablation device (2600) having a flower-like shape and including a catheter shaft (2610) at a proximal end of the device (2600), a distal cap (2612) of the device (2600), and a set of splines (2620) coupled thereto. As best shown in FIG. 26B, a spline shaft (2614) may be coupled at a proximal end to the proximal end of the handle (not shown) and coupled at a distal end to the distal cap (2612). In preferred embodiments, the distance between the distal cap 2612 and the catheter shaft 2610 may be less than about 8 mm. The spline shaft (2614) and distal cap (2612) may be translatable along a longitudinal axis (2616) of the ablation device (2600). The spline shaft (2614) and distal cap (2612) may move together. The spline shaft (2614) may be configured to slide within a lumen of the catheter shaft (2610). The distal cap (2612) may include an atraumatic shape to reduce trauma to tissue. A proximal end of each spline of the set of splines (2620) may pass through a distal end of the catheter shaft (2610) and be tethered to the catheter shaft within the catheter shaft lumen, and a distal end of each spline of the set of splines (2620) may be tethered to the distal cap (2612) of the device (2600). The ablation device (2600) may be configured for delivering a pulse waveform, as disclosed for example in FIGS. 21-25, to tissue during use via one or more splines of the set of splines (2620).

Each spline (2620) of the ablation device (2600) may include one or more jointly wired electrodes (2630) formed on a surface of the spline (2620), in some embodiments. In other embodiments, one or more of the electrodes (2630) on a given spline may be independently addressable electrodes (2630). Each electrode (2630) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2,000 V across its thickness without dielectric breakdown. Each spline (2620) may include the insulated electrical leads of each electrode (2630) within a body of the spline (2620) (e.g., within a lumen of the spline (2620)). FIG. 26A illustrates a set of splines (2620) where each spline includes a set of electrodes (2632 or 2634) having about the same size, shape, and spacing as the electrodes (2634 or 2632) of an adjacent spline (2620). In other embodiments, the size, shape, and spacing of the electrodes (2632, 2634) may differ. The thickness of each spline (2620) may vary based on the number of electrodes (2630) formed on each spline (2620) which may correspond to the number of insulated electrical leads in the spline (2620). The splines (2620) may have the same or different materials, thickness, and/or length.

Figure 26C:
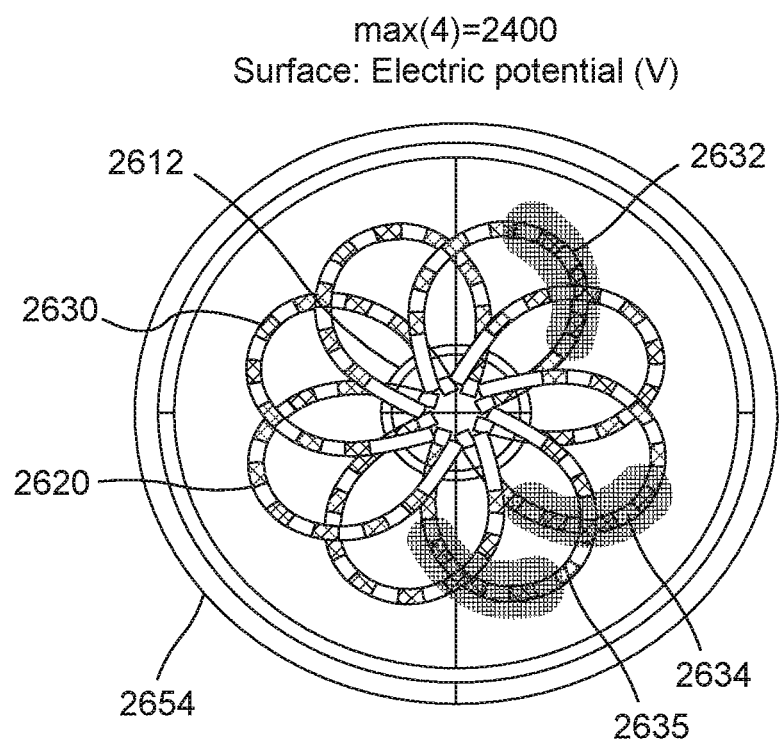
FIG. 26C is a top view of a simulation of the ablation catheter depicted in FIG. 26B, illustrating selective electrode activation according to embodiments.

Each spline of the set of splines (2620) may include a flexible curvature so as to rotate, or twist and bend and form a petal-shaped curve such as shown in FIGS. 26A-26C. The minimum radius of curvature of a spline in the petal-shaped configuration may be in the range of about 7 mm to about 25 mm. For example, the set of splines may form a delivery assembly at a distal portion of the ablation device (2600) and be configured to transform between a first configuration where the set of splines are arranged generally parallel to the longitudinal axis of the ablation device (2600), and a second configuration where the set of splines rotate around, or twist and bend, and generally bias away from the longitudinal axis of the ablation device (2600). In the first configuration, each spline of the set of splines may lie in one plane with the longitudinal axis of the ablation device. In the second configuration, each spline of the set of splines may bias away from the longitudinal axis to form a petal-like curve arranged generally perpendicular to the longitudinal axis. In this manner, the set of splines (2620) twist and bend and bias away from the longitudinal axis of the ablation device (2600), thus allowing the splines (2620) to more easily conform to the geometry of an endocardial space, and particularly adjacent to the opening of a pulmonary ostium. The second configuration may, for example, resemble the shape of a flower, when the ablation device is viewed from the front as best shown in FIG. 26C. In some embodiments, the each spline in the set of splines in the second configuration may twist and bend to form a petal-like curve that, when viewed from front, displays an angle between the proximal and distal ends of the curve of more than 180 degrees. The set of splines may further be configured to transform from a second configuration to a third configuration where the set of splines (2620) may be impressed (e.g., in contact with) against target tissue such as tissue surrounding a pulmonary vein ostium.

In some embodiments, the spline shaft (2614) coupled to the set of splines (2620) may allow each spline of the set of splines (2620) to bend and twist relative to the catheter shaft (2610) as the spline shaft (2614) slides within a lumen of the catheter shaft (2610). For example, the set of splines (2620) may form a shape generally parallel to a longitudinal axis of the spline shaft (2614) when undeployed, be wound (e.g., helically, twisted) about an axis (2660) parallel to the longitudinal axis of the spline shaft (2620) when fully deployed, and form any intermediate shape (such as a cage or barrel) in-between as the spline shaft (2614) slides within a lumen of the catheter shaft (2610).

In some embodiments, the set of splines in the first configuration, such as the spline (2620), may be wound about an axis (2660) parallel to the longitudinal axis of the catheter shaft (2610) in some portions along its length but elsewhere may otherwise be generally parallel to the longitudinal axis of the catheter shaft (2610). The spline shaft (2614) may be retracted into the catheter shaft (2610) to transform the ablation device (2600) from the first configuration to the second configuration where the splines (2620) are generally angled or offset (e.g., perpendicular) with respect to the longitudinal axis of the catheter shaft (2610) and twisted. As shown in the front view of FIG. 26C, each spline (2620) may form a twisting loop in this front view projection. In FIG. 26C, each spline (2620) has a set of electrodes (2630) having the same polarity. As shown in the front view of FIG. 26C, each spline of the set of splines (2620) may form a twisted loop such that each spline overlaps one or more other splines. The number and spacing of the electrodes (2630), as well as the rotated twist of the spline (2620), may be configured by suitable placement of electrodes along each spline to prevent overlap of an electrode (2630) on one spline with an electrode of an adjacent, overlapping spline (2620).

A spline having a set of anode electrodes (2632) may be activated together to deliver pulse waveforms for irreversible electroporation. Electrodes on other splines may be activated together as cathode electrodes such as electrodes (2634) and (2635) on their respective splines so at to form an anode-cathode pairing for delivery of pulse waveforms for irreversible electroporation, as shown in FIG. 26C. The anode-cathode pairing and pulse waveform delivery can be repeated sequentially over a set of such pairings.

For example, the splines (2620) may be activated sequentially in a clockwise or counter-clockwise manner. As another example, the cathode splines may be activated sequentially along with respective sequential anode spline activation until ablation is completed. In embodiments where electrodes on a given spline are wired separately, the order of activation within the electrode of each spline may be varied as well. For example, the electrodes in a spline may be activated all at once or in a predetermined sequence.

The delivery assembly may be disposed in the first configuration prior to delivering a pulse waveform and transformed to the second configuration to make contact with the pulmonary vein ostium or antrum. In some of these embodiments, a handle may be coupled to the spline shaft (2614) and the handle configured for affecting transformation of the set of splines between the first configuration and the second configuration. For example, the handle may be configured to translate the spline shaft (2614) and distal cap (2612) relative to the catheter shaft (2610), thereby actuating the set of splines (2620) coupled to the distal cap and causing them to bend and twist. The proximal ends of the splines (2620) may be fixed to the spline shaft (2614) thereby generating buckling of the splines (2620) resulting in a bending and twisting motion of the splines (2620), for example, as the distal cap (2612) and spline shaft (2614) are pulled back relative to the catheter shaft (2610) that may be held by a user. For example, a distal end of the set of splines (2620) tethered to the distal cap (2612) may be translated by up to about 60 mm along the longitudinal axis of the ablation device to actuate this change in configuration. In other words, translation of an actuating member of the handle may bend and twist the set of splines (2620). In some embodiments, actuation of a knob, wheel, or other rotational control mechanism in the device handle may result in a translation of the actuating member or spline shaft and result in bending and twisting of the splines (2620). In some embodiments, the electrical leads of at least two electrodes of the set of electrodes (2630) may be electrically coupled at or near a proximal portion of the ablation device (2600), such as, for example, within the handle.

Retraction of the spline shaft (2614) and distal cap (2612) may bring the set of splines (2620) closer together as shown in FIG. 26B where the set of splines (2620) are generally perpendicular to a longitudinal axis of the catheter shaft (2610). In some embodiments, each spline of the set of splines (2620) may be biased laterally away from the longitudinal axis of the spline shaft (2614) by up to about 3 cm. In some embodiments, the spline shaft (2614) may comprise a hollow lumen. In some embodiments, the cross section of a spline may be asymmetric so as to have a larger bending stiffness in one bending plane of the spline orthogonal to the plane of the cross section than in a different bending plane. Such asymmetric cross sections may be configured to present a relatively larger lateral stiffness and thereby may deploy with minimal overlap of the petal-shaped curves of each spline and its neighbors in the final or fully-deployed configuration.

In one embodiment, each of the electrodes (2632) on a spline (2620) may be configured as an anode while each of the electrodes (2634) on a different spline may be configured as a cathode. In another embodiment, the electrodes (2630) on one spline may alternate between an anode and cathode with the electrodes of another spline having a reverse configuration (e.g., cathode and anode).

In some embodiments, the spline electrodes may be electrically activated in sequential manner to deliver a pulse waveform with each anode-cathode pairing. In some embodiments, the electrodes may be electrically wired together within the spline, while in alternate embodiments they may be wired together in the handle of the device, so that these electrodes are at the same electric potential during ablation. In other embodiments, the size, shape, and spacing of the electrodes (2630) may differ as well. In some embodiments, adjacent distal electrodes and proximal electrodes may form an anode-cathode pair. For example, the distal electrodes may be configured as an anode and the proximal electrodes may be configured as a cathode.

The ablation device (2600) may include any number of splines, for example, 2, 3, 4, 5, 6, 7, 8, 9, 10, 12, 14, 16, 18, 20, or more splines, including all values and sub-ranges in between. In some embodiments, the ablation device (2600) may include 3 to 20 splines. For example, the ablation device (2600) may include from 4 to 12 splines.

Each of the splines of the set of splines (2620) may include respective electrodes (2630) having an atraumatic shape to reduce trauma to tissue. For example, the electrodes (2630) may have an atraumatic shape including a rounded, flat, curved, and/or blunted portion configured to contact endocardial tissue. In some embodiments, the electrodes (2630) may be located along any portion of the spline (2620) distal to the catheter shaft (2610). The electrodes (2630) may have the same or different sizes, shapes, and/or location along respective splines.

In this manner, the electrodes in the second configuration may be held close to or placed against a section of atrial wall of the left atrium in order to directly generate lesions thereupon by activation of appropriate electrodes using any suitable combination of polarities, as described herein. For example, the set of splines (2620) may be placed in contact against the atrial wall (2654) of atrium (2652) adjacent a pulmonary vein (2650) (e.g., ostium or antrum).

Figure 26D:
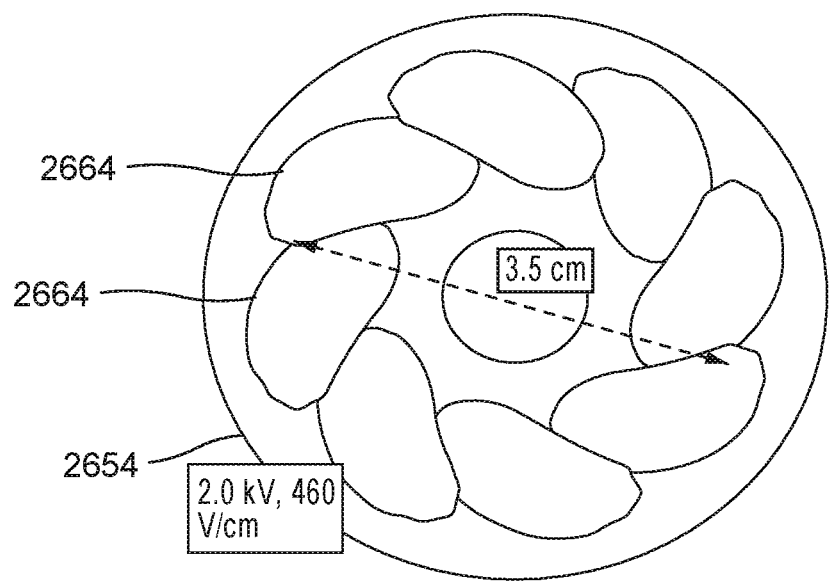
FIG. 26D is a simulated illustration of tissue ablation in a pulmonary vein antrum, according to embodiments.

FIG. 26D is a schematic illustration of ablation (2664) generated by the ablation device (2600) having a set of eight splines on tissue, such as the tissue surrounding a pulmonary vein ostium. For example, activation of one or more of the electrodes (2630) on one or more of the splines (2620) may generate one or more corresponding ablation areas (2664) along a wall (2654) of a pulmonary vein antrum or ostium. In some embodiments, an outline of the ablation areas (2664) in the pulmonary vein ostium may have a diameter of between about 2 cm and about 6 cm, and may be about 3.5 cm. In this manner, a contiguous, transmural lesion may be generated, resulting in electrical isolation of the pulmonary vein, which is a desired therapeutic outcome.

Figure 26E:
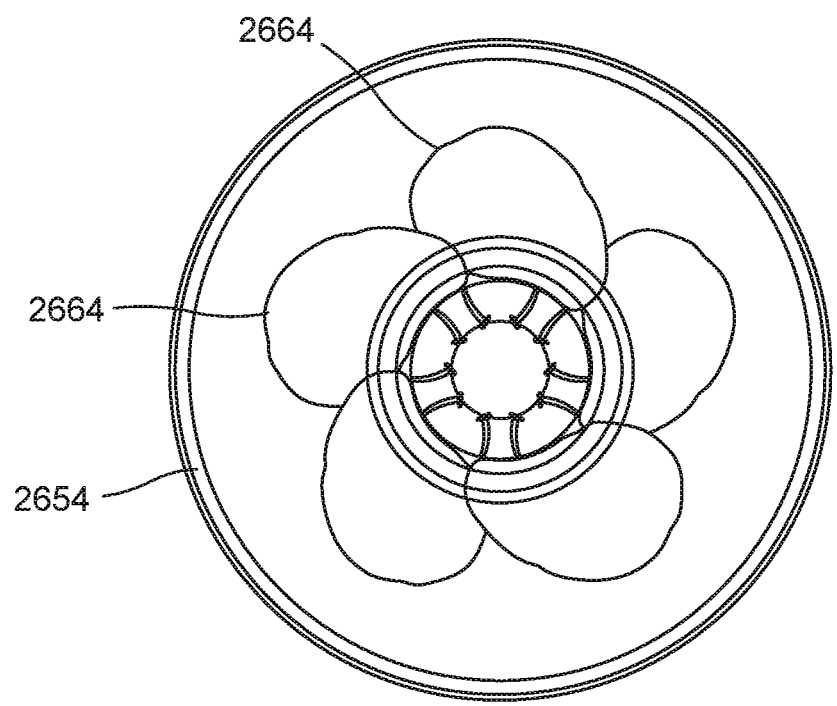
FIG. 26E is another simulated illustration of tissue ablation in a pulmonary vein antrum, according to embodiments.

FIG. 26E is another schematic illustration of ablation (2664) generated by the ablation device (2600) having a set of five splines on tissue, such as the tissue surrounding a pulmonary vein ostium. For example, activation of one or more of the electrodes (2630) on each of the five splines (2620) may generate five corresponding ablation areas (2664) along a wall (2654) of a pulmonary vein antrum or ostium. In this manner, a contiguous, transmural lesion may be generated, resulting in electrical isolation of the pulmonary vein, which may be a desired therapeutic outcome. An ablation device (2600) including a set of five splines may reduce and/or eliminate overlapping of spline petals, and allow for more evenly spaced splines during deployment.

Alternatively, the ablation catheter with its deployed electrodes may be placed adjacent to or against a section of posterior wall of the left atrium, and by activation of suitable electrode sets, an appropriate pulse waveform may be delivered for irreversible electroporation energy delivery to ablate tissue.

In some embodiments, as the electrodes or a subset of electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail herein. It should be appreciated that the size, shape, and spacing of the electrodes on and between the splines may be configured to deliver contiguous/transmural energy to electrically isolate one or more pulmonary veins. In some embodiments, alternate electrodes may be at the same electric potential, and likewise for all the other alternating electrodes. Thus, in some embodiments, ablation may be delivered rapidly with all electrodes activated at the same time. A variety of such electrode pairing options exists and may be implemented based on the convenience thereof.

Figure 27A:
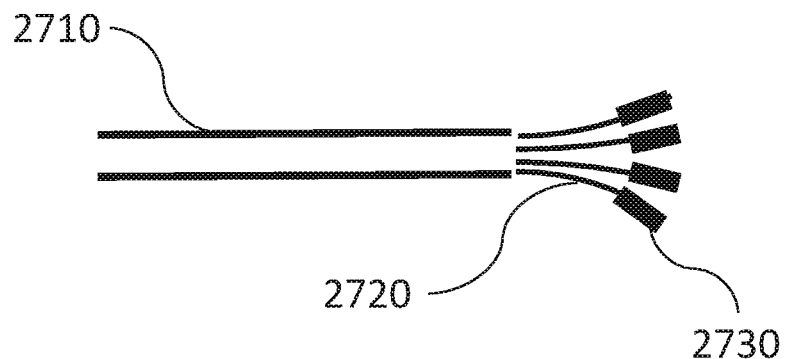
FIGS. 27A-27C are each side views of an ablation catheter, according to other embodiments.
Figure 27B:
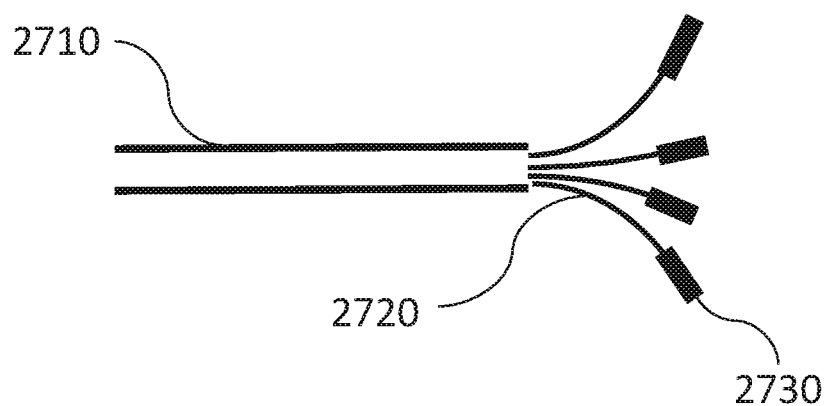

FIGS. 27A-27B are side views of an embodiment of an ablation device (2700) including a catheter shaft (2710) at a proximal end of the device (2700) and a set of splines (2720) coupled to the catheter shaft (2710) at a distal end of the device (2700). The ablation device (2700) may be configured for delivering a pulse waveform to tissue during use via one or more splines of the set of splines (2720). Each spline (2720) of the ablation device (2700) may include one or more possibly independently addressable electrodes (2730) formed on a surface (e.g., distal end) of the spline (2720). Each electrode (2730) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2,000 V across its thickness without dielectric breakdown. Each spline of the set of splines (2720) may include the insulated electrical leads of each electrode (2730) formed in a body of the spline (2720) (e.g., within a lumen of the spline (2720)). In some embodiments, the electrodes (2730) may be formed at the distal end of their respective spline (2720).

The set of splines (2720) may form a delivery assembly at a distal portion of the ablation device (2700) and be configured to transform between a first configuration and a second configuration. The set of splines (2720) in a first configuration are generally parallel to a longitudinal axis of the ablation device (2700) and may be closely spaced together. The set of splines (2720) in a second configuration are depicted in FIGS. 27A-27B where the set of splines (2720) extend out of the distal end of the catheter shaft (2710) and bias (e.g., curve) away from the longitudinal axis of the ablation device (2700) and other splines (2720). In this manner, the splines (2720) may more easily conform to the geometry of an endocardial space. The delivery assembly may be disposed in the first configuration prior to delivering a pulse waveform and transformed to the second configuration to a section of cardiac tissue such as the posterior wall of the left atrium, or a ventricle. Such a device delivering irreversible electroporation pulse waveforms may generate large lesions for focal ablations.

A distal end of the set of splines (2720) may be configured to bias away from a longitudinal axis of the distal end of the catheter shaft (2710) and bias away from the other splines. Each spline of the set of splines (2720) may include a flexible curvature. The minimum radius of curvature of a spline (2720) may be in the range of about 1 cm or larger.

In some embodiments, a proximal end of the set of splines (2720) may be slidably coupled to a distal end of the catheter shaft (2710). Accordingly, a length of the set of splines (2720) may be varied as shown in FIGS. 27A and 27B. As the set of splines (2720) are extended further out from the catheter shaft (2710), the distal ends of the set of splines (2720) may bias further away from each other and a longitudinal axis of the catheter shaft (2710). The set of splines (2720) may be slidably advanced out of the catheter shaft (2710) independently or in one or more groups. For example, the set of splines (2720) may be disposed within the catheter shaft (2710) in the first configuration. The splines (2720) may then be advanced out of the catheter shaft (2710) and transformed into the second configuration. The splines (2720) may be advanced all together or advanced such that the set of splines (2720) corresponding to the anode electrodes (2730) are advanced separately from the set of splines (2720) corresponding to the cathode electrodes (2730). In some embodiments, the splines (2720) may be advanced independently. In the second configuration, the electrodes (2730) are biased away from the catheter shaft (2710) longitudinally and/or laterally with respect to a longitudinal axis of a distal end of the catheter shaft (2710). This may aid delivery and positioning of the electrodes (2730) against an endocardial surface. In some embodiments, each of the set of splines (2720) may extend from a distal end of the catheter shaft (2710) by up to about 5 cm.

In some embodiments, the set of splines (2720) may have a fixed length from a distal end of the catheter shaft (2710). The splines (2720) may extend from a distal end of the catheter shaft (2710) at equal or unequal lengths. For example, a spline having a greater radius of curvature than an adjacent spline may extend further from the catheter shaft (2710) than the adjacent spline. The set of splines (2720) may be constrained by a lumen of a guide sheath, such that the set of splines (2720) are substantially parallel to the longitudinal axis of the catheter shaft (2710) in the first configuration.

In some of these embodiments, a handle (not shown) may be coupled to the set of splines. The handle may be configured for affecting transformation of the set of splines between the first configuration and the second configuration. In some embodiments, the electrical leads of at least two electrodes of the set of electrodes (2730) may be electrically coupled at or near a proximal portion of the ablation device, such as, for example, within the handle. In this case the electrodes (2730) may be electrically wired together in the handle of the device (2700), so that these electrodes (2730) are at the same electric potential during ablation.

Each of the splines of the set of splines (2720) may include respective electrodes (2730) at a distal end of the set of splines (2720). The set of electrodes (2730) may include an atraumatic shape to reduce trauma to tissue. For example, the electrodes (2730) may have an atraumatic shape including a rounded, flat, curved, and/or blunted portion configured to contact endocardial tissue. In some embodiments, the electrodes (2730) may be located along any portion of the spline (2720) distal to the catheter shaft (2710). The electrodes (2730) may have the same or different sizes, shapes, and/or location along respective splines. In one embodiment, an electrode (2730) on a spline (2720) may be configured as an anode while an electrode (2730) on an adjacent spline (2720) may be configured as a cathode. The ablation device (2700) may include any number of splines, for example, 3, 4, 5, 6, 7, 8, 9, 10, 12, 14, 16, 18, 20, or more splines, including all values and sub-ranges in between. In some embodiments, the ablation device (2700) may include 3 to 20 splines. For example, the ablation device (2700) may include 6 to 12 splines.

In FIGS. 27A-27B, one electrode (2730) is formed on a surface of each spline (2720) such that each spline (2720) includes one insulated electrical lead. A lumen of the spline (2720) may therefore be reduced in diameter and allow the spline (2720) to be thicker and more mechanically robust. Thus, dielectric breakdown of the insulation may be further reduced, thereby improving reliability and longevity of each spline (2720) and the ablation device (2700). Furthermore, in some embodiments, the radius of curvature of the spline may vary over a length of the spline. For example, the radius of curvature may decrease and then increase. Such a variable radius of curvature may aid in positioning the electrodes (2730) at some locations of endocardial tissue. The splines (2720) may have the same or different materials, thickness, and/or radius of curvature. For example, the thickness of each spline may reduce distally.

In this manner, the electrodes in the second configuration may be pressed against, for example, the posterior wall of the left atrium in order to directly generate localized or focal lesions thereupon by activation of appropriate electrodes using any suitable combination of polarities. For example, adjacent electrodes (2730) may be configured with opposite polarities.

As the electrodes or subsets of electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail herein. It should be appreciated that the size, shape, and spacing of the electrodes on and between the splines may be configured to deliver transmural lesions over relatively wide areas of endocardial tissue. In some embodiments, alternate electrodes may be at the same electric potential, and likewise for all the other alternating electrodes. Thus, ablation may be delivered rapidly with all electrodes activated at the same time. A variety of such electrode pairing options exists and may be implemented based on the convenience thereof.

Figure 27C:
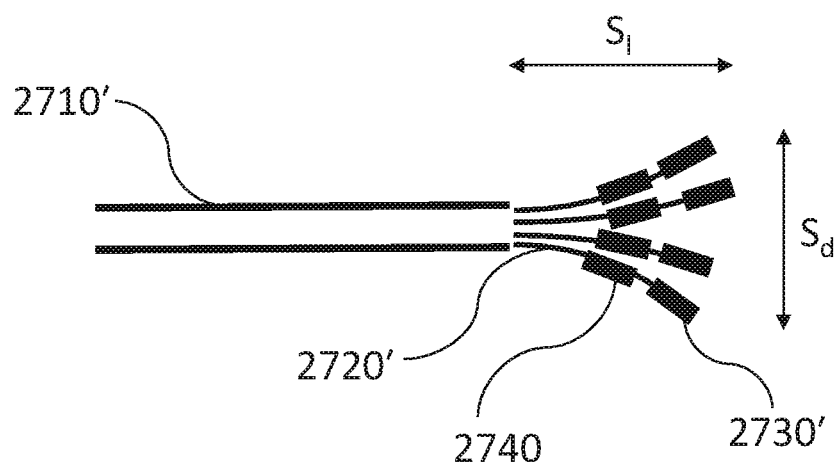

Referring to FIG. 27C, it is understood that unless indicated otherwise, components with similar references numbers to those in FIGS. 27A-27B (e.g., the electrode (2730) in FIGS. 27A-27B and the electrode (2730') in FIG. 27C) may be structurally and/or functionally similar. FIG. 27C illustrates a set of splines (2720') where each spline (2720') includes a pair of electrodes (2730', 2740). The ablation device (2700') includes a catheter shaft (2710') at a proximal end of the device (2700') and a set of splines (2720') coupled to the catheter shaft (2710') at a distal end of the device (2700'). The ablation device (2700') may be configured for delivering a pulse waveform to tissue during use via one or more splines of the set of splines (2720'). Each spline (2720') of the ablation device (2700') may include one or more independently addressable electrodes (2730', 2740) formed on a surface of the spline (2720'). Each electrode (2730', 2740) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2,000 V across its thickness without dielectric breakdown. Each spline of the set of splines (2720') may include the insulated electrical leads of each electrode (2730', 2740) formed in a body of the spline (2720') (e.g., within a lumen of the spline (2720')). Each electrode (2730', 2740) of a spline (2720') may have about the same size and shape. Furthermore, each electrode (2730', 2740) of a spline (2720') may have about the same size, shape, and spacing as the electrodes (2730', 2740) of an adjacent spline (2720').

In other embodiments, the size, shape, number, and spacing of the electrodes (2730', 2740) may differ. In some embodiments, the electrodes (2730', 2740) of the ablation device (2700') may have a length from about 0.5 mm to about 5.0 mm and a cross-sectional dimension (e.g., a diameter) from about 0.5 mm to about 4.0 mm, including all values and subranges in between. The spline wires (2720') in the second configuration may splay out to an extent Sa at a distal end of the ablation device (2700') from about 5.0 mm to about 20.0 mm from each other (including all values and subranges in between), and may extend from a distal end of the catheter shaft (2710') for a length Si from about 8.0 mm to about 20.0 mm, including all values and subranges in between. In some embodiments, the ablation device (2700') may include 4 splines, 5 splines, or 6 splines. In some embodiments, each spline may independently include 1 electrode, 2 electrodes, or 3 or more electrodes.

The set of splines (2720') may form a delivery assembly at a distal portion of the ablation device (2700') and be configured to transform between a first configuration and a second configuration. The set of splines (2720') in a first configuration are generally parallel to a longitudinal axis of the ablation device (2700) and may be closely spaced together. The set of splines (2720') in a second configuration are depicted in FIG. 27C where the set of splines (2720') extend out of the distal end of the catheter shaft (2710') and bias (e.g., curve) away from the longitudinal axis of the ablation device (2700') and other splines (2720'). In this manner, the splines (2720') may more easily conform to the geometry of an endocardial space. The delivery assembly may be disposed in the first configuration prior to delivering a pulse waveform and transformed to the second configuration to contact a region of endocardial tissue to generate large focal lesions upon delivery of pulse waveforms for irreversible electroporation as disclosed herein.

In some embodiments, a proximal end of the set of splines (2720') may be slidably coupled to a distal end of the catheter shaft (2710'). As the set of splines (2720') are extended further out from the catheter shaft (2710'), the distal ends of the set of splines (2720') may bias further away from each other and a longitudinal axis of the catheter shaft (2710'). The set of splines (2720') may be slidably advanced out of the catheter shaft (2710') independently or in one or more groups. For example, the set of splines (2720') may be disposed within the catheter shaft (2710') in the first configuration. The splines (2720') may then be advanced out of the catheter shaft (2710') and transformed into the second configuration. The splines (2720') may be advanced all together or advanced such that the set of splines (2720') corresponding to the anode electrodes (2730) are advanced separately from the set of splines (2720') corresponding to the cathode electrodes (2730', 2740). In some embodiments, the splines (2710') may be advanced independently through respective lumens (e.g., sheaths) of the catheter shaft (2710'). In the second configuration, the electrodes (2730', 2740) are biased away from the catheter shaft (2710') longitudinally and/or laterally with respect to a longitudinal axis of a distal end of the catheter shaft (2710'). This may aid delivery and positioning of the electrodes (2730', 2740) against an endocardial surface. In some embodiments, each of the set of splines (2720') may extend from a distal end of the catheter shaft (2710') by up to about 5 cm.

In some embodiments, the distal electrodes (2730') may have the same polarity while adjacent proximal electrodes (2740) may have the opposite polarity as the distal electrodes (2730'). In this manner, an electric field may be generated between the distal and proximal electrodes.

In some of these embodiments, a handle (not shown) may be coupled to the set of splines. The handle may be configured for affecting transformation of the set of splines between the first configuration and the second configuration. In some embodiments, the electrical leads of at least two electrodes of the set of electrodes (2730', 2740) may be electrically coupled at or near a proximal portion of the ablation device, such as, for example, within the handle. In some embodiments, the electrodes (2730', 2740) may be electrically wired together in the handle of the device (2700'), so that these electrodes (2730', 2740) are at the same electric potential during ablation.

The set of electrodes (2730', 2740) may include an atraumatic shape to reduce trauma to tissue. For example, the electrodes (2730', 2740) may have an atraumatic shape including a rounded, flat, curved, and/or blunted portion configured to contact endocardial tissue. In some embodiments, the electrodes (2730', 2740) may be located along any portion of the spline (2720') distal to the catheter shaft (2710'). The electrodes (2730', 2740) may have the same or different sizes, shapes, and/or location along respective splines. One or more of the splines (2720') may include three or more electrodes.

In some embodiments, each of the electrodes (2730') on a spline (2720') may be configured as an anode while each of the electrodes (2730') on an adjacent spline (2720') may be configured as a cathode. In another embodiment, each of the electrodes (2730') on one spline may alternate between an anode and cathode with each of the electrodes of an adjacent spline having a reverse configuration (e.g., cathode and anode). In some embodiments a subset of electrodes may be electrically wired together in the handle of the device, so that these electrodes are at the same electric potential during ablation. In other embodiments, the size, shape, and spacing of the electrodes (2730) may differ as well. In some embodiments, adjacent distal electrodes (2730') and proximal electrodes (2740) may form an anode-cathode pair. For example, the distal electrodes (2730') may be configured as an anode and the proximal electrodes (2740) may be configured as a cathode.

The ablation device (2700') may include any number of splines, for example, 3, 4, 5, 6, 7, 8, 9, 10, 12, 14, 16, 18, 20, or more splines, including all values and sub-ranges in between. In some embodiments, the ablation device (2700') may include 3 to 20 splines. For example, the ablation device (2700) may include 6 to 12 splines.

In FIG. 27C, two electrodes (2730', 2740) are formed on a surface of each spline (2720') such that each spline (2720') includes two insulated electrical leads. The thickness of each spline may vary based on the number of electrodes formed on each spline (2720') which may correspond to the number of insulated electrical leads in the spline (2720'). The splines (2720') may have the same or different materials, thickness, and/or radius of curvature. For example, the thickness of each spline (2720') may reduce distally.

In this manner, the electrodes in the second configuration may be placed against, a section of endocardial tissue to directly generate lesions thereupon by activation of appropriate electrodes using any suitable combination of polarities for delivery of pulse waveforms for irreversible electroporation. For example, adjacent electrodes (2730', 2740) may be configured with opposite polarities.

As the electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail herein. It should be appreciated that the size, shape, and spacing of the electrodes on and between the splines may be configured to deliver contiguous/transmural energy to electrically isolate one or more pulmonary veins. In some embodiments, alternate electrodes may be at the same electric potential, and likewise for all the other alternating electrodes. Thus, ablation may be delivered rapidly with all electrodes activated at the same time. A variety of such electrode pairing options exists and may be implemented based on the convenience thereof.

Figure 28A:
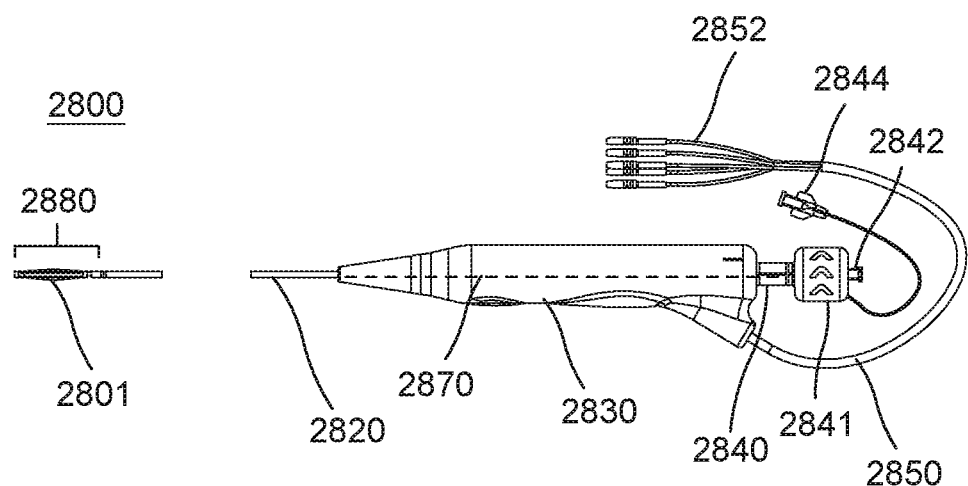
FIG. 28A is a side view of an ablation device, according to other embodiments.
Figure 28C:
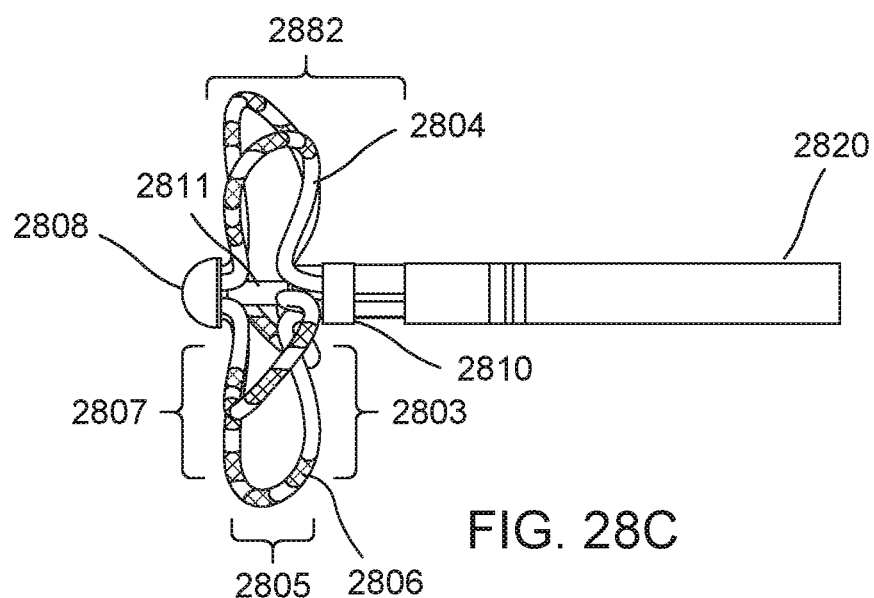
FIG. 28C is a detailed side view of a catheter of the ablation device of FIG. 28A in an expanded configuration, according to embodiments.
Figure 28D:
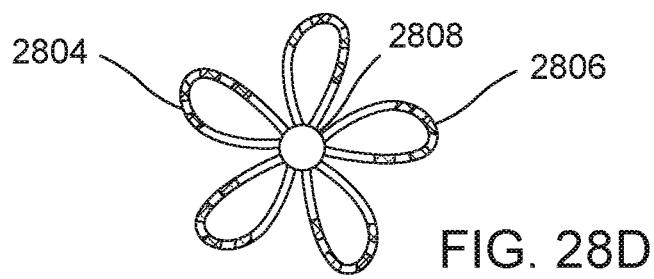
FIG. 28D is a front view of the catheter illustrated in FIG. 28C, according to embodiments.
Figure 29A:
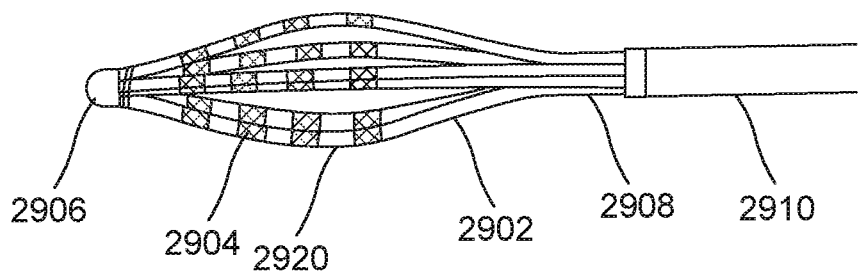
FIG. 29A is an image of a side view of a catheter of an ablation device, according to other embodiments.
Figure 29B:
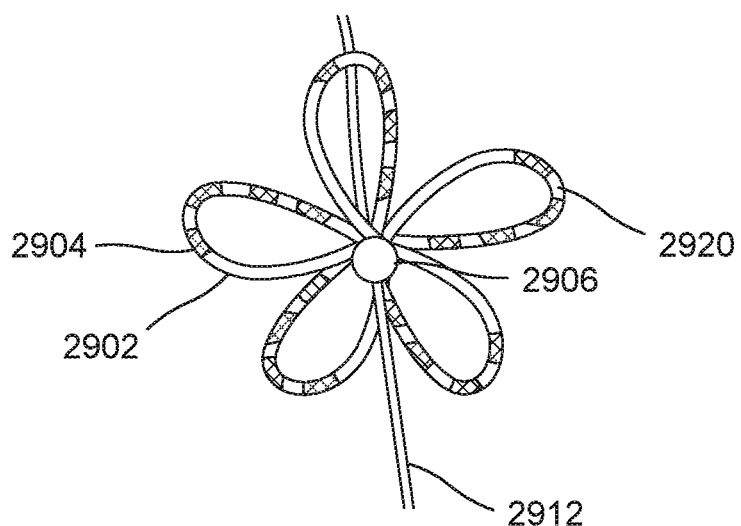
FIG. 29B is an image of a perspective view of the catheter of FIG. 29A, according to other embodiments.

FIG. 28A is a side view of an embodiment of an ablation device (2800) having a set of splines (2801) at a distal end of the device (2800) and a handle (2830) at a proximal end of the device (2800). Each spline of the set of splines (2801)

may include a flexible curvature so as to rotate, or twist and bend and form a petal or tear drop-shaped curve such as shown in FIGS. 29D and 29B. The ablation device (2800) may include a catheter shaft (2820) defining a first longitudinal axis and a shaft lumen therethrough. The set of splines (2801) may extend from a distal end of the shaft lumen. Each spline (2804) of the set of splines (2801) may include one or more electrodes (2806) formed on a surface of that spline (2804) (as shown in FIGS. 28C-28D). The distal ends of the set of splines (2801) may be tethered to a distal cap (2808) such that the splines (2801) and distal cap (2808) may translate relative to the catheter shaft (2820) (e.g., expand and contract together). For example, the set of splines (2801) may be configured for translation along the first longitudinal axis to transition between a first configuration and a second configuration, as discussed in more detail herein.

The catheter shaft (2820) may be coupled to a proximal end of the handle (2830). A diameter of the catheter shaft (2820) may be between about 6 French and about 15 French, including all values and sub ranges in between. In some embodiments, the catheter shaft (2820) may include a length of between about 60 cm and about 85 cm, including all values and sub ranges in between. The handle (2830) may define a second longitudinal axis (2870) and a handle lumen therethrough. The handle (2830) may be coupled to the set of splines (2801) and a distal cap (2808) (shown in FIG. 28C). The handle (2830) may include a translation member (2840) disposed in the handle lumen. The translation member (2840) may define a guidewire lumen (2842) therethrough. A proximal end of the translation member (2840) may include a knob (2841) configured for an operator to translationally and/or rotationally manipulate. For example, the translation member (2840) may be configured for translation along the second longitudinal axis (2870) to transition the ablation device (2800) between a set of configurations including the first and second configuration of the set of splines (2801).

In some embodiments, the handle (2830) may include a flush port (2844). The flush port (2844) may be used in some embodiments for saline irrigation. For example, a saline flow may be used to maintain a predetermined level of flow to prevent thrombus formation. An electrical cable (2850) may be coupled to the handle (2830) where a proximal end of the cable (2850) may include one or more connectors (2852). In some embodiments, the electrical cable (2850) may be relatively short (e.g., up to about one meter) to increase maneuverability and flexibility of the ablation device (2800). The connectors (2852) may be configured to couple to an extension cable (as described in more detail with respect to FIG. 31) that may be used to connect the ablation device (2800) to a signal generator such as an RF signal source and/or other components.

Figure 30A:
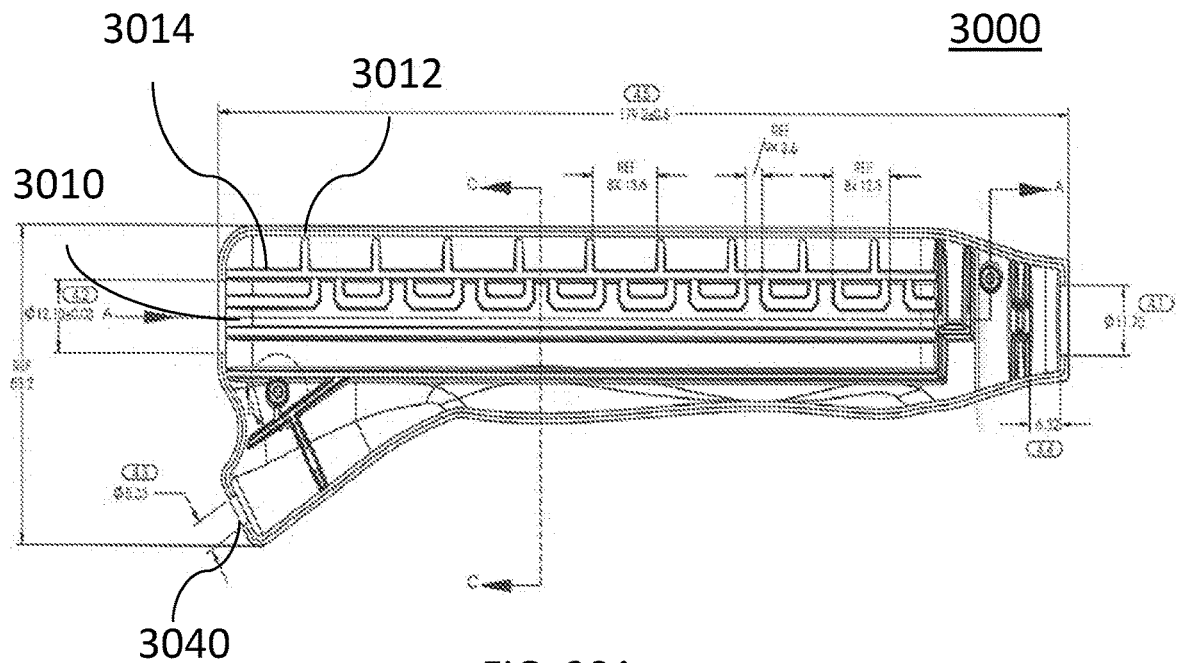
FIG. 30A is a cross-sectional side view of a handle of an ablation device, according to embodiments.
Figure 30B:
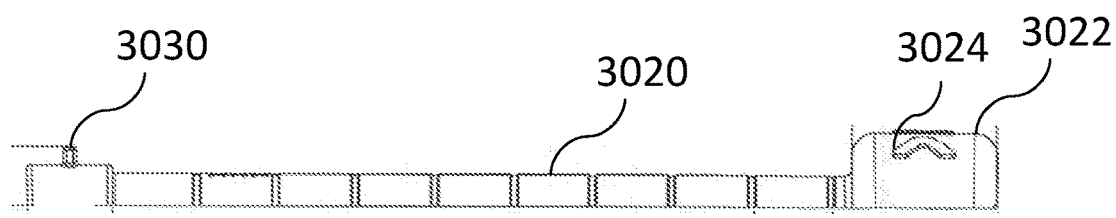
FIG. 30B is a cut-away side view of a translation member of the ablation device of FIG. 30A, according to embodiments.
Figure 30C:
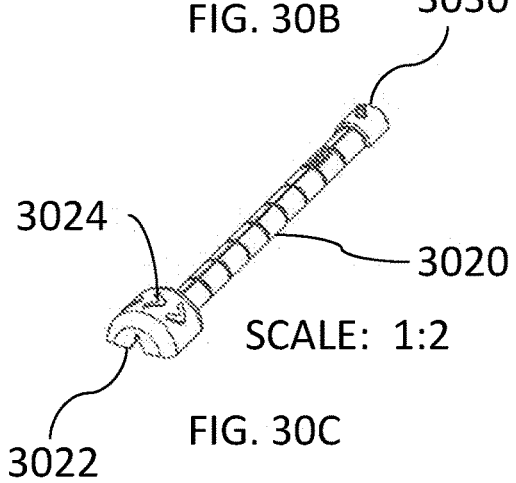
FIG. 30C is a cut-away perspective view of a translation member of FIG. 30B, according to other embodiments.

As discussed in more detail with respect to FIGS. 30A-30C, the translation member (2840) may be configured for rotation about the second longitudinal axis (2870) to transition between a lock state and an unlock state. The lock state may fix a translational position of the set of splines (2801) and the distal cap (2808) relative to the catheter shaft (2820) and the unlock state permits translation of the distal cap (2808) and set of splines (2801) relative to the catheter shaft (2820).

FIGS. 28A and 29A depict the set of splines (2801, 2902) in the first configuration where the set of splines (2801, 2902) define a longitudinally-extending cylinder. For example, each of the splines (2801) in the first configuration may include a concave curve facing the first longitudinal axis. The curve may be such that the set of splines (2801) may be advanced through vasculature. FIGS. 28C-28E and 29B illustrate the set of splines (2801, 2902) in the second configuration, where each spline includes a loop having a first concave curve (2803) facing the distal end of the set of splines (2801), a second concave curve (2805) facing the longitudinal axis, and a third concave curve (2807) facing the distal end of the shaft lumen (2820). Each loop of the set of splines (2801) may be described as a flower petal where the set of splines (2801) in the second configuration may be described as a forming a flower catheter (see FIGS. 28D and 29B).

In some embodiments, a distal cap (2808) may be coupled to a distal portion of each of spline of the set of splines (2801). The set of splines (2801) may be configured for translation along the first longitudinal axis to transition the splines (2801) between a first configuration (FIG. 28A) and a second configuration (e.g., FIG. 28C). In the first configuration, the distal cap (2808) may be coupled to a distal end of the catheter shaft (2820) at a first distance (2880). In the second configuration, the distal cap may be coupled to a distal end of the catheter shaft at a second distance (2882). In some embodiments, a ratio of the first distance to the second distance may be between about 5:1 and about 25:1.

Figure 28B:
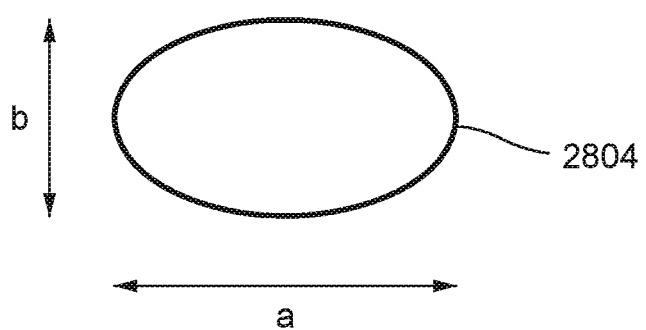
FIG. 28B is a cross-sectional view of a spline of the ablation device of FIG. 28A, according to embodiments.
Figure 28E:
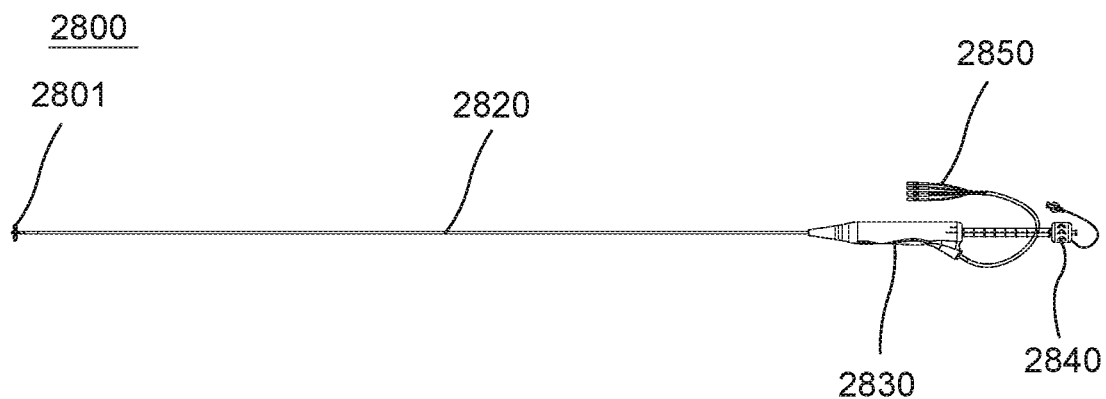
FIG. 28E is a side view of the ablation device of FIG. 28A with the catheter of the ablation device being in the expanded configuration illustrated in FIG. 28C, according to other embodiments.

FIG. 28B illustrates a cross-sectional view of a spline (2804) of the ablation device (2800) depicted in FIG. 28A. Generally, a cross-section of each spline (2804) of the set of splines (2801) may have the shape of an ellipse. In some embodiments, the ellipse shape may have a major axis length (a) between about 1 mm and about 4 mm and a minor axis length (b) between about 0.4 mm and about 3 mm. For example, the major axis length (a) of the ellipse may be between about 1 mm and about 2.5 mm and the minor axis length (b) may be between about 0.4 mm and about 1.2 mm. The minor axis may intersect the first longitudinal axis of the catheter shaft. These dimensions may help the splines resist kinking, bunching of the spines, and aid bending of the spline into the second configuration (e.g., petal shape). For example, the shorter minor axis may aid bending (e.g., buckling) of the spline in a radial direction and the longer major axis may provide lateral rigidity to the spline. In some embodiments, each spline (2804) of the set of splines (2801) may have a cross-sectional area between about 0.2 $mm^2$ and about 15 $mm^2$.

In some embodiments, when the set of splines (2801) transition between the first configuration and the second configuration, each spline (2801) may change shape (e.g., compress, expand). For example, a length of the major axis (a) may increase in the transition from the first configuration to the second configuration. In some embodiments, a spline (2801) in the first configuration may have a first major axis length and in the second configuration may have a second major axis length. A ratio of the first major axis length to the second major axis length may be between about 4:5 and about 1:4.

FIG. 28C is a detailed side view of an embodiment of an ablation device (2800). The catheter shaft (2820) may define a shaft lumen through which one or more of a set of splines (2801), distal cap (2808), and guidewire may be disposed and advanced through. A set of splines (2801) may extend from a distal end of the catheter shaft (2820). In some embodiments, a portion of the set of splines (2801) may be fixed to the distal end of the catheter shaft (2820). Each of the distal portions of the set of splines (2804) may be fixed to a distal cap (2808). The distal cap (2808) may include an atraumatic shape. In some embodiments, the distal cap (2808) may define a cap lumen therethrough configured to receive a guidewire (2811) therethrough (see FIG. 29B). A distance between the distal cap (2808) and the catheter shaft (2820) may be less than about 8 mm.

Each spline (2804) of the set of splines (2801) may include a set of independently addressable electrodes (2806). In some embodiments, each spline (2804) may include a set of electrodes having from two electrodes to eight electrodes. As the electrodes (2806) may be independently addressable, the electrodes (2806) may be energized in any sequence using any pulse waveform sufficient to ablate tissue by irreversible electroporation. For example, different sets of electrodes (2806) may deliver different sets of pulses (e.g., hierarchical pulse waveforms), as discussed in further detail herein. It should be appreciated that the size, shape, and spacing of the electrodes (2806) on and between the splines (2804) may be configured to deliver contiguous/transmural energy to electrically isolate one or more pulmonary veins. In some embodiments, alternate electrodes may be at the same electric potential, and likewise for all the other alternating electrodes. Thus, ablation may be delivered rapidly with all electrodes activated at the same time. A variety of such electrode pairing options exists and may be implemented based on the convenience thereof.

In some embodiments, a first set of electrodes of a first spline of the set of splines (2801) may be configured as an anode and a second set of electrodes of a second spline of the set of splines (2801) may be configured as an anode. The first spline may be non-adjacent to the second spline. This may increase the spacing between the splines and help prevent a short-circuit. In some of these embodiments, the first set of electrodes may include one electrode and the second set of electrodes may include at least two electrodes.

The set of electrodes (2806) may include an atraumatic shape to reduce trauma to tissue. For example, the electrodes (2806) may have an atraumatic shape including a rounded, flat, curved, and/or blunted portion configured to contact endocardial tissue. In some embodiments, the electrodes (2806) may be located along any portion of the spline (2804) distal to the catheter shaft (2820). The electrodes (2806) may have the same or different sizes, shapes, and/or location along respective splines. One or more of the splines (2806) may include three or more electrodes. In some embodiments, each electrode (2806) of the set of electrodes may have a surface area between about 0.5 mm$^2$ and about 20 mm$^2$.

In some embodiments, each spline (2804) of the set of splines (2801) may define a spline lumen therethrough and each electrode (2806) of the set of electrodes may have an insulated electrical lead associated therewith (not shown). The insulated electrical leads may be disposed in the spline lumen of the spline (2804) associated with that electrode (2806). For example, each insulated electrical lead may be configured for sustaining a voltage potential of at least about 700 V without dielectric breakdown of its corresponding insulation. The electrodes (2806) on each of the splines (2804) in the second configuration may be electrically isolated from each other. In some embodiments, the set of electrodes (2806) for each spline (2804) may be jointly wired. In some embodiments, the set of electrodes (2806) for each spline (2804) may be wired in series. For example, a set of four electrodes on a spline (2804) may be electrically coupled together using a single lead. The electrical lead may be disposed within a spline lumen to electrically couple to each of the four electrodes. The set of electrodes (2806) for each spline (2804) in the set of splines (2801) may be coupled to a corresponding insulated electrical lead. For example, the electrical lead connected to the four electrodes through corresponding apertures in the spline.

A spline having a set of anode electrodes (2806) may be activated together to deliver pulse waveforms for irreversible electroporation. Electrodes on other splines may be activated together as cathode electrodes on their respective splines so at to form an anode-cathode pairing for delivery of pulse waveforms for irreversible electroporation. The anode-cathode pairing and pulse waveform delivery can be repeated sequentially over a set of such pairings.

For example, the splines (2801) may be activated sequentially in a clockwise or counter-clockwise manner. As another example, the cathode splines may be activated sequentially along with respective sequential anode spline activation until ablation is completed, as may be determined using electrophysiology data as discussed herein. In embodiments where electrodes on a given spline are wired separately, the order of activation within the electrode of each spline may be varied as well. For example, the electrodes in a spline may be activated all at once or in a predetermined sequence.

In some embodiments, one or more splines of the set of splines (2801) in the second configuration may have a radius of curvature that varies along a spline length of that spline (2801). In some embodiments, one or more splines of the set of splines (2801) in the second configuration may have a radius of curvature that decreases and then increases along a spline length of that spline (2804). In some embodiments, the ablation device (2800) may include one or more radiopaque portions (2810) that may be fluoroscopically imaged to aid an operator in positioning the ablation device (2900) within one or more body cavities of the patient. As shown in FIG. 28C, the radiopaque portion (2810) may include a radiopaque marker band disposed over the set of splines (2801) at a portion extending beyond a distal end of the catheter shaft (2820). Additionally or alternatively, one or more of a distal portion of the catheter shaft (2820) and the distal cap (2808) may include a radiopaque portion (2810).

FIG. 28D is a front view of an embodiment of an ablation device (2800) in the second configuration. Each spline (2804) of the set of splines (2801) may be coupled to a distal cap (2808) and form a plurality of petal-like curves that together resemble a flower. In this manner, the set of splines (2804) twist, bend and bias away from the longitudinal axis of the ablation device (2600), thus allowing the splines (2804) to more easily conform to the geometry of an endocardial space, and particularly adjacent to the opening of a pulmonary vein or antrum. When viewed from the front as in FIG. 28D, each of the splines (2804) displays an angle between the proximal and distal ends of the curve of more than 180 degrees.

In some embodiments, one or more splines of the set of splines (2804) in the second configuration may bias away from the longitudinal axis of the catheter shaft (2820) by up to about 30 mm. In other embodiments, one or more splines (2804) of the set of splines (2801) in the second configuration may have a cross-sectional diameter between about 10 mm and about 50 mm. In some embodiments, one or more splines of the set of splines (2804) in the second configuration may have a cross-sectional diameter between about 25 mm and about 35 mm. For example, one or more splines of the set of splines (2804) in the second configuration may have a cross-sectional diameter of about 27-28 mm or about 35 mm. One or more splines of the set of splines (2804) in the second configuration may have a cross-sectional diameter of about 30 mm.

FIG. 28E is a side view of an embodiment of an ablation device (2800) including a set of splines (2801) in a second configuration and the set of splines coupled to the catheter shaft (2802). A proximal end of the catheter shaft (2820) may be coupled to a distal end of the handle (2830). The handle (2830) may include a translation member (2840) and an electrical cable (2850). In some embodiments, the set of splines (2804) and the distal cap (2808) may be configured for translation along the first longitudinal axis by up to about 60 mm.

FIG. 29A is a detailed side view of an embodiment of an ablation device (2900) in a first configuration. The ablation device (2900) may include a catheter shaft (2910) defining a shaft lumen therethrough. A set of splines (2902) may extend from a distal end of the catheter shaft lumen with each spline (2902) including one or more electrodes (2904) formed on a surface of that spline (2902). A distal cap (2906) may be coupled to a distal portion of each spline (2902). One or more of a distal portion of the catheter shaft (2910), the set of splines (2902), and the distal cap (2906) may include a radiopaque portion (2908). The radiopaque portion (2908) may be fluoroscopically imaged to aid an operator in positioning the ablation device (2900) within one or more body cavities of the patient. The radiopaque portion may be formed on a surface of a spline (2902).

The set of splines (2902) in the first configuration may be arranged to rotate about the longitudinal axis in a helical configuration. The helical configuration of the set of splines (2902) may bias the set of splines towards transitioning to a second configuration forming a set of loops (e.g., petals) spaced-apart from each other. This may help prevent the set of splines from undesirably bunching together. In some embodiments, each spline of the set of splines (2902) may have a helix angle of less than about 5 degrees relative to the longitudinal axis of the catheter shaft (2910). As used herein, the helix angle is the angle of a spline (2902) relative to the longitudinal axis of the catheter shaft (2910). In other embodiments, each spline of the set of splines (2902) may have a helix angle of less than about 2 degrees relative to the longitudinal axis of the catheter shaft (2910). In other embodiments, each spline of the set of splines (2902) may have a helix angle of less than about 1 degrees relative to the longitudinal axis of the catheter shaft (2910).

FIG. 29B is a perspective view of an embodiment of an ablation device (2900) in a second configuration. The distal cap (2906) may define a cap lumen therethrough where the cap lumen may be configured to receive a guidewire (2912) therethrough. The ablation device (2900) may be slidably advanced over the guidewire (2912) so as to be disposed over the guidewire (2912) during use. The distal portion of the guidewire (2912) disposed in a lumen (e.g., near a pulmonary vein ostium) may serve as a backstop to advancement of a distal portion of the ablation device (2900). The guidewire (2912) may be slidable within a lumen of the ablation device (2900). FIG. 29B shows a guidewire (2912) disposed through a distal cap lumen of the distal cap (2906). The set of splines (2902) in the second configuration may be arranged as a set of non-overlapping loops. Each spline of the set of splines (2902) in the second configuration may be characterized by a midpoint of that spline being furthest from the longitudinal axis relative to the rest of the spline. This midpoint in the second configuration may be where that spline has the greatest curvature. It is noted that the midpoint may not necessarily be at the halfway point of the portion of the spline (2902) extending between the distal cap (2906) and distal end of the catheter shaft (2910). As shown in FIGS. 29A-29B, the set of electrodes (2904) of each of the splines (2902) may be unequally distributed with respect to the midpoint of the spline (2902). Unequal distribution of electrodes (2904) on each spline may better align the electrical field generated by the electrodes (2904) with the myocardial cells to be ablated and may also improve separation of ablation zones generated by each spline. For example, the set of electrodes (2904) may be distributed proximal and distal to the midpoint by a ratio of 1 to 3. In other embodiments, the set of electrodes (2904) may be distributed proximal and distal to the midpoint by a ratio of 1 to 2 or a ratio of 2 to 3.

The set of electrodes for each spline of the set of splines may include at least one electrode configured for ablation and at least one other electrode configured for receiving an ECG signal. In some embodiments, one or more electrodes configured for ablation and one or more electrodes configured for receiving an ECG signal may be coupled to separate insulated electrical leads. For example, the set of electrodes may include four electrodes for ablation and one electrode for receiving the ECG signal. The four ablation electrodes may be wired separately from the one ECG electrode. In some embodiments, one or more electrodes of each spline of the set of splines may be alternatively configured for ablation and for receiving ECG signals. For example, for a set of five electrodes, all five electrodes may be used for ablation and one of the electrodes (e.g., adjacent to the midpoint) may be used for receiving an ECG signal when not used for ablation.

In embodiments where the set of electrodes are unequally distributed relative to a midpoint, the electrode closest to the midpoint (2920) may configured for receiving an ECG signal and coupled to a separate electrical lead. For example, the electrode closest to the midpoint on the side having more electrodes may be configured for receiving an ECG signal. This electrode may be disposed near a maximum diameter of the ablation device in the second configuration that may have good contact with tissue, thereby aiding reception of an ECG signal.

In some embodiments, the set of splines may include between about 3 splines and about 20 splines. For example, the set of splines may include 5 splines (FIGS. 28A-28E) or 8 splines (FIGS. 26A-26D). The guidewire may include stainless steel, nitinol, platinum, or other suitable, biocompatible materials. Platinum is radiopaque and its use may increase flexibility to aid advancement and positioning of the ablation device within an endocardial space.

Each of the electrodes of the ablation devices discussed herein may be connected to an insulated electrical lead (not shown) leading to a handle (not shown) coupled to a proximal portion of the catheter. FIG. 30A is a cross-sectional side view of a handle (3000). The handle (3000) may be coupled to a proximal end of a catheter shaft and set of splines (not shown). The handle (3000) may define a second longitudinal axis and a handle lumen (3010) therethrough. FIG. 30B-30C are cut-away side and perspective views of a translation member (3020) having a knob (3022). A proximal end of the translation member (3020) may include a knob (3022) configured for an operator to translationally and/or rotationally manipulate. For example, the translation member (3020) may be configured for translation along the second longitudinal axis to transition the ablation device between a set of configurations including the first and second configuration of the set of splines.

The translation member (3020) may be configured for rotation about the second longitudinal axis to transition between a lock state and an unlock state. The lock state may fix a translational position of a set of splines and distal cap relative to a catheter shaft and the unlock state may permit translation of the set of splines and distal cap relative to the catheter shaft.

The handle (3000) may include the translation member (3020) disposed in the handle lumen. The translation member (3020) may include a locking member (3030), a knob (3022) configured for an operator to manipulate, and an optional set of indicia (3024) to aid the operator in manipulating the handle (3000). The handle lumen (3010) may define a translation groove (3014) configured for translation of the locking member (3030) along the translation groove (3014) and a plurality of locking grooves (3012) each intersecting the translation groove (3014). For example, the translation groove (3014) may be parallel to the second longitudinal axis and the plurality of locking grooves (3012) may be perpendicular to the second longitudinal axis. The locking member (3030) may include one or more protrusions configured to translate through the translation groove (3012) and plurality of locking grooves (3014). The locking member (3030) may be configured for translation along the translation groove (3014) to transition the set of splines between a first and second configuration. The locking member (3030) disposed in a distal locking groove (3012) may correspond to the set of splines in the first configuration while the locking member (3030) disposed in a proximal locking groove (3012) may correspond to the set of splines in the second configuration.

In some embodiments, the ablation device may be advanced into a patient in a lock state with the set of splines in the first configuration. For example, the locking member (3030) may be disposed in a distal locking groove (3012) such that portions of the translation member (3020) distal to the knob (3022) may be disposed in the handle lumen (3010). To transition the set of splines from the first configuration to the second configuration, the operator may rotate the knob (3022) about the second longitudinal axis to translate the locking member (303) out of the distal locking groove (3012) and into the translation groove (3010). The operator may then translate the translation member (3020) proximally to a desired locking groove (3012) such as a proximal locking groove or intermediate locking groove. The knob (3022) may be rotated in the opposite direction about the second longitudinal axis to translate the locking member (3030) into the desired locking groove (3012). The set of splines may thus be securely transitioned from one locked spline configuration to another locked spline configuration. As the translation member (3020) is pulled out of the handle (3000), the set of splines may bias away from the first longitudinal axis. Between the first and second configurations, the set of splines may form a basket-like and/or flower-like shape of variable diameter. In some embodiments, the handle may include seven locking grooves (3012). In some embodiments, translation of the set of splines relative to a catheter shaft may be linear with respect to translation of the translation member (3020) relative to the handle (3000). The set of splines may be deployed and undeployed from the second configuration as desired. In some embodiments, the helix angle of the set of splines may be independent of the rotation of the translation member about the second longitudinal axis.

In some embodiments, a handle (3000) may be coupled to a proximal portion of the catheter (not shown) and may include a bending mechanism (e.g., one or more pull wires (not shown)) configured to modify the shape of a distal portion of the catheter.

Figure 31:
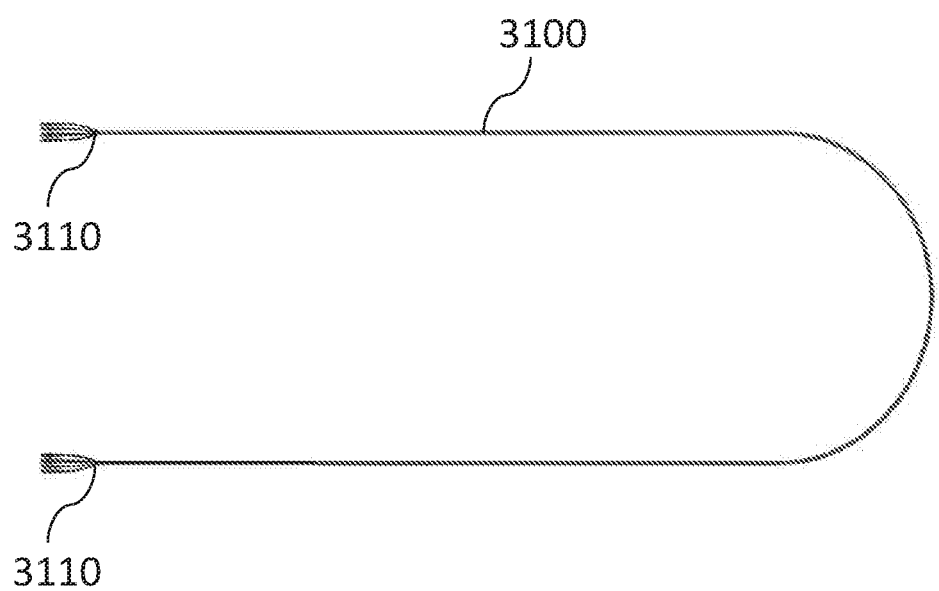
FIG. 31 is a side view of an extension cable useable with the ablation device of FIG. 28A, according to embodiments.

FIG. 31 is a side view of an electrical extension cable (3100) that may be used to electrically couple a signal generator to a proximal end of a handle of an ablation device. A proximal and distal end of the extension cable (3100) may include one or more connectors (3110). The connectors (3110) may be configured to couple to a corresponding connector on an ablation device and signal generator such as an RF signal source and/or other components. In some embodiments, each spline may be associated with an insulated electrical lead such that an ablation device having five splines with five leads may electrically connect to five corresponding connectors (3110) at a distal end of the extension cable (3100). Individual connectors allow for current measurement during energy delivery. In some embodiments, the proximal and distal ends of the extension cable (3100) may each include a single connector with a set of pins corresponding to the set of electrical leads of the ablation device (e.g., five pins for an ablation device having five splines). In some embodiments, the connectors may have the same gender. In some embodiments, the extension cable may have a length of between about 1 meter and about 10 meters. For example, the extension cable may have a length of about 3 meters.

Figure 32A:
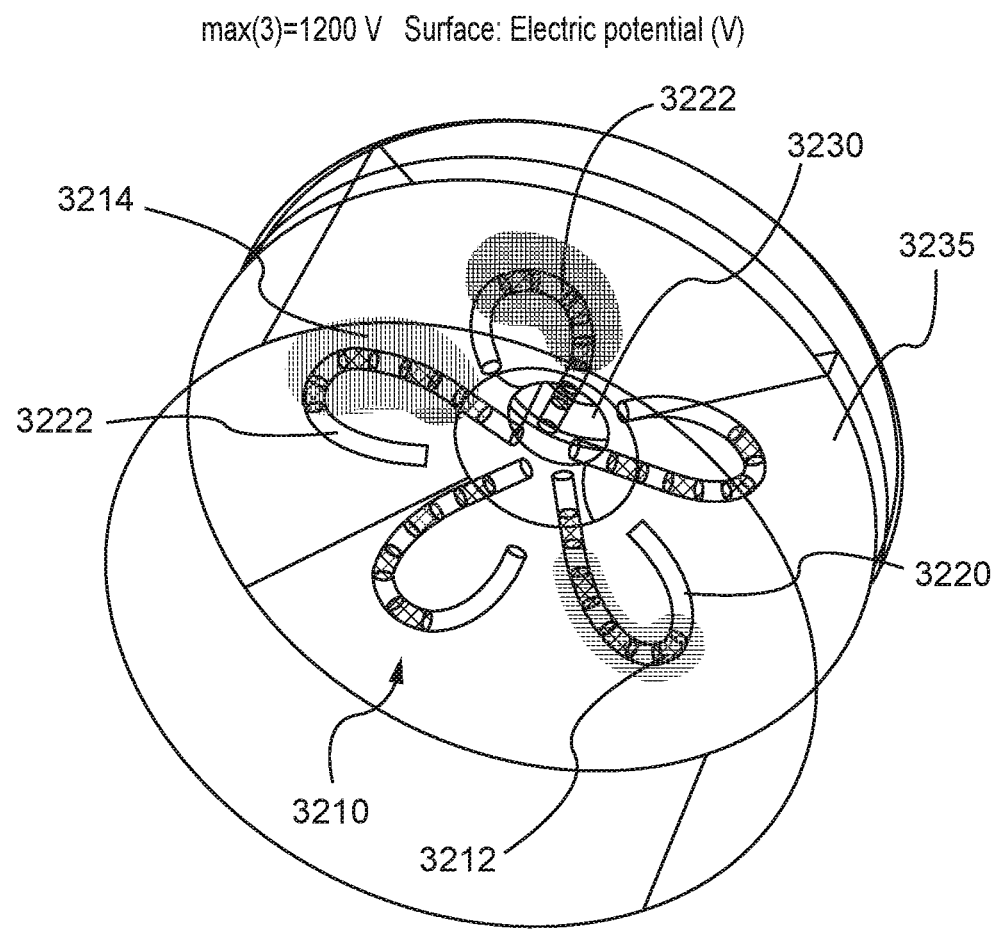
FIGS. 32A-32B are perspective views of an ablation device in a pulmonary vein ostium, according to embodiments.
Figure 32B:
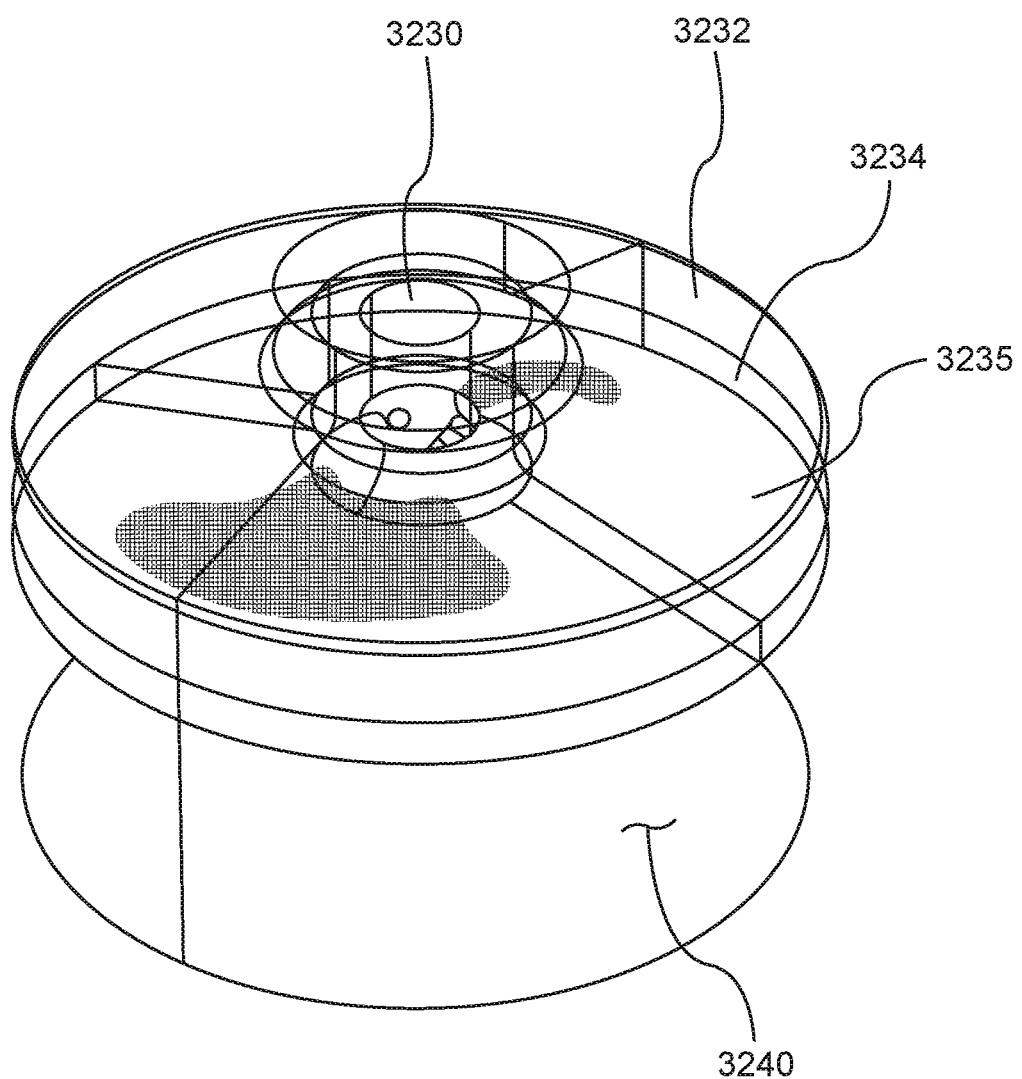

FIGS. 32A-32B are perspective views of an ablation device (3210) disposed in a pulmonary ostium (3230). FIG. 32A illustrates a perspective view of an atrial inner surface (3235) and the ablation device (3210) disposed in contact with the pulmonary vein ostium (3230). FIG. 32A illustrates a spline (3220) having one or more electrodes configured as anodes, and two splines (3222) each having one or more electrodes configured as cathodes. FIG. 32B similarly illustrates the pulmonary antrum (3230), pericardium (3232), atrial wall (3234), atrial inner surface (3235), and blood pool (3240). As shown in FIG. 32B, for example, an ablation device (3210) in the second configuration may be located in contact with a pulmonary vein ostium (3230). A first set of electrodes (3212) on a first spline may be configured as an anode (3220) and a second set of electrodes (3214) on a second spline non-adjacent to the first spline may be configured as a cathode (3222). When the splines are in contact with tissue, the set of splines may form an umbrella-like shape.

Figure 32C:
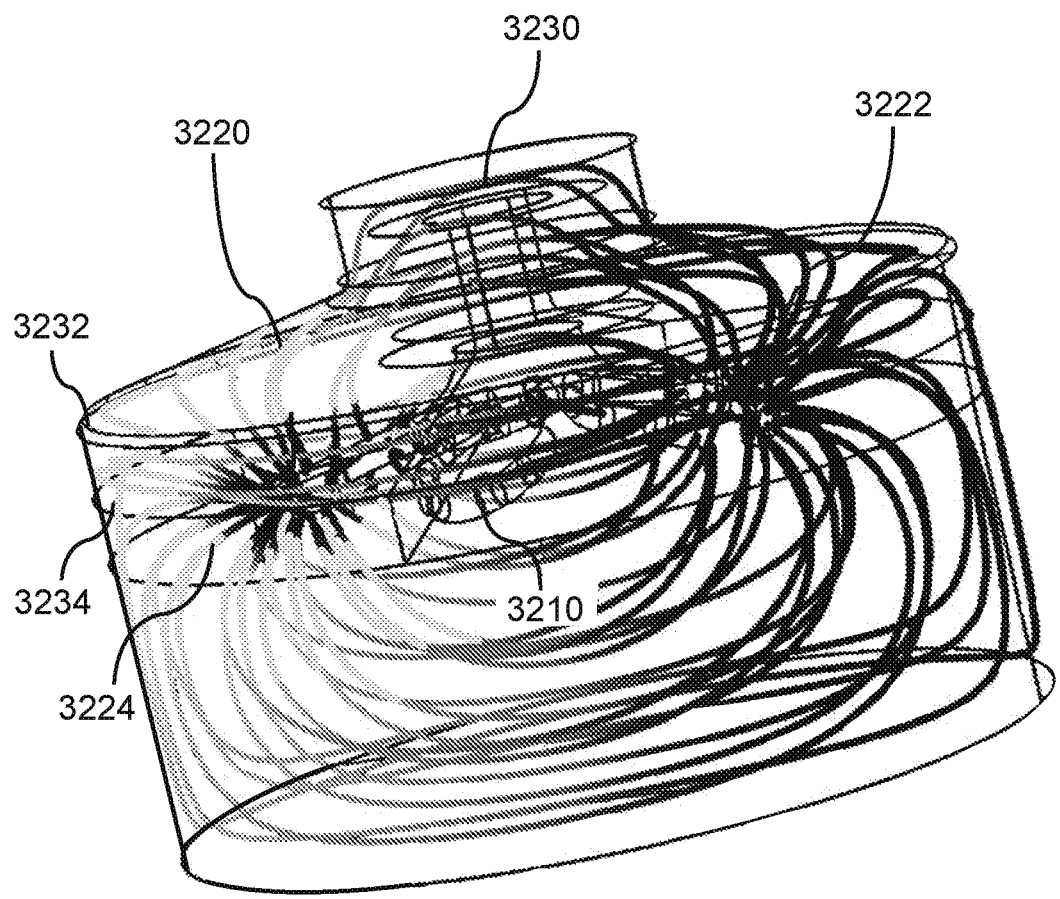
FIGS. 32C-32D illustrate simulations of current density of an ablation device in the region of a pulmonary vein antrum, according to embodiments.
Figure 32D:
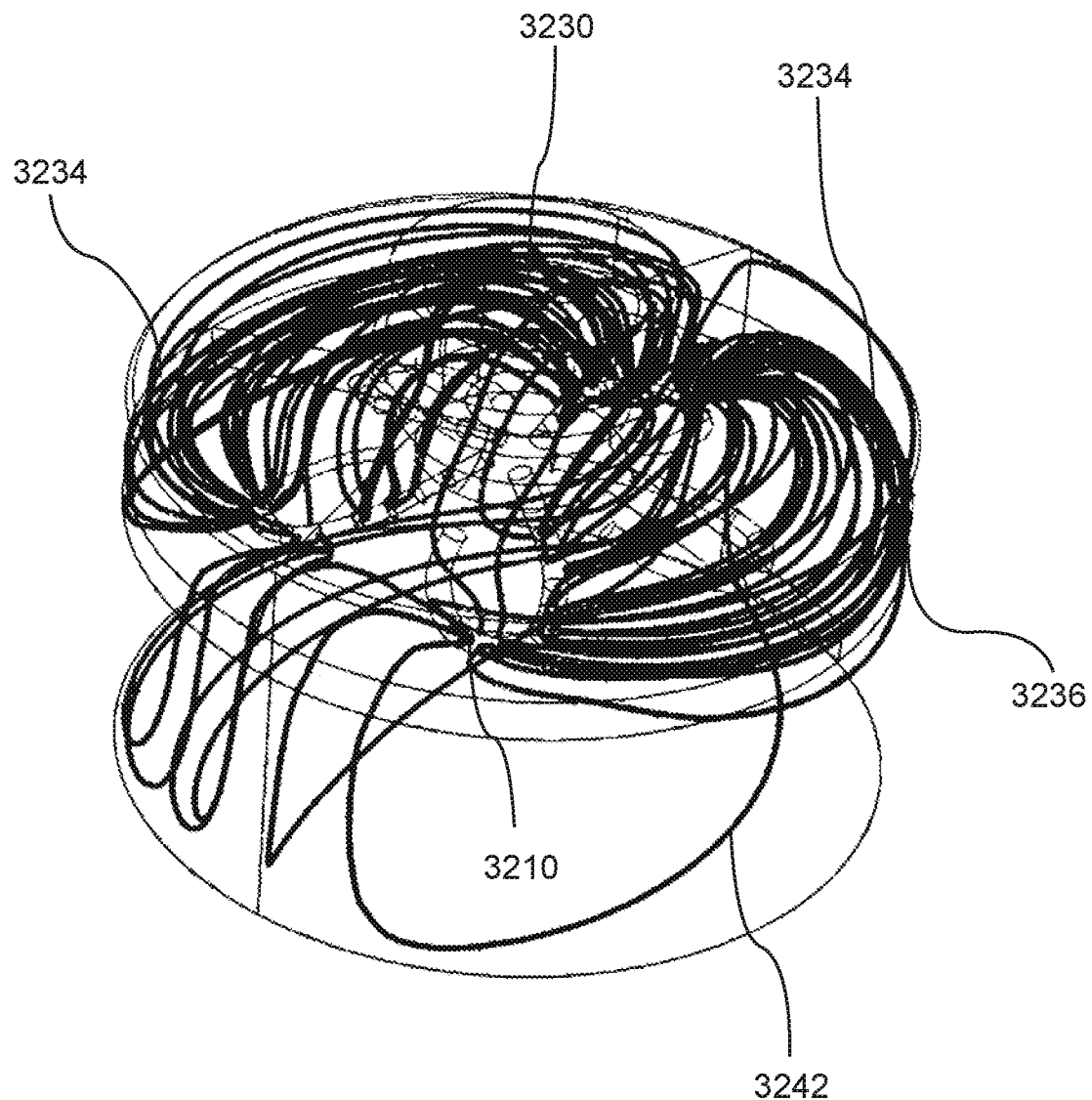

FIGS. 32C-32D are perspective views of a pulmonary ostium (3230) illustrating simulated current density (3224) based on application of an ablation catheter (3210). In FIGS. 32C and 32D, the ablation device (3210) receiving a pulse waveform may generate a set of electric field lines (3224) from the anode (3220) to the cathode (3222). The density of the field lines (3224) corresponds to current density, which in turn is proportional to electric field strength. The tissue shown in FIG. 32C includes a thin, funnel-shaped layer of pericardium (3232) adjacent to a section of atrial wall (3234). As illustrated, the set of electric field lines in the atrial wall (3234) may be substantially circumferential or locally tangential to the atrial wall. The atrial wall (3234) may include a set of myocardial cells that extend in a circumferential direction. The myocardial cells are relatively long and may define a longitudinal axis aligned circumferentially with the atrial wall. In some embodiments, when the magnitude of the electric field lines is E and a magnitude of a tangential component of the electric field lines relative to the atrial wall (3234) is $E_t$, then for some embodiments, $E_t/E$ is greater than about 0.3 in a substantial portion of the atrial wall (3234) between the anode (3234) and cathode (3222) splines. In other embodiments, $E_t/E > \frac{1}{2}$ in a substantial portion of the atrial wall (3234) between the anode (3234) and cathode (3222) splines The ablation device (3210) in the second configuration may be configured to generate a set of circumferential electric field lines that are generally parallel and intersect densely with a longitudinal axis of a set of myocardial cells disposed circumferentially in the atrial wall (3234). The current density is higher along the atrial wall (3234) and less within the pulmonary vein and a distance increases from the atrial wall (3234). As shown in FIG. 32D, the electric field lines (3236) within the atrial wall (3234) are much denser than the electric field lines (3242) in the blood pool (3240). This allows energy to be delivered more efficiently to tissue to ablate tissue and thus permits a reduction in energy delivered. For example, tissue ablation may be provided using a pulse waveform between about 500 V and 3,000 V, which in some cases may be half of the voltage otherwise needed to ablate tissue. Therefore, the preferential circumferential distribution of electric field lines through the atrial wall may be generated by the ablation device due to the configuration of the splines and electrodes associated therewith.

Balloon

Figure 10:
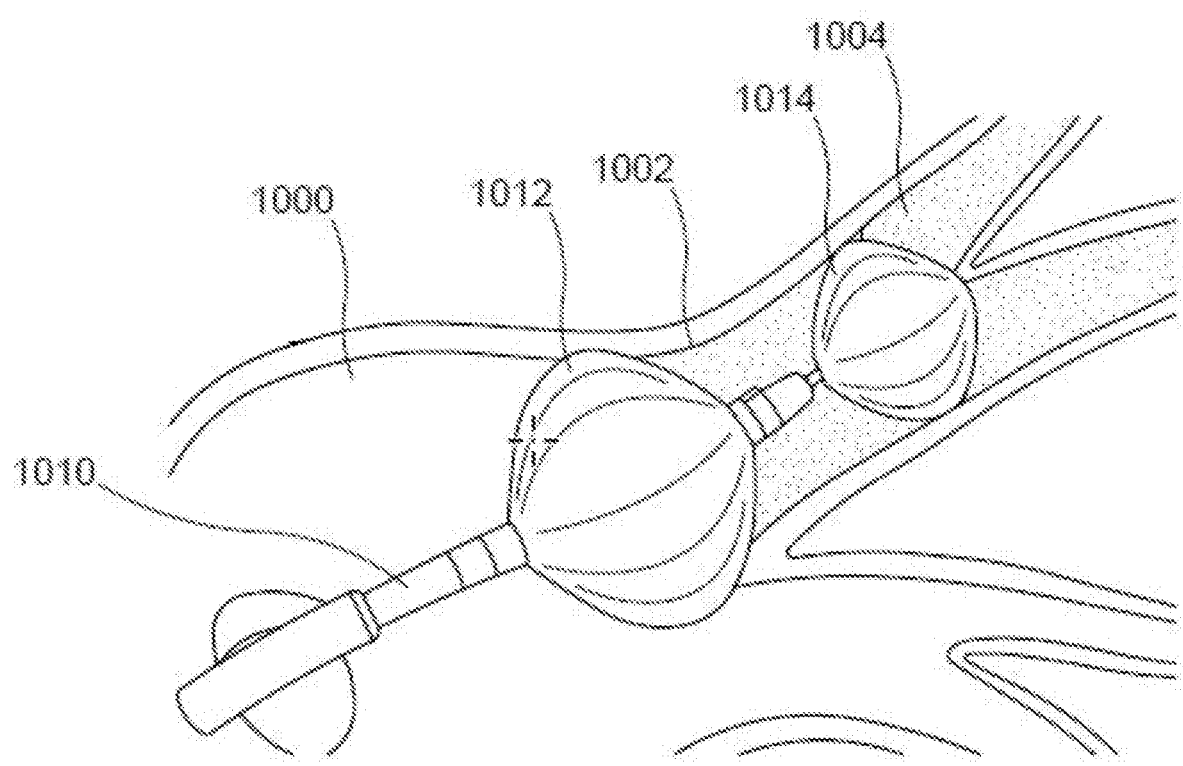
FIG. 10 is a perspective view of a balloon ablation catheter disposed in a left atrial chamber of a heart, according to other embodiments.

In some embodiments, an ablation device may include one or more balloons for delivering energy to ablate tissue by irreversible electroporation. FIG. 10 depicts an embodiment of a balloon ablation device (1010) (e.g., structurally and/or functionally similar to the ablation device (110)) disposed in a left atrial chamber (1000) of a heart. The ablation device (1010) may include a first balloon (1012) and a second balloon (1014) which may be configured to be disposed in an ostium (1002) of a pulmonary vein (1004). The first balloon (1012) in an expanded (e.g., inflated) configuration may have a larger diameter than the second balloon (1014) in an expanded configuration. This allows the second balloon (1014) to be advanced and disposed further into the pulmonary vein (1014) while the first balloon (1012) may be disposed near and/or at an ostium (1002) of the pulmonary vein (1004). The inflated second balloon serves to stabilize the positioning of the first balloon at the ostium of the pulmonary vein. In some embodiments, the first balloon (1012) and the second balloon (1014) may be filled with any suitable conducting fluid such as, for example, saline. The first balloon (1012) and the second balloon (1014) may be electrically isolated from each other. For example, each balloon (1012, 1014) may include an insulated electrical lead associated therewith, with each lead having sufficient electrical insulation to sustain an electrical potential difference of at least 700V across its thickness without dielectric breakdown. In other embodiments, the insulation on each of the electrical leads may sustain an electrical potential difference of between about 200 V to about 2500 V across its thickness without dielectric breakdown, including all values and sub-ranges in between. For example, a lead of the second balloon (1014) may be insulated as it extends through the first balloon (1012).

In some embodiments, the first and second balloons (1012, 1014) may form an anode-cathode pair. For example, in one embodiment, the first and second balloons may carry electrically separate bodies of saline fluid, and the first balloon (1012) may be configured as a cathode and the second balloon (1014) may be configured as an anode, or vice versa, where electrical energy may be capacitively coupled across the balloon or saline-filled electrodes. The device (1010) may receive a pulse waveform to be delivered to tissue (1002). For example, one or more of a biphasic signal may be applied such that tissue may be ablated between the first balloon (1012) and the second balloon (1014) at a desired location in the pulmonary vein (1004).

The first and second balloons (1012, 1014) may confine the electric field substantially between the first and second balloons (1012, 1014) so as to reduce the electric field and damage to tissue away from the ostium (1002) of the pulmonary vein (1004). In another embodiment, one or both of electrodes (1018) and (1019) disposed respectively proximal to and distal to the first balloon may be used as an electrode of one polarity, while the fluid in the first balloon may act as an electrode of the opposite polarity. A biphasic pulse waveform may then be delivered between these electrodes of opposed polarities by capacitive coupling across the balloon, resulting in a zone of irreversible electroporation ablation in the region around the first balloon. In some embodiments, one or more of the balloons (1012, 1014) may include a wire mesh.

Figure 11:
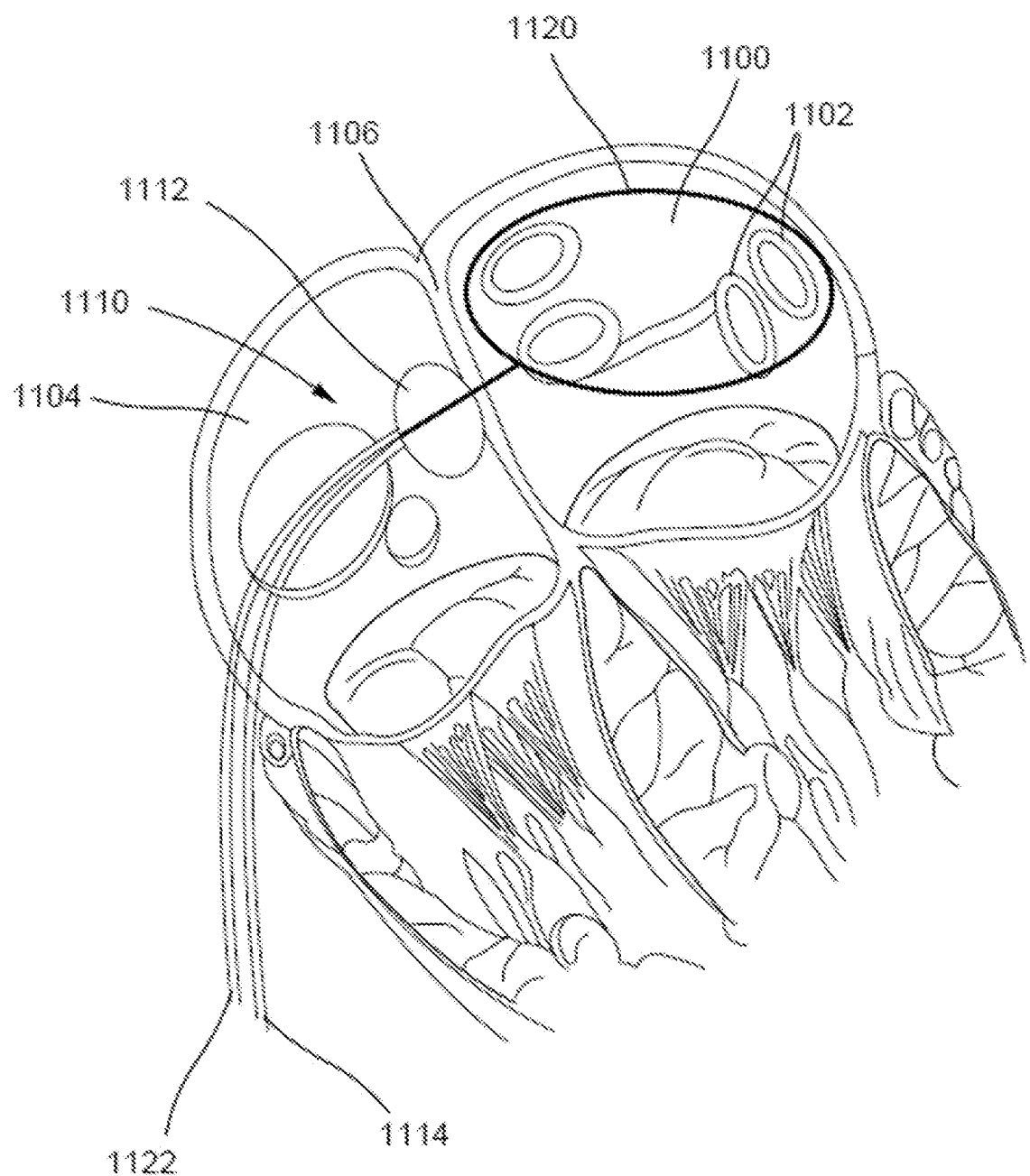
FIG. 11 is a cross-sectional view of a balloon ablation catheter disposed in a left atrial chamber of a heart, according to other embodiments.

FIG. 11 is a cross-sectional view of another embodiment of a balloon ablation device (1110) (e.g., structurally and/or functionally similar to the ablation device (1010)) disposed in a left atrial chamber (1100) and a right atrial chamber (1104) of a heart. The ablation device (1110) may include a balloon (1112) which may be configured to be advanced into and disposed in the right atrial chamber (1104). For example, the balloon (1112) may be disposed in contact with a septum (1106) of the heart. The balloon (1112) may be filled with saline. The device (1110) may further include an electrode (1120) that may be advanced from the right atrial chamber (1104) through the balloon (1112) and the septum (1106) and into the left atrial chamber (1100). For example, the electrode (1120) may extend from the balloon (1112) and puncture through the septum (1106) and be advanced into the left atrial chamber (1100). Once the electrode (1120) is advanced into the left atrial chamber (1100), a distal portion of the electrode (1120) may be modified to form a predetermined shape. For example, a distal portion of the electrode (1120) may include a nonlinear shape such as a circle, ellipsoid, or any other geometric shape. In FIG. 11, the distal portion of the electrode (1120) forms a loop that may surround a single ostium or two or more ostia of the pulmonary veins (1102) in the left atrial chamber (1100). In other embodiments, the distal portion of the electrode (1120) may have about the same diameter as an ostium of the pulmonary vein (1102).

The balloon (1112) and the electrode (1120) may be electrically isolated from each other. For example, the balloon (1112) and the electrode (1120) may each include an insulated electrical lead (1114, 1122) respectively, with each lead (1114, 1122) having sufficient electrical insulation to sustain an electrical potential difference of at least 700V across its thickness without dielectric breakdown. In other embodiments, the insulation on each of the electrical leads may sustain an electrical potential difference of between about 200 V to about 2,000 V across its thickness without dielectric breakdown, including all values and sub-ranges in between. The lead (1122) of the electrode (1120) may be insulated through the balloon (1112). In some embodiments, the saline in the balloon (1112) and the electrode (1120) may form an anode-cathode pair. For example, the balloon (1112) may be configured as a cathode and the electrode (1120) may be configured as an anode. The device (1110) may receive a pulse waveform to be delivered to the ostium of the pulmonary veins (1102). For example a biphasic signal may be applied to ablate tissue. The pulse waveform may create an intense electric field around the electrode (1120) while the current is applied via capacitive coupling to the balloon (1112) to complete the circuit. In some embodiments, the electrode (1120) may include a fine gauge wire and the balloon (1112) may include a wire mesh.

In another embodiment, the electrode (1120) may be advanced through the pulmonary veins (1102) and disposed in one or more of the pulmonary vein ostia without being advanced through the balloon (1112) and/or the septum (1106). The balloon (1112) and electrode (1120) may be configured as a cathode-anode pair and receive a pulse waveform in the same manner as discussed above.

Return Electrode

Figure 12A:
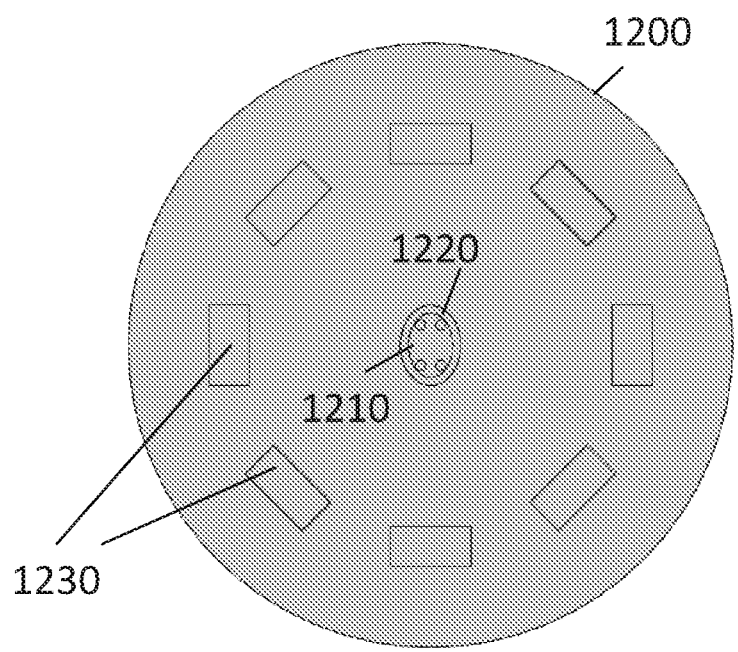
FIGS. 12A-12B are schematic views of a return electrode of an ablation system, according to embodiments.
Figure 12B:
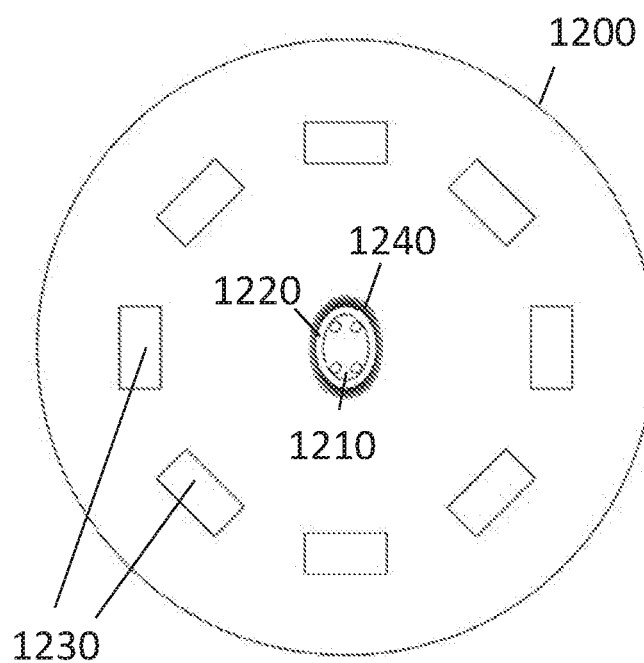

Some embodiments of an ablation system as described herein may further include a return electrode or a distributed set of return electrodes coupled to a patient to reduce the risk of unintended damage to healthy tissue. FIGS. 12A-12B are schematic views of a set of return electrodes (1230) (e.g., return pad) of an ablation system disposed on a patient (1200). A set of four ostia of the pulmonary veins (1210) of the left atrium are illustrated in FIGS. 12A-12B. An electrode (1220) of an ablation device may be positioned around one or more of the ostia of the pulmonary veins (1210). In some embodiments, a set of return electrodes (1230) may be disposed on a back of a patient (1200) to allow current to pass from the electrode (1220) through the patient (1200) and then to the return electrode (1230).

For example, one or more return electrodes may be disposed on a skin of a patient (1200). In one embodiment, eight return electrodes (1230) may be positioned on the back of the patient so as to surround the pulmonary vein ostia (1210). A conductive gel may be applied between the return electrodes (1230) and the skin to improve contact. It should be appreciated that any of the ablation devices described herein may be used with the one or more return electrodes (1230). In FIGS. 12A-12B, the electrode (1220) is disposed around four ostia (1210).

FIG. 12B illustrates the energized electrode (1220) forming an electric field (1240) around the ostia (1210) of the pulmonary veins. The return electrode (1230) may in turn receive a pulsed monophasic and/or biphasic waveform delivered by the electrode (1220). In some embodiments, the number of return electrodes (1230) may be approximately inversely proportional to the surface area of the return electrodes (1230).

For each of the ablation devices discussed herein, the electrodes (e.g., ablation electrode, return electrode) may include biocompatible metals such as titanium, palladium, silver, platinum or a platinum alloy. For example, the electrode may preferably include platinum or a platinum alloy. Each electrode may include an electrical lead having sufficient electrical insulation to sustain an electrical potential difference of at least 700V across its thickness without dielectric breakdown. In other embodiments, the insulation on each of the electrical leads may sustain an electrical potential difference of between about 200 V to about 2500 V across its thickness without dielectric breakdown, including all values and sub-ranges in between. The insulated electrical leads may run to the proximal handle portion of the catheter from where they may be connected to a suitable electrical connector. The catheter shaft may be made of a flexible polymeric material such as Teflon, Nylon, Pebax, etc.

II. Methods

Also described here are methods for ablating tissue in a heart chamber using the systems and devices described above. The heart chamber may be the left atrial chamber and include its associated pulmonary veins. Generally, the methods described here include introducing and disposing a device in contact with one or more pulmonary vein ostial or antral regions. A pulse waveform may be delivered by one or more electrodes of the device to ablate tissue. In some embodiments, a cardiac pacing signal may synchronize the delivered pulse waveforms with the cardiac cycle. Additionally or alternatively, the pulse waveforms may include a plurality of levels of a hierarchy to reduce total energy delivery. The tissue ablation thus performed may be delivered in synchrony with paced heartbeats and with less energy delivery to reduce damage to healthy tissue. It should be appreciated that any of the ablation devices described herein may be used to ablate tissue using the methods discussed below as appropriate.

Figure 13:
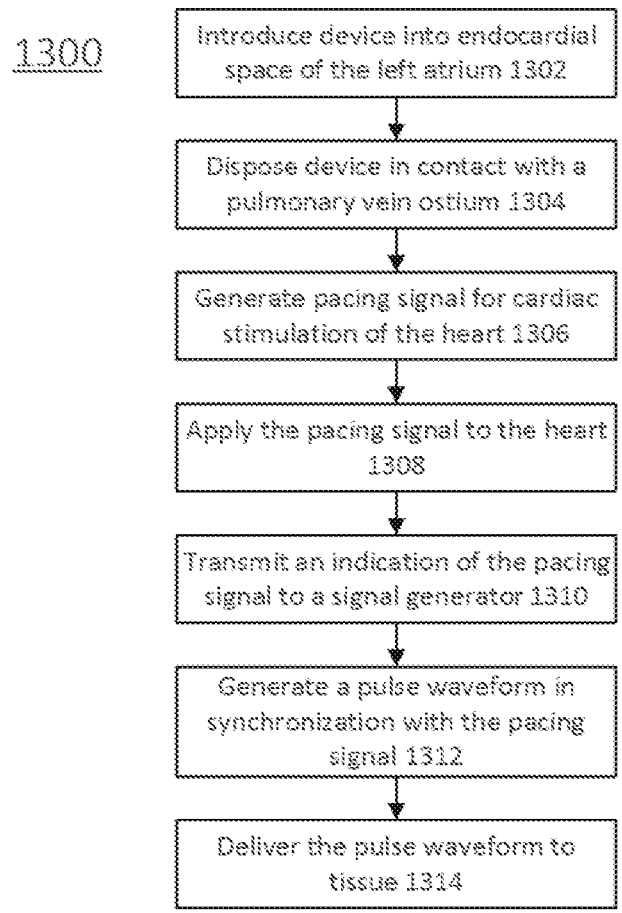
FIG. 13 illustrates a method for tissue ablation, according to embodiments.

FIG. 13 is a method (1300) for one embodiment of a tissue ablation process. In some embodiments, the voltage pulse waveforms described herein may be applied during a refractory period of the cardiac cycle so as to avoid disruption of the sinus rhythm of the heart. The method (1300) includes introduction of a device (e.g., ablation device, such as the ablation device (110), and/or any of the ablation devices (200, 300, 400, 500, 600, 700, 800, 900, 1010, 1110) into an endocardial space of a left atrium at step (1302). The device may be advanced to be disposed in contact with a pulmonary vein ostium (1304). For example, electrodes of an ablation device may form an approximately circular arrangement of electrodes disposed in contact with an inner radial surface at a pulmonary vein ostium. In some embodiments, a pacing signal may be generated for cardiac stimulation of the heart (1306). The pacing signal may then be applied to the heart (1308). For example, the heart may be electrically paced with a cardiac stimulator to ensure pacing capture to establish periodicity and predictability of the cardiac cycle. One or more of atrial and ventricular pacing may be applied. An indication of the pacing signal may be transmitted to a signal generator (1310). A time window within the refractory period of the cardiac cycle may then be defined within which one or more voltage pulse waveforms may be delivered. In some embodiments, a refractory time window may follow a pacing signal. For example, a common refractory time window may lie between both atrial and ventricular refractory time windows.

A pulse waveform may be generated in synchronization with the pacing signal (1312). For example, a voltage pulse waveform may be applied in the common refractory time window. In some embodiments, the pulse waveform may be generated with a time offset with respect to the indication of the pacing signal. For example, the start of a refractory time window may be offset from the pacing signal by a time offset. The voltage pulse waveform(s) may be applied over a series of heartbeats over corresponding common refractory time windows. The generated pulse waveform may be delivered to tissue (1314). In some embodiments, the pulse waveform may be delivered to pulmonary vein ostium of a heart of a patient via one or more splines of a set of splines of an ablation device. In other embodiments, voltage pulse waveforms as described herein may be selectively delivered to electrode subsets such as anode-cathode subsets for ablation and isolation of the pulmonary vein. For example, a first electrode of a group of electrodes may be configured as an anode and a second electrode of the group of electrodes may be configured as a cathode. These steps may be repeated for a desired number of pulmonary vein ostial or antral regions to have been ablated (e.g., 1, 2, 3, or 4 ostia).

Figure 14:
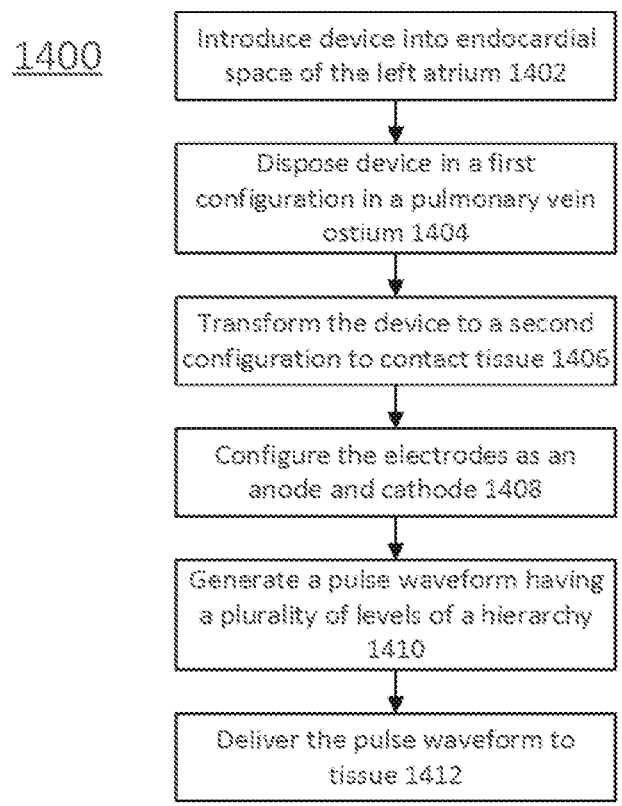
FIG. 14 illustrates a method for tissue ablation, according to other embodiments.

In some embodiments, hierarchical voltage pulse waveforms having a nested structure and a hierarchy of time intervals as described herein may be useful for irreversible electroporation, providing control and selectivity in different tissue types. FIG. 14 is a flowchart (1400) of another embodiment of a tissue ablation process. The method (1400) includes the introduction of a device (e.g., ablation device, such as any of the ablation devices (200, 300, 400, 500, 600, 700, 800, 900, 1010, 1110) into an endocardial space of a left atrium (1402). The device may be advanced to be disposed in a pulmonary vein ostium (1404). In embodiments where the device may include a first and second configuration (e.g., compact and expanded), the device may be introduced in the first configuration and transformed to a second configuration to contact tissue at or near the pulmonary vein antrum or ostium (1406). The device may include electrodes and may be configured in anode-cathode subsets (1408) as discussed in detail above. For example, a subset of electrodes of the devices may be selected as anodes, while another subset of electrodes of the device may be selected as cathodes, with the voltage pulse waveform applied between the anodes and cathodes.

A pulse waveform may be generated by a signal generator (e.g., the signal generator 122) and may include a plurality of levels in a hierarchy (1410). A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). As discussed above, one or more of the waveforms applied across the anode-cathode subsets may be applied during the refractory period of a cardiac cycle. The pulse waveform may be delivered to tissue (1412). It should be appreciated that the steps described in FIGS. 13 and 14 may be combined and modified as appropriate.

Figure 15:
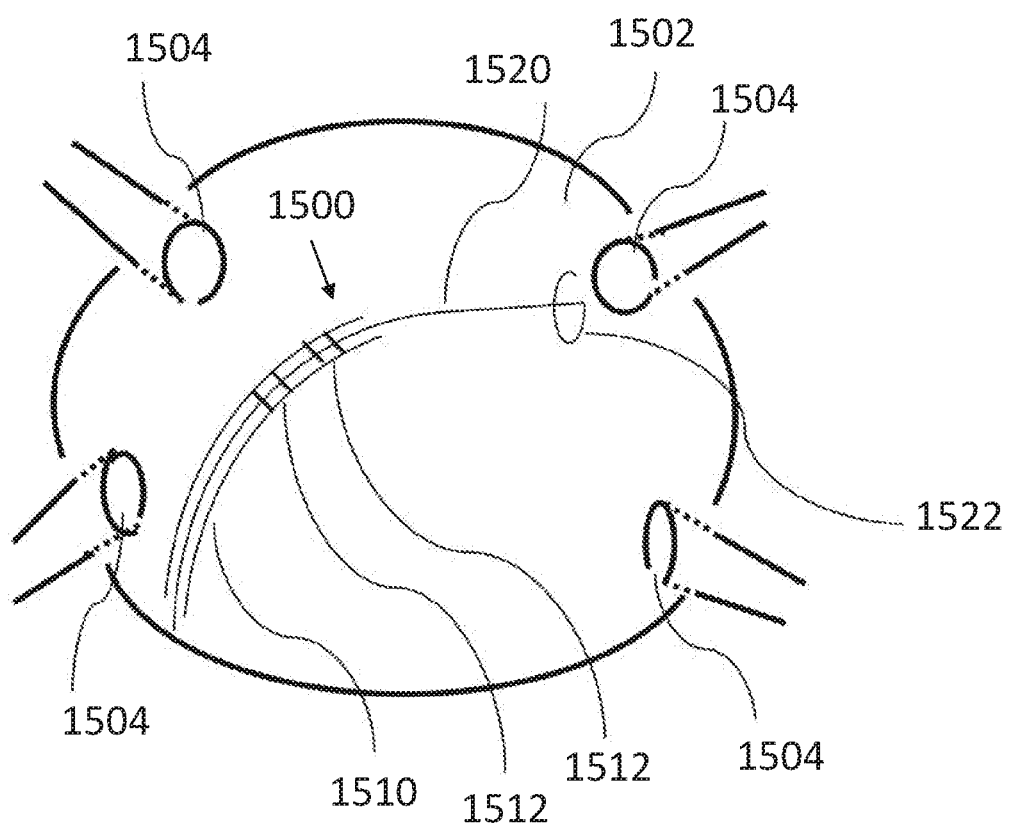
FIG. 15 is an illustration of the ablation catheter depicted in FIG. 2 disposed in a left atrial chamber of a heart.

FIGS. 15-18 depict embodiments of the methods for ablating tissue in a left atrial chamber of the heart as described above using the ablation devices described herein (e.g., FIGS. 2-5). FIG. 15 is a cross-sectional view of an embodiment of a method to ablate tissue disposed in a left atrial chamber of a heart using an ablation device (1500) corresponding to the ablation device (210) depicted in FIG. 2. The left atrial chamber (1502) is depicted having four pulmonary veins (1504) and the ablation device (1500) may be used to ablate tissue sequentially to electrically isolate one or more of the pulmonary veins (1504). As shown in FIG. 15, the ablation device (1500) may be introduced into an endocardial space such as the left atrial chamber (1502) using a trans-septal approach (e.g., extending from a right atrial chamber through the septum and into the left atrial chamber (1502)). The ablation device (1500) may include a catheter (1510) and a guidewire (1520) slidable within a lumen of the catheter (1510). A distal portion of the catheter (1510) may include a set of electrodes (1512). A distal portion (1522) of the guidewire (1520) may be advanced into the left atrial chamber (1502) so as to be disposed near an ostium of a pulmonary vein (1504). The catheter (1510) may then be advanced over the guidewire (1520) to dispose the electrodes (1512) near the ostium of the pulmonary vein (1504). Once the electrodes (1512) are in contact with the ostium of the pulmonary vein (1504), the electrodes (1512) may be configured in anode-cathode subsets. A voltage pulse waveform generated by a signal generator (not shown) may be delivered to tissue using the electrodes (1512) in synchrony with paced heartbeats and/or include a waveform hierarchy. After completion of tissue ablation in one of the pulmonary veins (1504), the catheter (1510) and guidewire (1520) may be repositioned at another pulmonary vein (1504) to ablate tissue in one or more of the remaining pulmonary veins (1504).

Figure 16:
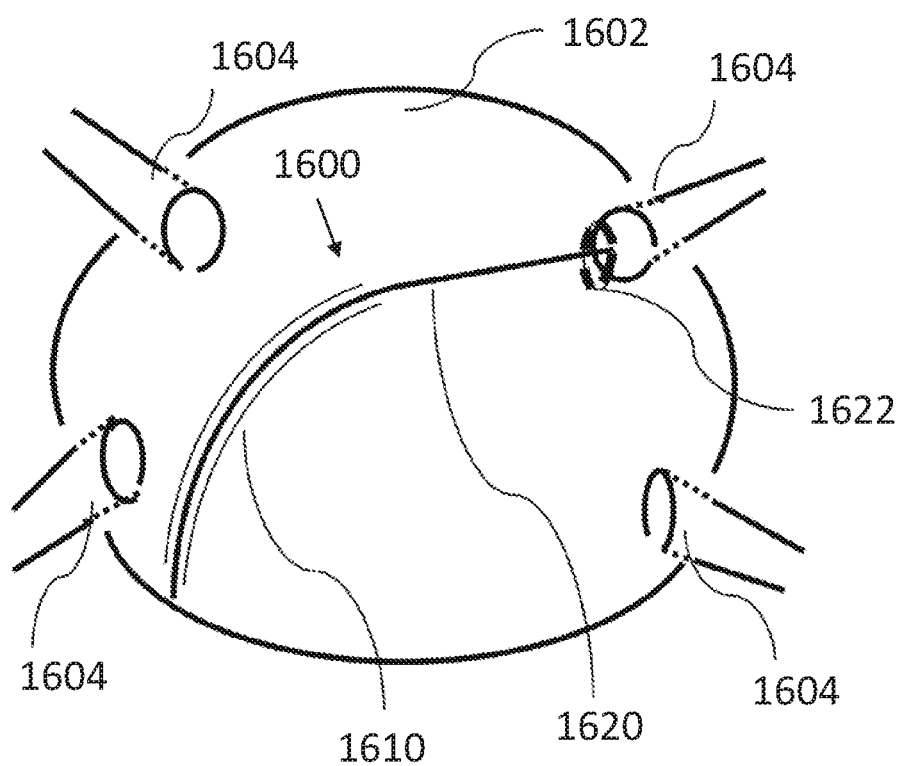
FIG. 16 is an illustration of the ablation catheter depicted in FIG. 3 disposed in a left atrial chamber of a heart.

FIG. 16 is a cross-sectional view of an embodiment of a method to ablate tissue disposed in a left atrial chamber of a heart using an ablation device (1600) corresponding to the ablation device (310) depicted in FIG. 3. The left atrial chamber (1602) is depicted having four pulmonary veins (1604) and the ablation device (1600) may be used to ablate tissue sequentially to electrically isolate one or more of the pulmonary veins (1604). As shown in FIG. 16, the ablation device (1600) may be introduced into an endocardial space such as the left atrial chamber (1602) using a trans-septal approach. The ablation device (1600) may include a sheath (1610) and a catheter (1620) slidable within a lumen of the sheath (1610). A distal portion (1622) of the catheter (1620) may include a set of electrodes. A distal portion (1622) of the catheter (1620) may be advanced into the left atrial chamber (1602) to dispose the electrodes near an ostium of a pulmonary vein (1604). Once the electrodes are in contact with the ostium of the pulmonary vein (1604), the electrodes may be configured in anode-cathode subsets. A voltage pulse waveform generated by a signal generator (not shown) may be delivered to tissue using the electrodes in synchrony with paced heartbeats and/or include a waveform hierarchy. After completion of tissue ablation in the pulmonary vein (1604), the catheter (1620) may be repositioned at another pulmonary vein (1604) to ablate tissue in one or more of the remaining pulmonary veins (1604).

Figure 17:
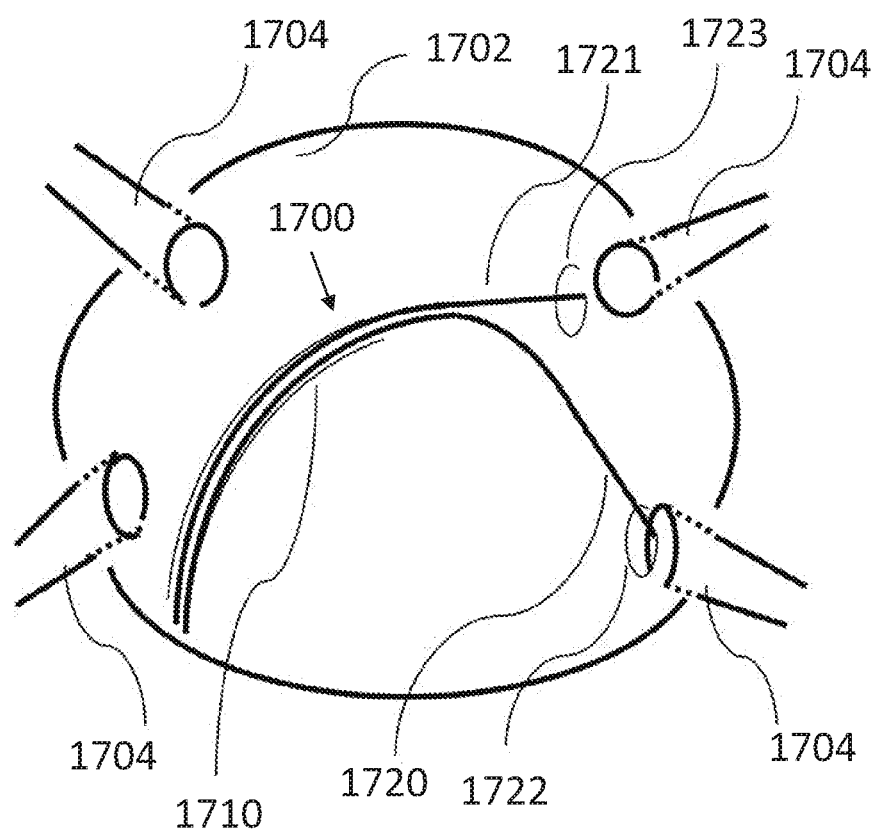
FIG. 17 is an illustration of two of the ablation catheters depicted in FIG. 4 disposed in a left atrial chamber of a heart.

FIG. 17 is a cross-sectional view of an embodiment of a method to ablate tissue disposed in a left atrial chamber of a heart using an ablation device corresponding to the ablation device (410) depicted in FIG. 4. The left atrial chamber (1702) is depicted having four pulmonary veins (1704) and the ablation device (1700) may be used to ablate tissue to electrically isolate one or more of the pulmonary veins (1704). As shown in FIG. 17, the ablation device (1700) may be introduced into an endocardial space such as the left atrial chamber (1702) using a trans-septal approach. The ablation device (1700) may include a sheath (1710) and a plurality of catheters (1720, 1721) slidable within a lumen of the sheath (1710). Each of the catheters (1720, 1721) may include a respective guidewire (1722, 1723) slidable within the catheter (1720, 1721). A distal portion of the guidewire (1722, 1723) may include an electrode configured to deliver a voltage pulse waveform. Each of the catheters (1720, 1721) and corresponding guidewires (1722, 1723) may be advanced into the left atrial chamber (1702) so as to be disposed near respective ostia of the pulmonary veins (1704). Once the guidewire electrodes (1722, 1723) are in contact with the ostium of the pulmonary vein (1704), the electrodes may be configured in anode-cathode subsets. For example, a first guidewire (1722) may be configured as an anode while a second guidewire (1723) may be configured as a cathode. In this configuration, voltage pulse waveforms generated by a signal generator (not shown) may be delivered for ablation and simultaneous isolation of the pair of pulmonary veins (1704). Additionally or alternatively, a voltage pulse waveform may be delivered to tissue using the electrodes in synchrony with paced heartbeats and/or include a waveform hierarchy. After completion of tissue ablation in two of the pulmonary veins (1704), the catheters (1720, 1721) may be repositioned to ablate tissue at the two remaining pulmonary veins (1704). In some embodiments, the sheath (1710) may include three or four catheters to be disposed in the pulmonary veins (1704).

Figure 18:
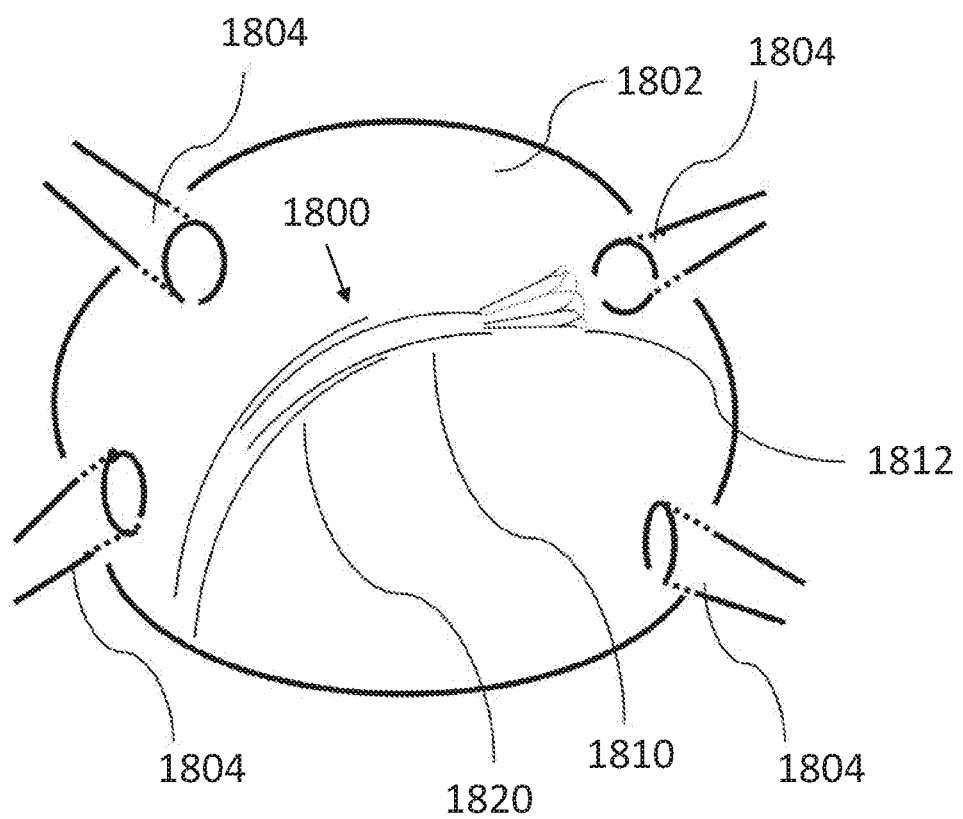
FIG. 18 is an illustration of the ablation catheter depicted in FIG. 5 disposed in a left atrial chamber of a heart.

FIG. 18 is a cross-sectional view of an embodiment of a method to ablate tissue disposed in a left atrial chamber of a heart using an ablation device (1800) corresponding to the ablation device (500) depicted in FIG. 5. The left atrial chamber (1802) is depicted having four pulmonary veins (1804) and the ablation device (1800) may be used to ablate tissue sequentially to electrically isolate one or more of the pulmonary veins (1804). As shown in FIG. 18, the ablation device may be introduced into an endocardial space such as the left atrial chamber (1802) using a trans-septal approach. The ablation device may include a sheath (1820) and a catheter (1810) slidable within a lumen of the sheath (1820). A distal portion (1812) of the catheter (1810) may be flower-shaped as discussed in detail with respect to FIG. 5. A distal portion (1812) of the catheter (1810) may be advanced into the left atrial chamber (1802) in a compact first configuration and disposed near an ostium of a pulmonary vein (1804). The distal portion (1812) of the catheter (1810) may then be transformed to an expanded second configuration to form a flower-shaped distal portion, as shown in FIG. 18, such that the distal portion (1812) of the catheter (1810) is disposed near the ostium of the pulmonary vein (1804). Once the electrodes are in contact with the ostium of the pulmonary vein (1804), the electrodes may be configured in anode-cathode subsets. A voltage pulse waveform generated by a signal generator (not shown) may be delivered to tissue using the electrodes in synchrony with paced heartbeats and/or include a waveform hierarchy. After completion of tissue ablation in the pulmonary vein (1804), the catheter (1810) may be repositioned at another pulmonary vein (1804) to ablate tissue in one or more of the remaining pulmonary veins (1804).

It should be appreciated that any of the methods described herein (e.g., FIGS. 13-18) may further include coupling a return electrode (e.g., one or more return electrodes (1230) depicted in FIGS. 12A-12B) to a patient's back and configured to safely remove current from the patient during application of a voltage pulse waveform.

Figure 19A:
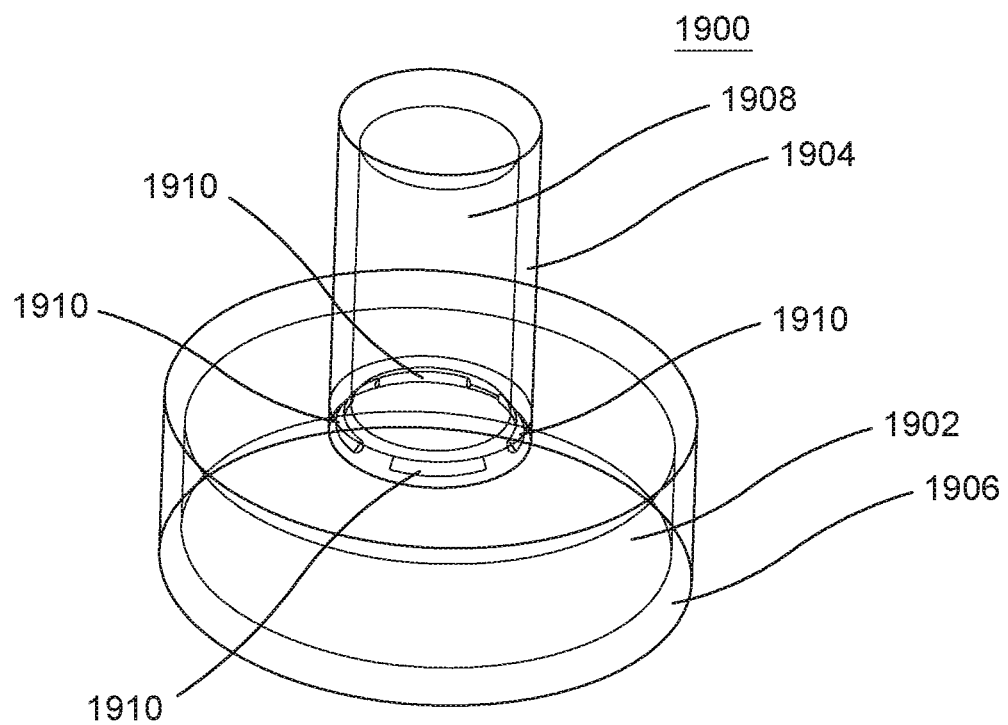
FIGS. 19A-19B are illustrative views of a set of electrodes disposed in a pulmonary vein ostium, according to other embodiments.

FIGS. 19A-20B depict embodiments of electrodes disposed in contact around an ostium of a pulmonary vein and electric fields generated therefrom. FIG. 19A is a schematic representation (1900) of an embodiment of a set of electrodes (1910) disposed in an ostium of a pulmonary vein (1904). A left atrial chamber (1902) may include a blood pool (1906) and the pulmonary vein (1904) may include a blood pool (1908). The left atrial chamber (1902) and pulmonary vein (1904) may each have a wall thickness of up to about 4 mm.

Figure 19B:
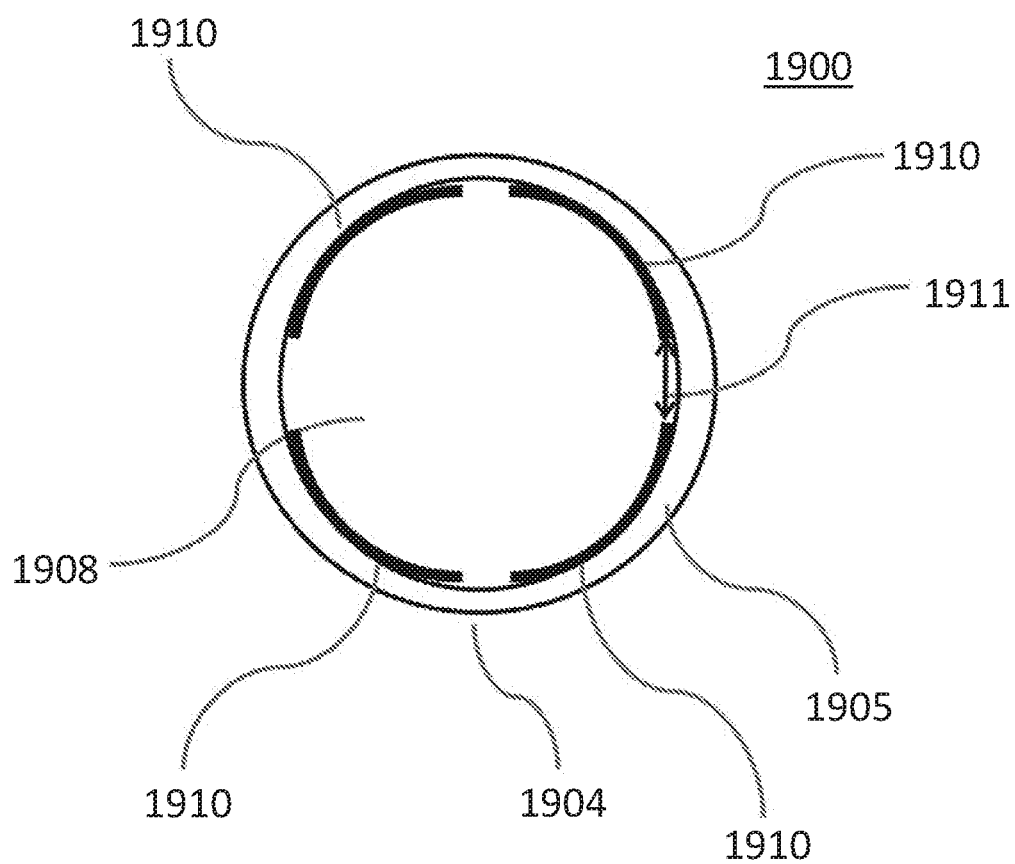

FIG. 19B is another schematic representation (1900) of the set of electrodes (1910) disposed radially along an interior surface of a pulmonary vein (1904). The pulmonary vein (1904) may include an arterial wall (1905) containing a blood pool (1908). Adjacent electrodes (1910) may be separated by a predetermined distance (1911). In some embodiments, the pulmonary vein (1904) may have an inner diameter of about 16 mm. In FIGS. 19A-19B, the electrodes (1910) may have a length of about 10 mm and be spaced apart about 4 mm from each other. It should be appreciated that the electrodes (1910) may in other embodiments be any of the electrodes disclosed herein. For example, the electrodes (1910) may include the electrodes of the flower-shaped distal portion of FIG. 5 and/or the generally circular arrangement of electrodes depicted in FIG. 3.

Figure 20A:
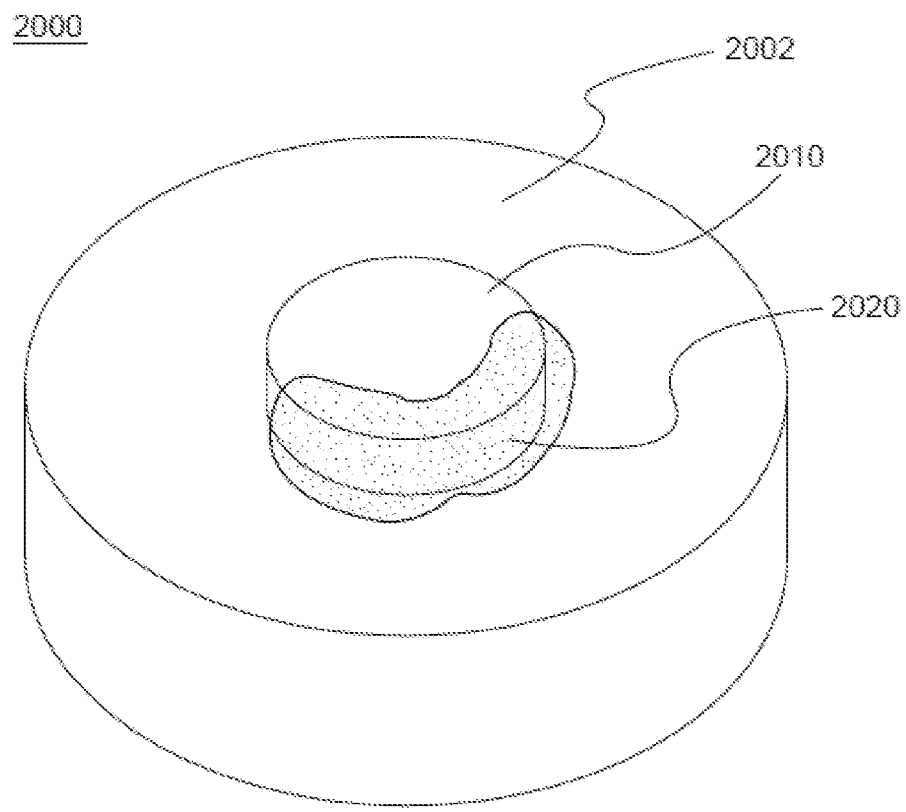
FIGS. 20A-20B are illustrative views of an electric field generated by electrodes disposed in a pulmonary vein ostium, according to other embodiments.
Figure 20B:
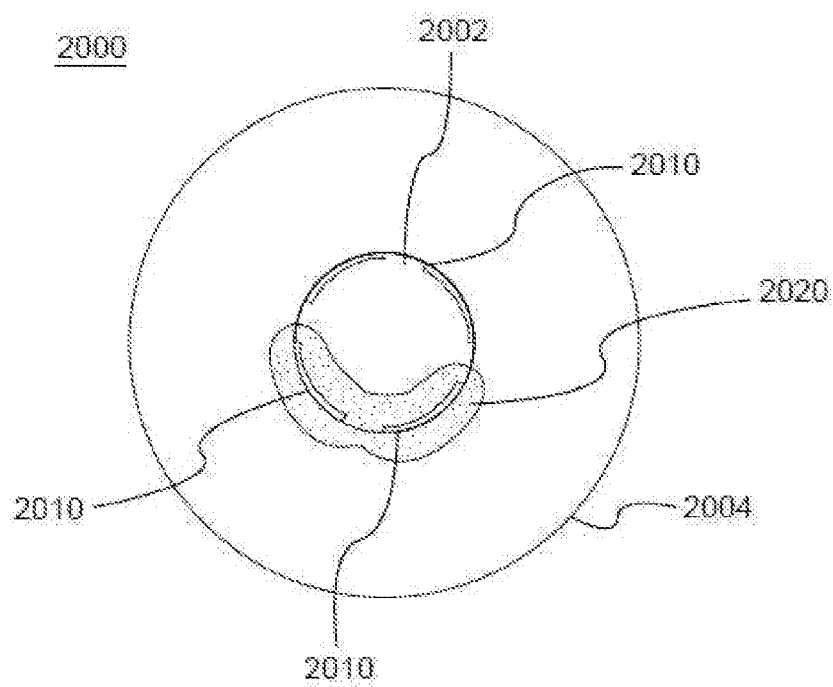

FIGS. 20A-20B are schematic representations (2000) of an embodiment of an electric field (2020) generated by a set of electrodes (2010) disposed in an ostium of a pulmonary vein (2002). FIG. 20A is a perspective view while FIG. 20B is a cross-sectional view of the pulmonary vein (2002) and outer wall of the left atrial chamber (2004). The shaded electric field (2020) illustrates where the electric field (2020) exceeds a threshold value when adjacent electrodes (2010) deliver energy (e.g., voltage pulse waveform) to ablate tissue. For example, the electric field (2020) represents a potential difference of 1500 V applied between adjacent electrodes (2010). Under this applied voltage, the electric field (2020) magnitude is at least above a threshold value of 500 V/cm within the shaded volumetric electric field (2020) and may be sufficient to generate irreversible ablation in cardiac tissue. By sequencing pulse waveforms over adjacent pairs of electrodes (2010) as described above in detail, a pulmonary vein (2002) ostium may be ablated to electrically isolate the pulmonary vein (2002) from the left atrial chamber (2004).

Figure 33A:
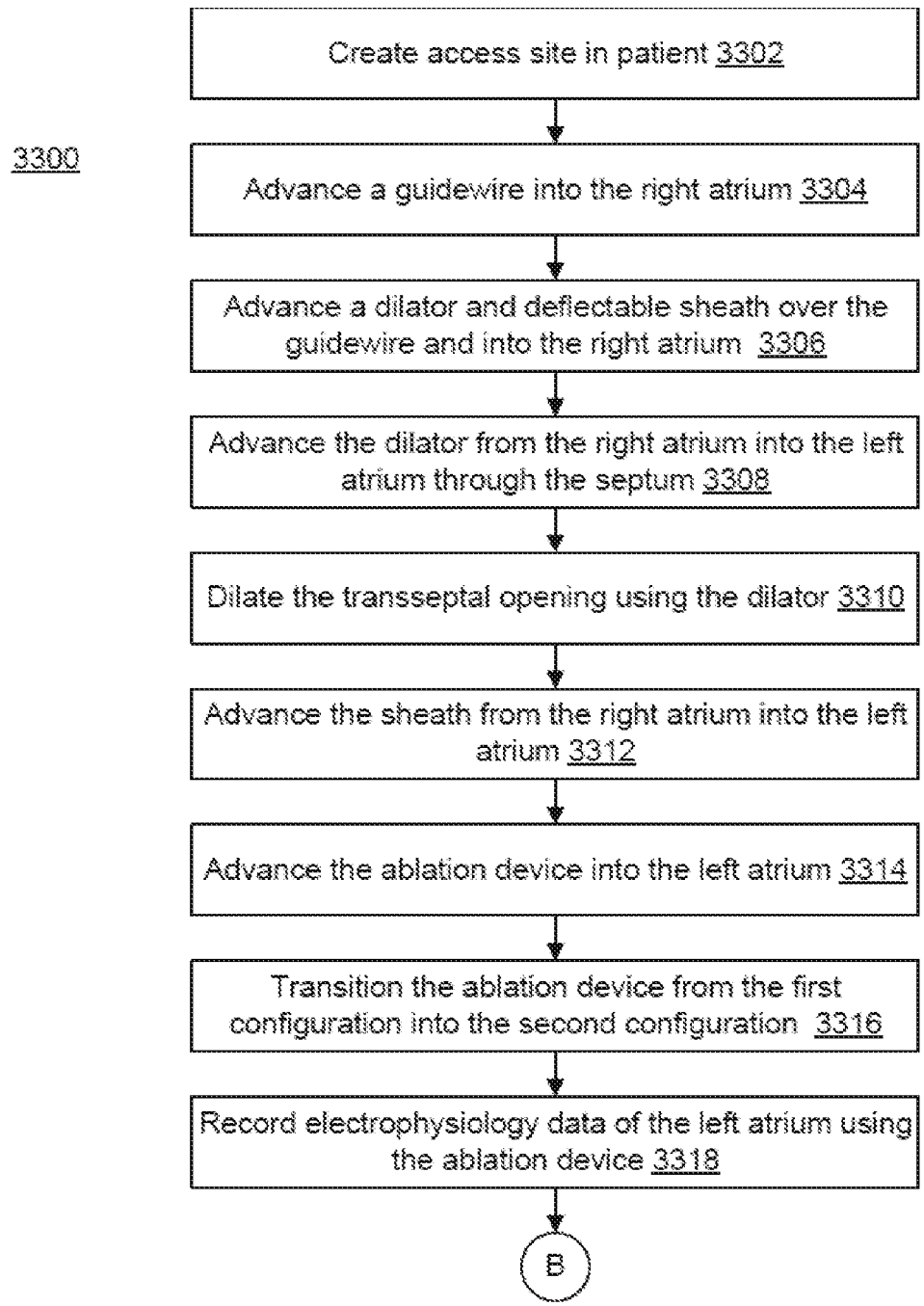
FIGS. 33A-33B illustrate a method for tissue ablation, according to other embodiments.
Figure 33B:
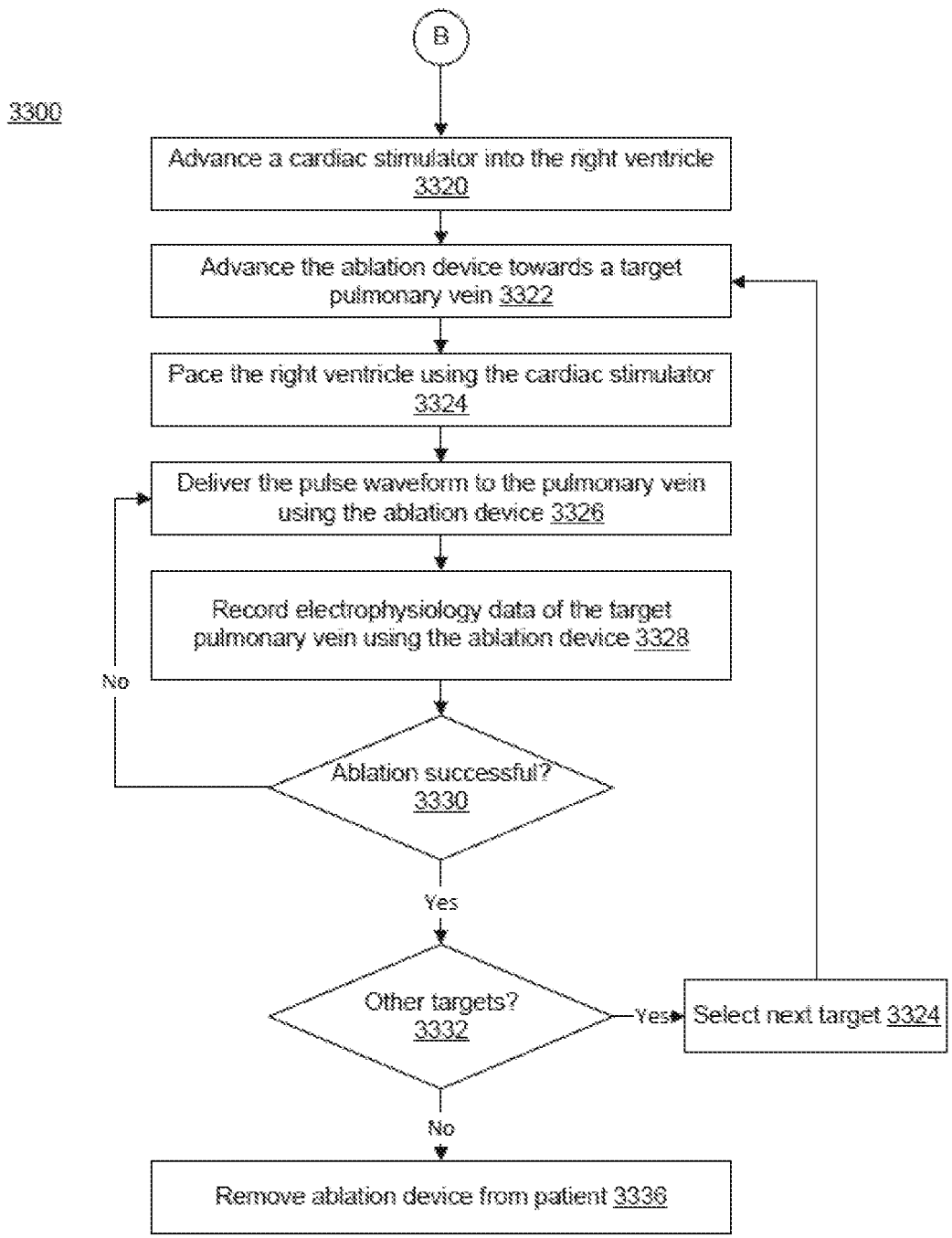

FIGS. 33A-33B illustrates another method (3300) for a tissue ablation process, according to some embodiments. Generally, the method (3300) includes the introduction of a device (e.g., ablation device, such as the ablation devices (2600, 2800, 2900) into an endocardial space of a left atrium and in contact with a pulmonary vein antrum or ostium. The ablation device may be introduced in a first configuration and transitioned to a second configuration in the left atrium. Once positioned in the pulmonary vein antrum or ostium, voltage pulse waveforms may be applied to tissue during a refractory period of the cardiac cycle. Electrophysiology data of the left atrium may be recorded to determine efficacy of the ablation.

The method (3300) may begin with creating an access site in a patient (3302). For example, to access the left ventricle for treatment, an antegrade delivery approach may be used, in which the first access site may be via a femoral vein of the patient. A guidewire may be advanced into the access site via the femoral vein and into the right atrium of the patient (3304). A dilator and a deflectable sheath may be advanced over the guidewire and into the right atrium (3306). The sheath may have a distal portion configured for a maximum deflection of at least about 180 degrees. The sheath may deflect in order to guide the ablation device through vasculature and/or point a distal end of the ablation device at a target (e.g., pulmonary vein). The dilator may be advanced from the right atrium into the left atrium through the septum (3308) to create a transseptal opening. For example, the dilator may be advanced from the right atrium into the left atrium through the interatrial septum to create the transseptal opening. The interatrial septum may include the fossa ovalis of the patient. The transseptal opening may be dilated using the dilator (3310). For example, the dilator may be advanced out of the sheath and used to poke the fossa ovalis to create the transseptal opening (assuming the patient is heparinized). Alternatively, a transseptal needle (e.g., Brockenbrough needle) may be used to create the transseptal opening. The sheath may be advanced from the right atrium into the left atrium (3312) through the transseptal opening. An ablation device may be advanced into the left atrium over the guidewire (3314) via the mitral valve.

In some embodiments, the ablation device may include a shaft lumen and a set of splines extending from a distal end of the shaft lumen. Each spline of the set of splines may include one or more electrodes formed on a surface of that spline with the distal ends of the set of splines coupled together. The set of splines may be configured for translation along a longitudinal axis of the shaft lumen to transition between a first configuration and a second configuration. One or more electrodes of the set of splines may be configured to receive electrophysiology signals from the left atrium (e.g., pulmonary veins). In the method of FIGS. 33A-33B, an ablation device may be configured to record electrophysiology data of the left atrium. To allow the ablation device to record electrophysiology data, the ablation device may be transitioned from the first configuration into the second configuration (3316) within the left atrium. In some embodiments, the transition from the first configuration to the second configuration may be performed without contacting an atrial wall and the pulmonary ostium. Transitioning configurations prior to contact with tissue allows the set of splines to deploy into their intended shape (e.g., symmetrical) and not be caught (e.g., bunched up) against tissue. The ablation device in the second configuration may be advanced to contact one or more pulmonary veins of the left atrium to record electrophysiology data using the ablation device (3318). For example, one or more electrodes on each spline of the set of splines may be configured for receiving an ECG signal for recording electrophysiology data. In some variations, the ablation device may record electrophysiology data in an intermediate configuration between the first and second configurations.

In some embodiments, after recording electrophysiology data of a pulmonary vein using the ablation device, the ablation device may be retracted from the pulmonary vein and transitioned from the second configuration to a third configuration (e.g., an intermediate configuration) between the first and second configurations. In some embodiments, the ablation device in a third configuration may then be advanced to another pulmonary vein to record electrophysiology data. The recorded electrophysiology data may include intracardiac ECG signal data. The ablation device may transition from the third configuration to the first configuration without contacting an atrial wall and the pulmonary ostium to aid repositioning of the ablation device. For example, the ablation device may then be advanced to another pulmonary ostium for recording electrophysiology data. These steps may be repeated for a plurality of pulmonary veins in the left atrium. In some embodiments, the set of splines may be transitioned between the first, second, and third configurations using a handle of the ablation device (e.g., FIGS. 28A, 30A-30C). The handle may be manually rotated by an operator to transition the ablation device between a lock configuration and an unlock configuration. For example, when the ablation device is advanced through vasculature or through the heart, handle may be in the lock configuration. The lock configuration may fix a translational position of the set of splines relative to the catheter shaft and the unlock configuration permits translation of the set of splines relative to the catheter shaft. Prior to transition between the first, second, and third configurations, the handle may be rotated to the unlock configuration. In some embodiments, the ablation device may transition between three or more configurations, such as four, five, six, seven, eight, nine, and ten different configurations. For example, the handle may be translated longitudinally between seven lock configuration providing corresponding seven deployment geometries of the set of splines.

In other embodiments, a separate diagnostic device (e.g., a mapping catheter) may be used to record electrophysiology data of the left atrium to be treated. Electrophysiology data may be used to generate an anatomical map that may be used to compare electrophysiology data recorded after energy delivery. The diagnostic device may be advanced into the left atrium via a femoral vein or jugular vein. In these embodiments, the diagnostic device (e.g., second catheter) may be advanced into the left atrium over the guidewire after step (3312) instead of advancing the ablation device into the left atrium. The second catheter may be used to record electrophysiology data of one or more pulmonary veins of the left atrium. Once completed, the diagnostic device may be withdrawn from the body over the guidewire, and the ablation device may then be advanced over the guidewire into the left atrium.

Turning back to FIGS. 33A-33B, a second access site may be created in the patient to advance a cardiac stimulator into the patient's heart. For example, the second access site may be via a jugular vein of the patient. The cardiac stimulator may be advanced into the right ventricle through the second access site (3320) (e.g., near the apex of the right ventricle). A pacing signal may be generated by the cardiac stimulator and applied to the heart for cardiac stimulation of the heart. An indication of the pacing signal may be transmitted from the cardiac stimulator to the signal generator. During use, the signal generator may be configured for generating the pulse waveform in synchronization with the indication of the pacing signal. In some embodiments, the operator may confirm the pacing capture and determine that the ventricle is responding to the pacing signal as intended. For example, pacing capture may be confirmed on an ECG display on a signal generator. Confirmation of pacing capture is a safety feature in that ablation is delivered in synchrony with pacing through enforced periodicity of a Q-wave through pacing.

The ablation device may be advanced towards a target pulmonary vein (3322) for delivering a pulse waveform configured for tissue ablation. In particular, the ablation device in the second configuration may be advanced towards a pulmonary ostium of the heart to contact the pulmonary ostium. The sheath may be deflected as needed to direct the ablation device towards the target pulmonary vein. When pressed against the pulmonary ostium, the set of splines in the second configuration may bend towards the proximal portion of the catheter shaft. That is, the set of splines may form an umbrella-like shape on fluoroscopic imaging due to contact between the set of splines and the pulmonary ostium. Once the ablation device is in position within the heart to deliver one or more pulse waveforms, an extension cable may be used to electrically couple a signal generator to a proximal end of the handle of the ablation device.

After pacing the right ventricle using the pacing device (3324), the pulse waveform may be delivered to the pulmonary ostium using the ablation device to ablate tissue in the vicinity of the target pulmonary ostium (3326). The pulse waveform may be delivered in synchronization with the pacing signal.

As described in detail with respect to FIG. 32, the ablation device in the second configuration may be configured to generate a set of circumferential field lines generally parallel with a longitudinal axis of a set of myocardial cells disposed circumferentially in an atrial wall. For example, the set of splines of the ablation device in the second configuration may generate circumferential electric field lines having a high density that are aligned (e.g., parallel) with a set of myocardial cells in the atrial wall. This allows energy to be delivered more efficiently and thus permits a reduction in energy delivered to tissue. For example, tissue ablation may be provided using a pulse waveform between about 900 V and 1200 V, which in some cases may be half of the voltage conventionally needed to ablate tissue.

The set of splines and corresponding electrodes may be configured in a number of embodiments for tissue ablation. In some embodiments, a first set of electrodes of a first spline of the set of splines may be configured as an anode, and a second set of electrodes of a second spline may be configured as a cathode. A pulse waveform may be delivered to the first set of electrodes and the second set of electrodes. The first spline may be non-adjacent to the second spline such that the splines do not overlap and create a short circuit. In some embodiments, the anode and cathode may be configured to generate an ablation area in a pulmonary ostium having a diameter of between about 2 cm and about 6 cm using the pulse waveform. In some of these embodiments, the first set of electrodes may comprise one electrode and the second set of electrodes may comprise at least two electrodes. Delivery of the pulse waveform may include sequentially activating the electrodes of different pairs of splines. For example, for an eight spline ablation device, two non-adjacent splines may deliver a predetermined pulse waveform. Once a first pair of splines completes energy delivery, another pair of non-adjacent splines may deliver another pulse waveform until each spline of the set of splines delivers energy to the pulmonary ostium. In some embodiments, pairs of splines may activate sequentially in a clockwise or counter-clockwise manner. Accordingly, one ablation cycle may deliver energy to the entire pulmonary vein. In some embodiments, the pulmonary vein may undergo a plurality of ablation cycles before delivering energy to a second pulmonary vein.

As discussed herein, the pulse waveform may be generated by a signal generator coupled to the ablation device. The signal generator may be electrically coupled to a proximal end of a handle of the ablation device. For example, an extension cable may electrically couple the signal generator to the proximal end of the handle. In some embodiments, the pulse waveform may include a time offset with respect to the pacing signal. In some embodiments, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval.

One or more electrodes of the set of splines in the second configuration may be configured to receive electrophysiology signals of the target pulmonary vein and used to record electrophysiology data of the target pulmonary vein (3328). The electrophysiology data may be compared to the baseline data recorded prior to ablation to determine if ablation was successful (3330).

In other embodiments, the ablation device may be withdrawn from the heart over the guidewire and a mapping catheter may be advanced over the guidewire to record the post-ablation electrophysiology data of the target pulmonary vein. If the ablation is not successful (3330—NO) based on the electrophysiology data and predetermined criteria, then the process may return to step 3326 for delivery of additional pulse waveforms. The pulse waveform parameters may be the same or changed for subsequent ablation cycles.

If analysis of the electrophysiology data indicates that the ablation of a pulmonary vein is successful (e.g., pulmonary vein is electrically isolated) (3330—YES), then a determination may be made of other target pulmonary veins to ablate (3332). Another target pulmonary vein may be selected (3324) and the process may return to step 3322 when other pulmonary veins are to be ablated. For example, ablation of the right superior pulmonary vein may be followed by ablation of the left superior pulmonary vein. When switching between target pulmonary veins, the set of splines may be transitioned from the second configuration after ablation of the pulmonary ostium, and the ablation device may be advanced towards another pulmonary ostium of the set of pulmonary ostia. The set of splines may be transitioned from the second configuration to a third configuration (e.g., intermediate configuration) different from the first and second configurations. If no other pulmonary veins are to be ablated (3332—NO), the ablation device, cardiac stimulator, sheath, guidewire, and the like, may be removed from the patient (3336).

In other embodiments, the diagnostic device (e.g., mapping catheter) may be used to record electrophysiology data of the left atrium after pulse waveforms are delivered to tissue by the ablation device. In these embodiments, the ablation device may be withdrawn from the patient over the guidewire after steps 3326 or 3336 and the diagnostic device may be advanced into the left atrium over the guidewire to record electrophysiology data of the target pulmonary vein having undergone tissue ablation.

It should be noted that for any of the steps described herein, a radiopaque portion of the ablation device may be fluoroscopically imaged to aid an operator. For example, visual confirmation may be performed through fluoroscopic imaging that the set of splines in the second configuration are not in contact with the pulmonary vein or to visually confirm an antral apposition of the set of splines relative to the pulmonary vein. In some embodiments, the set of splines may be just outside the atrium. Imaging from a plurality of angles may be used to confirm positioning.

Pulse Waveform

Disclosed herein are methods, systems and apparatuses for the selective and rapid application of pulsed electric fields/waveforms to effect tissue ablation with irreversible electroporation. The pulse waveform(s) as disclosed herein are usable with any of the systems (100), devices (e.g., 200, 300, 400, 500, 600, 700, 800, 900, 1010, 1110, 1230, 1500, 1600, 1700, 1800, 1910, 2010), and methods (e.g., 1300, 1400) described herein. Some embodiments are directed to pulsed high voltage waveforms together with a sequenced delivery scheme for delivering energy to tissue via sets of electrodes. In some embodiments, peak electric field values can be reduced and/or minimized while at the same time sufficiently large electric field magnitudes can be maintained in regions where tissue ablation is desired. This also reduces the likelihood of excessive tissue damage or the generation of electrical arcing, and locally high temperature increases.

In some embodiments, a system useful for irreversible electroporation includes a signal generator and a processor capable of being configured to apply pulsed voltage waveforms to a selected plurality or a subset of electrodes of an ablation device. In some embodiments, the processor is configured to control inputs whereby selected pairs of anode-cathode subsets of electrodes can be sequentially triggered based on a pre-determined sequence, and in one embodiment the sequenced delivery can be triggered from a cardiac stimulator and/or pacing device. In some embodiments, the ablation pulse waveforms are applied in a refractory period of the cardiac cycle so as to avoid disruption of the sinus rhythm of the heart. One example method of enforcing this is to electrically pace the heart with a cardiac stimulator and ensure pacing capture to establish periodicity and predictability of the cardiac cycle, and then to define a time window well within the refractory period of this periodic cycle within which the ablation waveform is delivered.

In some embodiments, the pulsed voltage waveforms disclosed herein are hierarchical in organization and have a nested structure. In some embodiments, the pulsed waveform includes hierarchical groupings of pulses with a variety of associated timescales. Furthermore, the associated timescales and pulse widths, and the numbers of pulses and hierarchical groupings, can be selected so as to satisfy one or more of a set of Diophantine inequalities involving the frequency of cardiac pacing.

Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered. This in turn can broaden the areas of clinical application of electroporation including therapeutic treatment of a variety of cardiac arrhythmias.

Figure 21:
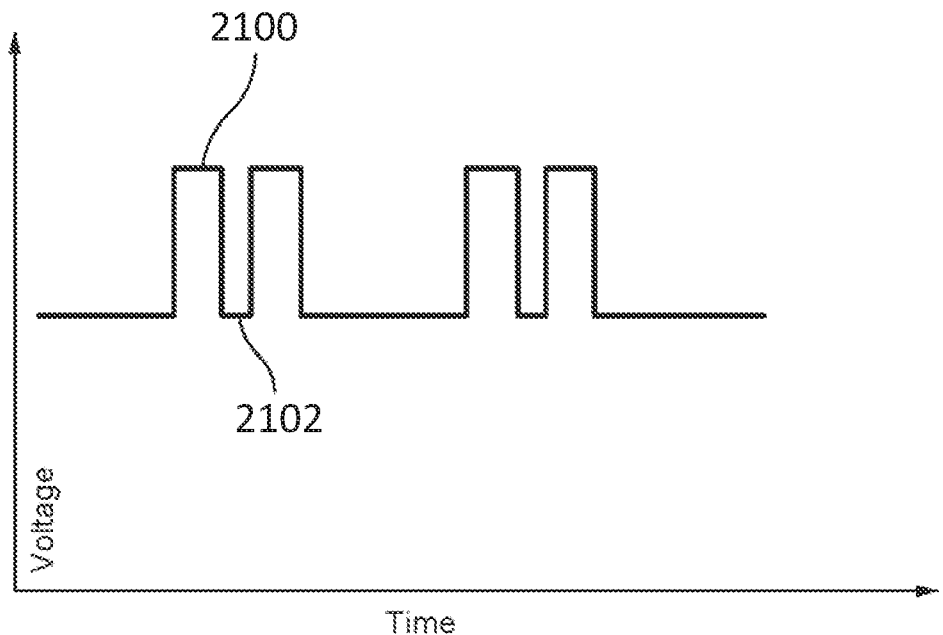
FIG. 21 is an example waveform showing a sequence of voltage pulses with a pulse width defined for each pulse, according to embodiments.

FIG. 21 illustrates a pulsed voltage waveform in the form of a sequence of rectangular double pulses, with each pulse, such as the pulse (2100) being associated with a pulse width or duration. The pulse width/duration can be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 21 illustrates a set of monophasic pulses where the polarities of all the pulses are the same (all positive in FIG. 21, as measured from a zero baseline). In some embodiments, such as for irreversible electroporation applications, the height of each pulse (2100) or the voltage amplitude of the pulse (2100) can be in the range from about 400 volts, about 1,000 volts, about 5,000 volts, about 10,000 volts, about 15,000 volts, including all values and sub ranges in between. As illustrated in FIG. 21, the pulse (2100) is separated from a neighboring pulse by a time interval (2102), also sometimes referred to as a first time interval. The first time interval can be about 10 microseconds, about 50 microseconds, about 100 microseconds, about 200 microseconds, about 500 microseconds, about 800 microseconds, about 1 millisecond including all values and sub ranges in between, in order to generate irreversible electroporation.

Figure 22:
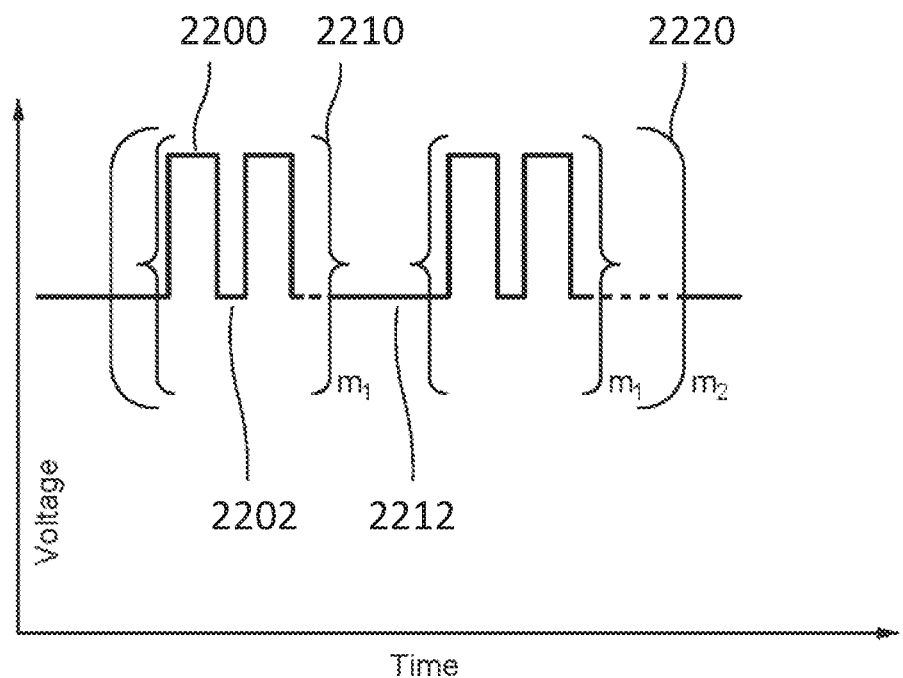
FIG. 22 schematically illustrates a hierarchy of pulses showing pulse widths, intervals between pulses, and groupings of pulses, according to embodiments.

FIG. 22 introduces a pulse waveform with the structure of a hierarchy of nested pulses. FIG. 22 shows a series of monophasic pulses such as pulse (2200) with pulse width/pulse time duration w, separated by a time interval (also sometimes referred to as a first time interval) such as (2202) of duration $t_1$ between successive pulses, a number $m_1$ of which are arranged to form a group of pulses (2210) (also sometimes referred to as a first set of pulses). Furthermore, the waveform has a number $m_2$ of such groups of pulses (also sometimes referred to as a second set of pulses) separated by a time interval (2212) (also sometimes referred to as a second time interval) of duration $t_2$ between successive groups. The collection of $m_2$ such pulse groups, marked by (2220) in FIG. 22, constitutes the next level of the hierarchy, which can be referred to as a packet and/or as a third set of pulses. The pulse width and the time interval $t_1$ between pulses can both be in the range of microseconds to hundreds of microseconds, including all values and sub ranges in between. In some embodiments, the time interval $t_2$ can be at least three times larger than the time interval $t_1$. In some embodiments, the ratio $t_2/t_1$ can be in the range between about 3 and about 300, including all values and sub-ranges in between.

Figure 23:
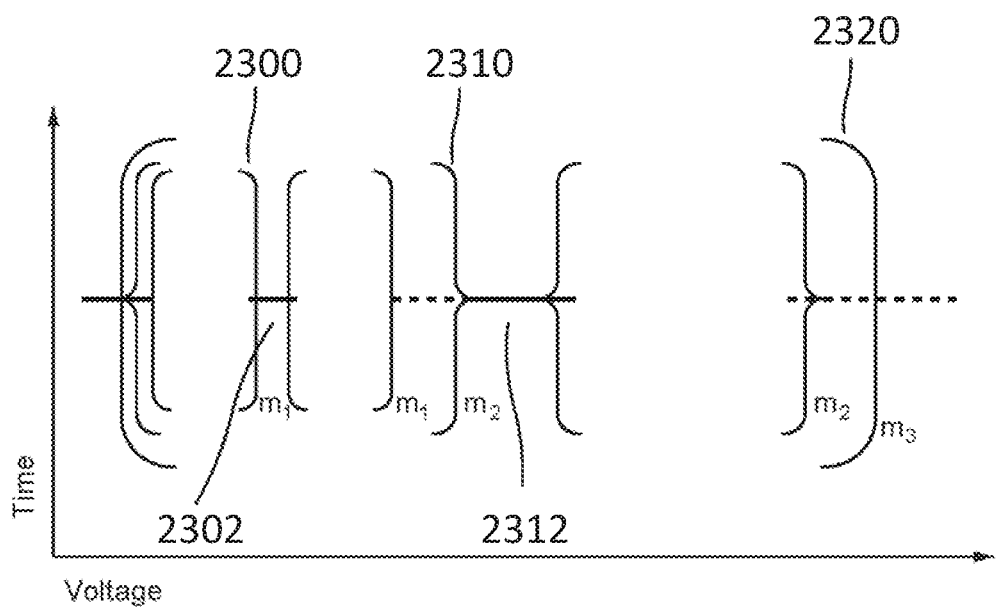
FIG. 23 provides a schematic illustration of a nested hierarchy of monophasic pulses displaying different levels of nested hierarchy, according to embodiments.

FIG. 23 further elaborates the structure of a nested pulse hierarchy waveform. In this figure, a series of $m_1$ pulses (individual pulses not shown) form a group of pulses (2300) (e.g., a first set of pulses). A series of $m_2$ such groups separated by an inter-group time interval (2310) of duration $t_2$ (e.g., a second time interval) between one group and the next form a packet 132 (e.g., a second set of pulses). A series of $m_3$ such packets separated by time intervals (2312) of duration $t_3$ (e.g., a third time interval) between one packet and the next form the next level in the hierarchy, a super-packet labeled (2320) (e.g., a third set of pulses) in the figure. In some embodiments, the time interval $t_3$ can be at least about thirty times larger than the time interval $t_2$. In some embodiments, the time interval $t_3$ can be at least fifty times larger than the time interval $t_2$. In some embodiments, the ratio $t_3/t_2$ can be in the range between about 30 and about 800, including all values and sub-ranges in between. The amplitude of the individual voltage pulses in the pulse hierarchy can be anywhere in the range from 500 volts to 7,000 volts or higher, including all values and sub ranges in between.

Figure 24:
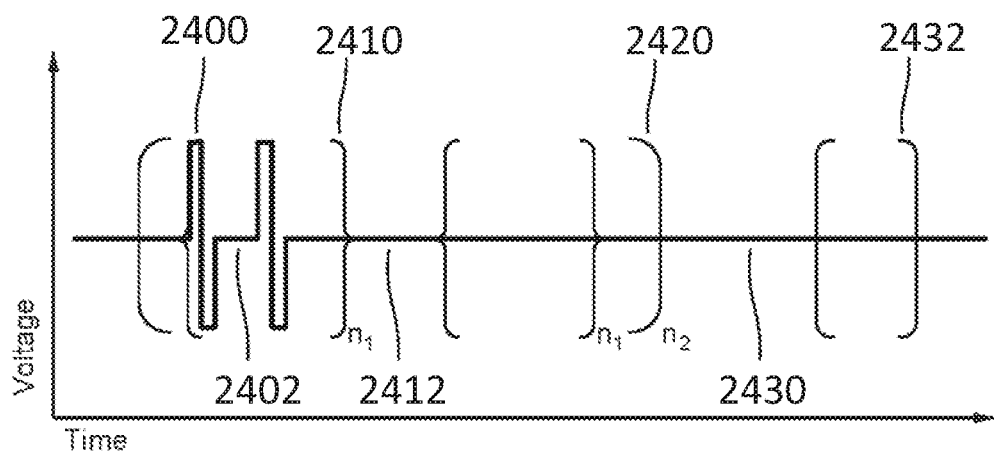
FIG. 24 is a schematic illustration of a nested hierarchy of biphasic pulses displaying different levels of nested hierarchy, according to embodiments.

FIG. 24 provides an example of a biphasic waveform sequence with a hierarchical structure. In the example shown in the figure, biphasic pulses such as (2400) have a positive voltage portion as well as a negative voltage portion to complete one cycle of the pulse. There is a time delay (2402) (e.g., a first time interval) between adjacent cycles of duration $t_1$, and $n_1$ such cycles form a group of pulses (2410) (e.g., a first set of pulses). A series of $n_2$ such groups separated by an inter-group time interval (2412) (e.g., a second time interval) of duration $t_2$ between one group and the next form a packet (2420) (e.g., a second set of pulses). The figure also shows a second packet (2430), with a time delay (2432) (e.g., a third time interval) of duration $t_3$ between the packets. Just as for monophasic pulses, higher levels of the hierarchical structure can be formed as well. The amplitude of each pulse or the voltage amplitude of the biphasic pulse can be anywhere in the range from 500 volts to 7,000 volts or higher, including all values and sub ranges in between. The pulse width/pulse time duration can be in the range from nanoseconds or even sub-nanoseconds to tens of microseconds, while the delays $t_1$ can be in the range from zero to several microseconds. The inter-group time interval $t_2$ can be at least ten times larger than the pulse width. In some embodiments, the time interval $t_3$ can be at least about twenty times larger than the time interval $t_2$. In some embodiments, the time interval $t_3$ can be at least fifty times larger than the time interval $t_2$.

Embodiments disclosed herein include waveforms structured as hierarchical waveforms that include waveform elements/pulses at various levels of the hierarchy. The individual pulses such as (2200) in FIG. 22 comprise the first level of the hierarchy, and have an associated pulse time duration and a first time interval between successive pulses. A set of pulses, or elements of the first level structure, form a second level of the hierarchy such as the group of pulses/second set of pulses (2210) in FIG. 22. Among other parameters, associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses can be between about 20 microseconds and about 10 milliseconds, including all values and subranges in between. A set of groups, second set of pulses, or elements of the second level structure, form a third level of the hierarchy such as the packet of groups/third set of pulses (2220) in FIG. 22. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses can be between about 60 microseconds and about 200 milliseconds, including all values and sub ranges in between. The generally iterative or nested structure of the waveforms can continue to a higher plurality of levels, such as ten levels of structure, or more.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms can be generated with a suitable pulse generator. It is understood that while the examples herein identify separate monophasic and biphasic waveforms for clarity, it should be noted that combination waveforms, where some portions of the waveform hierarchy are monophasic while other portions are biphasic, can also be generated/implemented.

In some embodiments, the ablation pulse waveforms described herein are applied during the refractory period of the cardiac cycle so as to avoid disruption of the sinus rhythm of the heart. In some embodiments, a method of treatment includes electrically pacing the heart with a cardiac stimulator to ensure pacing capture to establish periodicity and predictability of the cardiac cycle, and then defining a time window within the refractory period of the cardiac cycle within which one or more pulsed ablation waveforms can be delivered. FIG. 25 illustrates an example where both atrial and ventricular pacing is applied (for instance, with pacing leads or catheters situated in the right atrium and right ventricle respectively). With time represented on the horizontal axis, FIG. 25 illustrates a series of ventricular pacing signals such as (2500) and (2510), and a series of atrial pacing signals (2520, 2530), along with a series of ECG waveforms (2540, 2542) that are driven by the pacing signals. As indicated in FIG. 25 by the thick arrows, there is an atrial refractory time window (2522) and a ventricular refractory time window (2502) that respectively follow the atrial pacing signal (2522) and the ventricular pacing signal (2500). As shown in FIG. 25, a common refractory time window (2550) of duration $T_r$ can be defined that lies within both atrial and ventricular refractory time windows (2522, 2502). In some embodiments, the electroporation ablation waveform(s) can be applied in this common refractory time window (2550). The start of this refractory time window (2522) is offset from the pacing signal (2500) by a time offset (2504) as indicated in FIG. 25. The time offset (2504) can be smaller than about 25 milliseconds, in some embodiments. At the next heartbeat, a similarly defined common refractory time window (2552) is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy can be applied over a heartbeat, so that a series of packets is applied over a series of heartbeats, for a given electrode set.

It should be understood that the examples and illustrations in this disclosure serve exemplary purposes and departures and variations such as numbers of splines, number of electrodes, and so on can be built and deployed according to the teachings herein without departing from the scope of this invention.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

We claim:

1. A method, comprising:
   advancing an ablation device into a chamber of a heart, the ablation device including:
      a catheter shaft defining a longitudinal axis and a shaft lumen therethrough; and
      a set of splines coupled to the catheter shaft, each spline of the set of splines including a set of electrodes formed on a surface of each spline of the set of splines;
   transitioning, after advancing the ablation device into the chamber, the ablation device from a first configuration in which a distal portion of each spline of the set of splines is disposed a first distance from a distal end of the catheter shaft to a second configuration in which the distal portion of each spline from the set of splines is disposed a second distance less than the first distance from the distal end of the catheter shaft;
   moving the ablation device to a first location near a first pulmonary vein of a set of pulmonary veins;
   delivering, when the ablation device is in the second configuration, an ablation pulse waveform to the ablation device such that the ablation device generates a pulsed electric field to ablate a region of tissue;
   moving, after delivering the ablation pulse waveform, the ablation device to a second location near a second pulmonary vein of the set of pulmonary veins; and
   transitioning the ablation device to a third configuration different from the first configuration and the second configuration.

2. The method of claim 1, wherein the ablation pulse waveform is a first ablation pulse waveform and the region of tissue is a first region of tissue, the method further comprising:
   delivering, when the ablation device is in the third configuration, a second ablation pulse waveform to the ablation device such that the ablation device generates a pulsed electric field to ablate a second region of tissue.

3. The method of claim 2, wherein the first region of tissue overlaps the second region of tissue.

4. The method of claim 1, wherein at least one spline of the set of splines is in contact with tissue surrounding a pulmonary vein ostium when the ablation device is in each of the second and third configurations.

5. The method of claim 1, further comprising:
   recording, when the ablation device is in one of the second or third configurations, electrophysiology data of the heart.

6. The method of claim 1, wherein the pulmonary vein is a first pulmonary vein, and the second location is near a second pulmonary vein of the set of pulmonary veins.

7. The method of claim 1, wherein, when the ablation device is in the third configuration, the distal portion of each spline of the set of splines is disposed a third distance from the distal end of the catheter shaft, the third distance being different from the first distance and the second distance.

8. The method of claim 1, wherein the pulsed electric field includes a set of electric field lines that are generally parallel with a longitudinal axis of a set of myocardial cells disposed circumferentially in an atrial wall of the heart.

9. The method of claim 1, wherein a ratio of the first distance to the second distance is between about 3:1 and about 25:1.

10. The method of claim 1, wherein the ablation device transitions from the first configuration into the second configuration and to the third configuration without contacting an atrial wall and the pulmonary vein.

11. The method of claim 1, wherein the method further comprises:
    advancing a pacing device into cardiac anatomy; and
    delivering a pacing signal to the heart using the pacing device with the ablation pulse waveform delivered to the ablation device in synchronization with the pacing signal.

12. The method of claim 1, wherein the first pulmonary vein is the second pulmonary vein.

13. A method, comprising:
    advancing an ablation device into a chamber of a heart, the ablation device including:
       a catheter shaft defining a longitudinal axis and a shaft lumen therethrough; and
       a set of splines coupled to the catheter shaft, each spline of the set of splines including a set of electrodes formed on a surface of each spline of the set of splines;
    transitioning, after advancing the ablation device into the chamber, the ablation device from a first configuration in which a distal portion of each spline of the set of splines is disposed a first distance from a distal end of the catheter shaft to a second configuration in which the distal portion of each spline from the set of splines is disposed a second distance less than the first distance from the distal end of the catheter shaft;
    advancing the ablation device toward a pulmonary vein of a set of pulmonary veins; and
    delivering, when the ablation device is in the second configuration, an ablation pulse waveform to anode-cathode electrode sets according to a predetermined sequence, each anode-cathode electrode set including a first set of electrodes formed on a first subset of the splines configured as anodes and a second set of electrodes formed on a second subset of the splines configured as cathodes.

14. The method of claim 13, wherein:
    the set of electrodes formed on each spline of the set of splines includes a distal electrode and a proximal electrode,
    the first set of electrodes includes the distal electrode formed on each spline of the first subset of the splines, and
    the second set of electrodes includes the proximal electrode formed on each spline from the second subset of the splines.

15. The method of claim 13, wherein the set of electrodes formed on each spline of the set of splines are distributed proximal and distal to a midpoint of the respective spline by a ratio of about 1 to 3.

16. The method of claim 13, wherein delivering the ablation pulse waveform to the anode-cathode electrode sets generates a set of ablation areas along a wall of a pulmonary vein antrum or ostium.

17. The method of claim 16, wherein each ablation area of the set of ablation areas has a diameter of between about 1 cm and about 6 cm.

18. The method of claim 16, wherein the set of ablation areas forms a contiguous transmural lesion that results in electrical isolation of the pulmonary vein.

19. The method of claim 13, wherein delivering the ablation pulse waveform to the anode-cathode electrode sets generates a set of electric field lines generally parallel with a longitudinal axis of a set of myocardial cells disposed circumferentially in an atrial wall of heart.

20. An apparatus, comprising:
a catheter shaft defining a longitudinal axis and a shaft lumen therethrough; and
a set of splines extending from a distal end of the shaft lumen, a distal portion of each spline of the set of splines extending distally from a distal end of the catheter shaft, each spline of the set of splines including a set of electrodes formed on a surface of that spline, the set of splines configured to transition between a first configuration in which the set of splines are arranged substantially parallel to the longitudinal axis and a second configuration in which each spline of the set of splines has a radius of curvature that decreases and subsequently increases along a length of that spline.

21. The apparatus of claim 20, wherein, when the set of splines are in the second configuration, the radius of curvature of at least a portion of each spline of the set of splines is between about 7 mm and about 25 mm.

22. The apparatus of claim 20, wherein the set of splines in the second configuration are arranged as a set of non-overlapping loops.

23. The apparatus of claim 20, wherein a distal end of each spline of the set of splines is disposed at a first distance from the distal end of the catheter shaft when the set of splines are in the first configuration and at a second distance from the distal end of the catheter shaft when the set of splines are in the second configuration, a ratio of the first distance to the second distance being between about 5:1 and about 25:1.

24. The apparatus of claim 20, wherein the set of electrodes for each spline in the set of splines includes an insulated electrical lead associated therewith and configured for sustaining a voltage potential of at least about 700 V without dielectric breakdown.

25. The apparatus of claim 20, wherein each spline of the set of splines includes an elliptical cross-section, and the elliptical cross-section includes a major axis length between about 1 mm and about 2.5 mm and a minor axis length between about 0.4 mm and about 1.4 mm.

26. The apparatus of claim 20, wherein, when the set of splines are in the second configuration, each spline of the set of splines has a helix angle of less than about 10 degrees relative to the longitudinal axis.

27. The apparatus of claim 20, wherein the set of electrodes formed on each spline of the set of splines includes at least one electrode configured for ablation and at least one electrode configured for measuring electrophysiology data.

28. A method, comprising:
advancing an ablation device into a chamber of a heart, the ablation device including:
a catheter shaft defining a longitudinal axis and a shaft lumen therethrough; and
a set of splines coupled to the catheter shaft, each spline of the set of splines including a set of electrodes formed on a surface of each spline of the set of splines;
transitioning, after advancing the ablation device into the chamber, the ablation device from a first configuration in which the set of splines are arranged substantially parallel to the longitudinal axis to a second configuration in which each spline of the set of splines has a radius of curvature that decreases and subsequently increases along a length of that spline;
advancing the ablation device to toward a pulmonary vein of a set of pulmonary veins; and
delivering, when the ablation device is in the second configuration, an ablation pulse waveform to the ablation device such that the ablation device generates a pulsed electric field to ablate tissue.

* * * * *